US007314631B1

(12) United States Patent
Murphy et al.

(10) Patent No.: US 7,314,631 B1
(45) Date of Patent: *Jan. 1, 2008

(54) USE OF RECOMBINANT LIVE-ATTENUATED PARAINFLUENZA VIRUS (PIV) AS A VECTOR TO PROTECT AGAINST DISEASE CAUSED BY PIV AND RESPIRATORY SYNCYTIAL VIRUS (RSV)

(75) Inventors: Brian R. Murphy, Bethesda, MD (US); Peter L. Collins, Rockville, MD (US); Anna P. Durbin, Takoma Park, MD (US); Mario H. Skiadopoulos, Potomac, MD (US); Tao Tao, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/458,813

(22) Filed: Dec. 10, 1999

Related U.S. Application Data

(63) Continuation-in-part of application No. 09/083,793, filed on May 22, 1998.

(60) Provisional application No. 60/059,385, filed on Sep. 19, 1997, provisional application No. 60/047,575, filed on May 23, 1997.

(51) Int. Cl.
*A61K 39/155* (2006.01)
*C12N 7/00* (2006.01)
(52) U.S. Cl. ............... 424/211.1; 424/199.1; 435/235.1; 435/325; 435/320.1; 536/23.72
(58) Field of Classification Search ............ 424/184.1, 424/204.1, 205.1, 211.1, 212.1, 93.2; 536/23.1; 514/44; 435/320.1
See application file for complete search history.

(56) References Cited

U.S. PATENT DOCUMENTS

| 5,716,821 A | 2/1998 | Wertz et al. ............ 435/235.1 |
| 5,789,229 A | 8/1998 | Wertz et al. ............ 435/235.1 |
| 5,869,036 A | 2/1999 | Belshe et al. ............ 424/93.2 |
| 6,033,886 A | 3/2000 | Conzelmann ............ 435/172.3 |
| 6,264,957 B1* | 7/2001 | Collins .................... 424/211.1 |

FOREIGN PATENT DOCUMENTS

| EP | 0 440 219 A1 | 8/1991 |
| EP | 0 702 085 A1 | 3/1996 |
| WO | WO93/14207 | 7/1993 |
| WO | WO97/06270 | 2/1997 |
| WO | WO97/11093 | 3/1997 |
| WO | WO97/20468 | 6/1997 |
| WO | WO98/02530 | 1/1998 |
| WO | WO98/43668 | 10/1998 |
| WO | WO98/53078 | 11/1998 |
| WO | WO99/02657 | 1/1999 |
| WO | WO99/15631 | 4/1999 |

OTHER PUBLICATIONS

Baron et al., "Rescue of Rinderpest Virus from Cloned cDNA," *J. Virol.* 71:1265-1271, 1997, Copy Enclosed.
Belshe et al., "Cold Adaptation of Parainfluenza Virus Type 3: Induction of Three Phenotypic Markers," *J. Med. Virol.* 10:235-42, 1982.
Blumberg et al., "Measles Virus L Protein Evidences Elements of Ancestral RNA Polymerase," *Virology* 164:487-497, 1988.
Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," *J. Virol.* 73:251-259, 1999, Copy Enclosed.
Bukreyev, et al., "Recovery of Infectious Respiratory Syncytial Virus Expressing an Additional, Foreign Gene," *J. Virol.* 70:6634-41, 1996, Copy Enclosed.
Bukreyev, et al., "Interferon γ Expressed by a Recombinant Respiratory Syncytial Virus Attenuates Virus Replication in Mice Without Compromising Immunogenicity," *Proc. Nat. Acad. Sci. USA* 96:2367-2372, 1999, Copy Enclosed.
Cadd et al., "The Sendai Paramyxiovirus Accessory C Proteins Inhibit Viral Genoma Amplification in Promoter-Specific Fashion," *J. Virol.* 70:5067-74, 1996, Copy Enclosed.

(Continued)

*Primary Examiner*—Stacy B. Chen
(74) *Attorney, Agent, or Firm*—Birch, Stewart, Kolasch & Birch, LLP

(57) ABSTRACT

Chimeric parainfluenza viruses (PIVs) are provided that incorporate a PIV vector genome or antigenome and one or more antigenic determinant(s) of a heterologous PIV or non-PIV pathogen. These chimeric viruses are infectious and attenuated in humans and other mammals and are useful in vaccine formulations for eliciting and immune responses against one or more PIVs, or against a PIV and non-PIV pathogen. Also provided are isolated polynucleotide molecules and vectors incorporating a chimeric PIV genome or antigenome which includes a partial or complete PIV vector genome or antigenome combined or integrated with one or more heterologous gene(s) or genome segment(s) encoding antigenic determinant(s) of a heterologous PIV or non-PIV pathogen. In preferred aspects of the invention, chimeric PIV incorporate a partial or complete human PIV vector genome or antigenome combined with one or more heterologous gene(s) or genome segment(s) from a heterologous PIV or non-PIV pathogen, wherein the chimeric virus is attenuated for use as a vaccine agent by any of a variety of mutations and nucleotide modifications introduced into the chimeric genome or antigenome.

33 Claims, 12 Drawing Sheets
(1 of 12 Drawing Sheet(s) Filed in Color)

OTHER PUBLICATIONS

Collins, et al., "Production of Infectious Human Respiratory Syncytial Virus from Cloned cDNA Confirms an Essential Role of the Transcription Elongation Factor from the 5' Proximal Open Reading Frame of the M2 mRNA in Gene Expression and Provides a Capability for Vaccine Development," *Proc Nat. Acad. Sci. USA* 92:11563-11567, 1995.

Collins et al., "Parainfluenza Viruses", in *Field Virology*, B. N. Fields (Knipe et al., eds.), 3rd ed., vol. 1, p. 1205-1243, Lippincott-Raven Publishers, Philadelphia, 1996.

Conzelmann et al., "Rescue of Synthetic Genomic RNA Analogs of Rabies Virus by Plasmid-Encoded Proteins," *J. Virol.* 68:713-719, 1994.

Conzelmann, "Genetic Manipulation of Non-Segmented Negative-strand RNA Viruses," *J. Gen. Virol.* 77:381-389, 1996.

Curran, et al., "Sendai Virus P Gene Produces Multiple Proteins from Overlapping Open Reading Frames," *Enzyme* 44:224-249, 1990, Copy Enclosed.

Curran, et al., " The Sendai Virus Nonstructural C Proteins Specifically Inhibit Viral mRNA Synthesis," *Virology* 189:647-656, 1992, Copy Enclosed.

Delenda, et al., "Normal Cellular Replication of Sendai Virus Without the *trans*-Frame, Nonstructural V Protein," *Virology* 228:55-62, 1997, Copy Enclosed.

Delenda et al., "Sendai Viruses with Altered P. V, and W Protein Expression," *Virology* 242:327-337, 1998, Copy Enclosed.

Dimock, et al., "Rescue of Synthetic Analogs of Genomic RNA and Replicative-Intermediate RNA of Human Parainfluenza Virus Type 3," *J. Virol.* 67: 2772-2778, 1993.

Durbin et al., "Minimum Protein Requirements for Transcription and RNA Replication of a Minigenome of Human Parainfluenza Virus Type 3 and Evaluation of the Rule of Six," *Virology* 234:74-83, 1997.

Durbin et al., "Recovery of Infectious Human Parainfluenza Virus Type 3 from cDNA," *Virology* 235:323-332, 1997.

Finke et al. "Ambisense Gene Expression for Recombinant Rabies Virus: Random Packaging of Positive- and Negative-Strand Ribonucleoprotein Complexes into Rabies Virions," *J. Virol.* 71:7281-7288, 1997, Copy Enclosed.

Galinski et al., "Molecular Cloning and Sequence Analysis of the Human Parainfluenza 3 Virus mRNA Encoding the P and C Proteins," *Virology* 155:46-60, 1986, Copy Enclosed.

Galinski et al., "Molecular Cloning and Sequence Analysis of the Human Parainfluenza 3 Virus Gene Encoding the L Protein," *Virology* 165:499-510, 1988.

Galinski et al., "RNA Editing in the Phosphoprotein Gene of the Human Parainfluenza Virus Type 3," *Virology* 186:543-550, 1992.

Garcin et al., "A Highly Recombinogenic System for the Recovery of Infectious Sendai Paramyxovirus from cDNA: Generation of a Novel Copy-back Nondefective Interfering Virus," *EMBO J.* 14:6087-6094, 1995.

Garcin et al., "A Point Mutation in the Sendai Virus Accessory C Proteins Attenuates Virulence for Mice, But Not Virus Growth in Cell Culture," *Virology* 238:424-431, 1997, Copy Enclosed.

Grosfeld et al., "RNA Replication by Respiratory Syncytial Virus (RSV) Is Directed by the N, P, and L Proteins; Transcription Also Occurs under These Conditions but Requires RSV Superinfection for Efficient Synthesis of Full-Length mRNA," *J. Virol.* 69: 5677-5686, 1995.

Hall et al., "Cold-passaged Human Parainfluenza Type 3 Viruses Contain *ts* and Non-*ts* Mutations Leading to Attenuation in Rhesus Monkeys," *Virus Res.* 22:173-184, 1992.

Hasan et al., "Creation of an Infectious Recombinant Sendai Virus Expressing the Firefly Luciferase Gene from the 3' Proximal First Locus," *J. Gen. Virol.* 78:2813-20, 1997, Copy Enclosed.

He et al., "Recovery of Infectious SV5 from Cloned DNA and Expression of a Foreign Gene," *Virology* 237:249-260, 1997, Copy Enclosed.

Hoffman et al., "An Infectious Clone of Human Parainfluenza Virus Type 3," *J. Virol.* 71:4272-4277, 1997, Copy Enclosed.

Itoh et al., "Isolation of an Avirulent Mutant of Sendai Virus with Two Amino Acid Mutations from a Highly Virulent Field Strain Through Adaption to LLC-MK$_2$ Cells," *J. Gen. Virol.* 78:3207-3215, 1997, Copy Enclosed.

Jin et al., "Recombinant Human Respiratory Syncytial Virus (RSV) from cDNA and Construction of Subgroup A and B Chimeric RSV," *Virology* 251:206-214, 1998, Copy Enclosed.

Johnson et al., "Specific Targeting to CD4+ Cells of Recombinant Vesicular Stomatitis Viruses Encoding Human Immunodeficiency Virus Envelope Proteins," *J. Virol.* 71:5060-5068, 1997, Copy Enclosed.

Juhasz et al., "The Temperature-Sensitive (*ts*) Phenotype of a Cold-Passaged (*cp*) Live Attenuated Respiratory Syncytial Virus Vaccine Candidate, Designated *cpts*530, Results from a Single Amino Acid Substitution in the L Protein," *J. Virol.* 71:5814-5819, 1997.

Kahn et al., "Recombinant Vesicular Stomatitis Virus Expressing Respiratory Syncytial Virus (RSV) Glycoproteins: RSV Fusion Protein Can Mediate Infection and Cell Fusion," *Virology* 254:81-91, 1999, Copy Enclosed.

Karron et al., "A Live Attenuated Bovine Parainfluenza Virus Type 3 Vaccine is Safe, Infectious, Immunogenic, and Phenotypically Stable in Infants and Children," *J. Inf. Dis.* 171:1107-1114, 1995.

Karron et al., "A Live Human Parainfluenza Type 3 Virus Vaccine Is Attenuated and Immunogenic in Healthy Infants and Children," *J. Inf. Dis.* 172:1445-1450, 1995, Copy Enclosed.

Kato et al., "Initiation of Sendai Virus Multiplication from Transfected cDNA or RNA with Negative or Positive Sense," *Gene to Cells* 1:569-579, 1996.

Kato et al., "The Paramyxovirus, Sendai Virus, V Protein Encodes a Luxury Function Required for Viral Pathogenesis," *EMBO. J.* 16:578-587, 1997, Copy Enclosed.

Kato et al., "Importance of the Cysteine-Rich Carboxyl-Terminal Half of V Protein for Sendai Virus Pathogenesis," *J Virol.* 71:7266-7272, 1997, Copy Enclosed.

Kretzchmar et al., "Normal Replication of Vesicular Stomatitis Virus Without C Proteins," *Virology* 216:309-316, 1996, Copy Enclosed.

Kretzschmar et al., "High-Efficiency Incorporation of Functional Influenza Virus Glycoproteins into Recombinant Vesicular Stomatitis Viruses," *J. Virol.* 71:5982-5989, 1997, Copy Enclosed.

Kuo et al., "Effect of Mutations in the Gene-Start and Gene-End Sequence Motifs on Transcription of Monocistronic and Dicistronic Minigenomes of Respiratory Syncytial Virus," *J. Virol.* 70:6892-6901, 1996, Copy Enclosed.

Kurotani et al., "Sendai Virus C Proteins are Categorically Nonessential Gene Products but Silencing Their Expression Severely Impairs Viral Replication and Pathogenesis," *Gene to Cells*. 3:111-124, 1998, Copy Enclosed.

Lotorre et al., "The Various Sendai Virus C Proteins Are Not Functionally Equivalent and Exert both Positive and Negative Effects on Viral FNA Accumulation During the Course of Infection," *J. Virol.* 72:5984-5993, 1998, Copy Enclosed.

Lawson et al., "Recombinant Vesicular Stomatitis Viruses from DNA," *Proc. Natl. Acad. Sci. USA* 92:4477-4481, 1995.

Matsuoka et al., "The P Gene of Human Parainfluenza Virus Type 1 Encodes P and C Proteins but not a Cysteine-Rich V Protein," *J. Virol.* 65:3406-3410, 1991, Copy Enclosed.

Mebatsion et al., "Highly Stable Expression of a Foreign Gene from Rabies Virus Vectors," *Proc. Natl. Acad. Sci. U S A* 93:7310-7314, 1996, Copy Enclosed.

Moriya et al., "Large Quantity Production with Extreme Convenience of Human SDF-1α by a Sendai Virus Vector," *FEBS Lett.* 425:105-111, 1998, Copy Enclosed.

Murphy et al., "Current Approaches to the Development of Vaccines Effective Against Parainfluenza and Respiratory Syncytial Viruses," *Virus Res* 11:1-15, 1988, Copy Enclosed.

Murphy et al., "Enhanced Pulmonary Histopathology Is Observed In Cotton Rats Immunized With Formalin-Inactivated Respiratory Syncytial Virus (RSV) Or Purified F Glycoprotein And Challenged With RSV 3-6 Months After Immunization," *Vaccine* 8:497-502, 1990.

Palese et al., "Negative-Strand RNA Viruses: Genetic Engineering and Applications," *Proc. Natl. Acad. Sci. USA* 93:11354-11358, 1996.

Peeters et al., "Rescue of Newcastle Disease Virus from Cloned cDNA: Evidence that Cleavability of the Fusion Protein is a Major Determinant for Virulence," *J. Virol.* 73:5001-5009, 1999, Copy Enclosed.

Pelet et al., "The P Gene of Bovine Parainfluenza Virus 3 Expresses all Three Reading Frames from a Single mRNA Editing Site," *EMBO J* 10:443-448, 1991.

Radecke et al., "Rescue of Measles Viruses from Cloned DNA," *EMBO J.* 14:5773-5784, 1995.

Ray et al., "Human Parainfluenza virus Induces a Type-Specific Protective Immune Response," *J. Infect. Dis.* 162:746, 1990.

Ray et al., "Temperature-Sensitive Phenotype of the Human Parainfluenza Virus Type 3 Candidate Vaccine Strain (cp45) Correlates with a Defect in the L Gene," *J. Virol.* 70:580-584, 1996.

Roberts et al., "Attenuated Vesicular Stomatitis Viruses as Vaccine Vectors," *J. Virol.* 73:3723-3732, 1999, Copy Enclosed.

Roberts et al., "Vaccination with a Recombinant Vesicular Stomatitis Virus Expressing an Influenza Virus Hamagglutinin Provides Complete Protection from Influenza Virus Challenge," *J. Virol.* 72:4704-4711, 1998, Copy Enclosed.

Roberts et al., "Recovery of Negative-Strand RNA Viruses from Plasmid DNAs: A Positive Approach Revitalizes a Negative Field," *Virology* 247:1-6, 1998, Copy Enclosed.

Sakaguchi et al., "Expression of the HN, F, NP and M Proteins of Sendai Virus By Recombinant Vaccinia Viruses and Their Contribution to Protective Immunity Against Sendai Virus Infections in Mice," *J. Gen. Virol.* 74:479-484, 1993.

Sakai et al., "Accommodation Of Foreign Genes Into The Sendai Virus Genome: Sizes Of Inserted Genes And Viral Replication," *FEBS Letters* 456:221-226, 1999, Copy Enclosed.

Sanchez et al., "Cloning and Gene Assignment of mRNAs of Human Parainfluenza Virus 3," *Virology* 147:177-186, 1985, Copy Enclosed.

Schnell et al., "Infectious Rabies Viruses from Cloned cDNA," *EMBO J.* 13:4195-4203, 1994.

Schnell et al., "The Minimal Conserved Transcription Stop-Start Signal Promotes Stable Expression of a Foreign Gene in Vesicular Stomatitis Virus," *J. Virol.* 70:2318-2323, 1996, Copy Enclosed.

Schell et al., "Foreign Glycoproteins Expressed from Recombinant Vesicular Stomatitis Viruses are Incorporated Efficiently into Virus Particles," *Proc. Natl. Acad. Sci. USA* 93:11359-11365, 1996, Copy Enclosed.

Schnell et al., "Construction of a Novel Virus that Targets HIV-1-Infected Cells and Controls HIV-1 Infection," *Cell* 90:849-857, 1997, Copy Enclosed.

Singh et al., "A Recombinant Measles Virus Expressing Biologically Active Human Interleukin-12," *J. Gen. Virol.* 80:101-106, 1999, Copy Enclosed.

Singh et al., "A Recombinant Measles Virus expressing Hepatitis B Virus Surface Antigen Induces Humoral Immune Responses in Genetically Modified Mice," *J. Virol.* 73:4823-4828, 1999, Copy Enclosed.

Skiadopoulos et al., "Three Amino Acid Substitutions in the L Protein of the Human Parainfluenza Virus Type 3 cp45 Live Attenuated Vaccine Candidate Contribute to Its Temperature-Sensitive and Attenuation Phenotypes," *J. Virol* 72:1762-1768, 1998.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine," *J. Virol.* 73:1374-1381, 1999, Copy Enclosed.

Skiadopoulos et al., "Generation of a Parainfluenza Virus Type 1 Vaccine Candidate by Replacing the HN and F Glycoproteins of the Live-Attenuated PIV3 cp45 Vaccine Virus with Their PIV1 Counterparts," *Vaccine* 18:503-510, 1999, Copy Enclosed.

Spielhofer et al., "Chimeric Measles Viruses with a Foreign Envelope," *J. Virol.* 72:2150-2159, 1998, Copy Enclosed.

Spriggs et al., "Sequence Analysis of the P and C Protein Genes of Human Parainfluenza Virus Type 3: Patterns of Amino Acid Sequence Homology Among Paramyxovirus Proteins," *J. Gen. Virol.* 67:2705-2719, 1986.

Stokes et al., "The Complete Nucleotide Sequence of the JS Strain of Human Parainfluenza Virus Type 3: Comparison with the Wash/47885/57 Prototype Strain," *Virus Res.* 25:91-103, 1992.

Stokes et al., "The Complete Nucleotide Sequence of Two Cold-Adapted, Temperature-Sensitive Attenuated Mutant Vaccine Viruses (cp12 and cp45) Derived from the JS Strain and Human Parainfluenza Virus Type 3 (PIV3)," *Virus Res.* 30:43-52, 1993.

Tanabayashi, K. and Compans, R.W., "Functional Interaction of Paramyxovirus Glycoproteins: Identification of a Domain in Sendai Virus HN Which Promotes Cell Fusion," *J. Virol.* 70:6112-6118, 1996.

Tao et al., "Recovery of a Fully Viable Chimeric Human Parainfluenza Virus (PIV) Type 3 in Which the Hemagglutinin-Neuraminidase and Fusion Glycoproteins Have Been Replaced by Those of PIV Type 1," *J. Virol.* 72:2955-2961, 1998.

Tao et al., "A Live Attenuated Recombinant Chimeric Parainfluenza Virus (PIV) Candidate Vaccine Containing the Hemagglutinin-Neuraminidase and Fusion Glycoproteins of PIV1 and the Remaining Proteins from PIV3 Induces Resistance to PIV1 Even in Animals Immune to PIV3" *Vaccine* 17:1101-1108, 1999, Copy Enclosed.

van Wyke Coelingh et al., "Antigenic Variation in the Hemagglutinin-Neuraminidase Protein of Human Parainfluenza Type 3 Virus," *Virology* 143:569-582, 1985.

van Wyke Coelingh et al., "Antigenic and Structural Properties of the Hemagglutinin-Neuraminidase Glycoprotein of Human Parainfluenza Virus Type 3: Sequence Analysis of Variants Selected with Monoclonal Antibodies Which Inhibit Infectivity, Hemagglutination, and Neuraminidase Activities," *J. Virol.* 61:1473-1477, 1987.

Vidal et al., "Editing of the Sendai Virus P/C mRNA by G Insertion Occurs during mRNA Synthesis via a Virus-Encoded Activity," *J. Virol.* 64:239-246, 1990, Copy Enclosed.

Wathen et al., "Characterization of a Novel Human Respiratory Syncytial Virus Chimeric FG Glycoprotein Expressed Using a Baculovirus Vector," *J. Gen Virol.* 70:2625-2635, 1989, Copy Enclosed.

Whelan et al., "Efficient Recovery Of Infectious Vesicular Stomatitis Virus Entirely From cDNA Clones," *Proc. Natl. Acad. Sci. USA* 92:8388-8392, 1995.

Whitehead et al., "A Single Nucleotide Substitution in the Transcription Start Signal of the M2 Gene of Respiratory Syncytial Virus Vaccine Candidate cpts248/404 is the Major Determinant of the Temperature-Sensitive and Attenuation Phenotypes," *Virology* 247:232-239, 1998a, Copy Enclosed.

Whitehead et al., "Recombinant Respiratory Syncytial Virus (RSV) Bearing a Set of Mutations from cold-Passaged RSV is Attenuated in Chimpanzees," *J. Virol.* 72:4467-4471, 1998b, Copy Enclosed.

Whitehead et al., "Recombinant Respiratory Syncytial Virus Bearing a Deletion of Either the NS2 or SH Gene is Attenuated in Chimpanzees," *J. Virol.* 73:3438-3442, 1999, Copy Enclosed.

Yu et al., "Sendai Virus-Based Expression of HIV-1 gp120: Reinforcement by the V(-) Version," *Genes to Cells* 2:457-466, 1997, Copy Enclosed.

Bailly et al., "A Recombinant Human Parainfluenza Virus Type 3 (PIV3) in Which the Nucleocapsid N Protein Has Been Replaced by That of Bovine PIV3 Is Attenuated in Primates," *J. Virol.* 74(7):3188-3195, 2000.

Bukreyev et al., "Interferon γ expressed by a recombinant respiratory syncytial virus attenuates virus replication in mice without compromising immunogenicity," *Proc. Natl. Acad. Sci. USA* 96:2367-2372, 1999.

Tao, "A live attenuated chimeric recombinant parainfluenza virus (PIV) encoding the internal proteins of PIV type 3 and the surface glycoproteins of PIV type 1 induces complete resistance to PIV1 challenge and partial resistance of PIV3 challenge," *Vaccine* 17:1100-1108, 1999.

van Wyke Coelingh et al., "Attenuation of Bovine Parainfluenza Virus Type 3 in Nonhuman Primates and Its Ability to Confer Immunity to Human Parainfluenza Virus Type 3 Challenge," *J. Infect. Dis.* 157(4):655-661, 1988.

* cited by examiner

Fig. 1A
Measles HA insert for N-P and P-M junctions

FIG. 1B

Measles HA insert for the HN-L junction 8828 8733
                        8802         Gene End  IG  Gene Start
       Stu I
       AGGCCTAAAAGGGAAATATAAAAAACTTAGGAGTAAAGTTACGCAATCCAACTCTACTCATATAATTGAGGAAGGACCCAATAGACAAATCCAAATT- CGAG [ HA TAG ] TCATAATTAACCATAATATGCATCAATCTATCTATAATACAAGTATATGATAAGTAATCAGCAATCAGACAATAGGCCT
            |        |                                                                              | Stu I
          6803     8878                                                                                8897 rPIV3 (encoded by p3/7(131)2G-Stu)
       leader                                          Stu I(8800)   Sph I(13117)              trailer
       |────[ N ]──[ P/C ]──[ M ]──[ F ]──[ HN ]──[            L            ]──|
       1                                                                                       15462 rPIV3(HA HN-L)
       leader                                      Stu I(8800)   Stu I(10828)                  trailer
       |────[ N ]──[ P/C ]──[ M ]──[ F ]──[ HN ]──[ HA ]──[        L         ]──|
       1                                                                                       17490

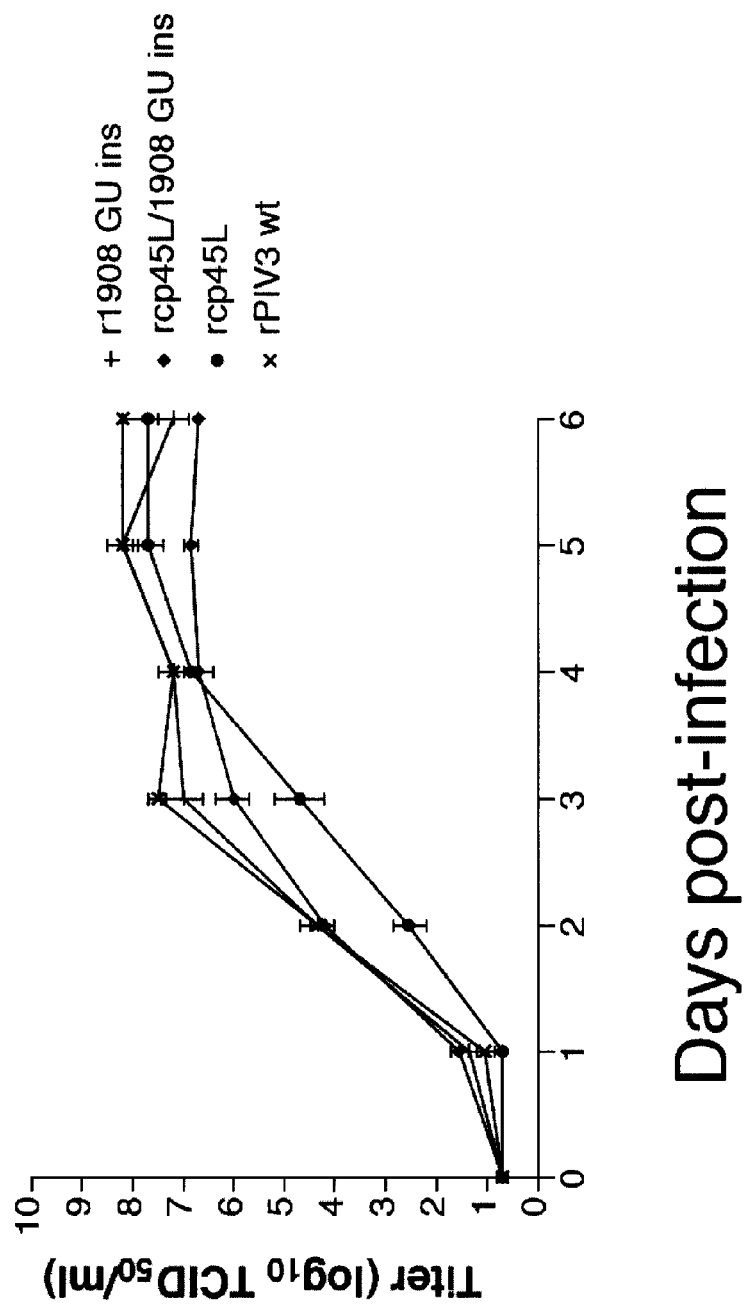

SEQUENCE LISTING

<160> NUMBER OF SEQ ID NOS: 30

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 1
cttaagaata tacaaataag aaaaacttag gattaaagag cg                          42

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 2
gatccaacaa agaaacgaca ccgaacaaac cttaag                                 36

<210> SEQ ID NO 3
<211> LENGTH: 101

```
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 3
aggcctaaaa gggaaatata aaaaacttag gagtaaagtt acgcaatcca actctactca      60
tataattgag gaaggaccca atagacaaat ccaaattcga g                        101

<210> SEQ ID NO 4
<211> LENGTH: 79
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 4
tcataattaa ccataatatg catcaatcta tctataatac aagtatatga taagtaatca      60
gcaatcagac aataggcct                                                  79

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 5
aggaaaaggg aaatataaaa acttaggagt aaagttacgc gtgttaactt cgaagagctc      60
cct                                                                   63

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 6
aggaaaaggg aacgcgtgtt aacttcgaag agctccct                             38

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 7 ctaaat                                                                 6

<210> SEQ ID NO 8
<211> LENGTH: 6
<212> TYPE: DNA
<213> ORGANISM: Artificial Sequence
<220> FEATURE:
```

```
<223> OTHER INFORMATION: Description of Artificial Sequence: Nucleotide
      insert to conform inserted sequence to rule of
      six.

<400> SEQUENCE: 8 cttaag                                                              6

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 9 tcaatc                                                              6

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 10
acaacgagac cggataaatg ccttctac                                     28

<210> SEQ ID NO 11
<211> LENGTH: 67
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 11
attattgctt aaggtttgtt cggtgtcgtt tctttgttgg atcctatctg cgattggttc   60
catcttc                                                            67

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 12 agacaa                                                              6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 13 aggcct                                                              6
```

<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 14
gacaataggc ctaaaaggga aatataaaaa acttaggagt aaagttacgc aatcc         55

<210> SEQ ID NO 15
<211> LENGTH: 68
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 15
gtagaacgcg tttatccggt ctcgttgtgg tgacatctcg aatttggatt tgtctattgg    60
gtccttcc                                                             68

<210> SEQ ID NO 16
<211> LENGTH: 68
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 16
gtagaacgcg tttatccggt ctcgttgtgg tgacatctcg aatttggatt tgtctattgg    60
gtccttcc                                                             68

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 17
ccatgtaatt gaatccccca acactagc                                       28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 18
cggataaacg cgttctacaa agataacc                                       28

<210> SEQ ID NO 19
<211> LENGTH: 28
<212> TYPE: DNA

<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 19
cggataaacg cgttctacaa agataacc                                       28

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 20
gggccatgga agattacagc aat                                            23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 21
caataagctt aaagcattag ttccc                                          25

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 22
gcgatgggcc cgaggaagga cccaatagac a                                   31

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 23
cccgggtcct gatttcccga gcacgctttg                                     30

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Nucleotide
      insert to conform inserted sequence to rule of
      six.

<400> SEQUENCE: 24
agtggctaat tgcattgcat ccacat                                         26

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 25
gccgtctgca tggtgaatag caat                                            24

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 26
cgcggcaggc ctg                                                        13

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 27
cgcggcgagg cctg                                                       14

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 28
cgcgaggcct ccgcg                                                      15

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of
    six.

<400> SEQUENCE: 29
cgcgccgcgg aggcct                                                     16

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Nucleotide
    insert to conform inserted sequence to rule of -continued six.

<400> SEQUENCE: 30
cgcgcccgcg gaggcct                                                                         17

USE OF RECOMBINANT LIVE-ATTENUATED PARAINFLUENZA VIRUS (PIV) AS A VECTOR TO PROTECT AGAINST DISEASE CAUSED BY PIV AND RESPIRATORY SYNCYTIAL VIRUS (RSV)

RELATED APPLICATIONS

The present application is a continuation-in-part application of, and claims the benefit under Title 35 of, U.S. patent application Ser. No. 09/083,793, filed May 22, 1998 which is a continuation-in-part of U.S. Provisional Application No. 60/047,575, filed May 23, 1997, now abandoned, and U.S. Provisional Application No. 60/059,385, filed Sep. 19, 1997, now abandoned. The disclosures of each of the foregoing priority applications are incorporated herein by reference in their entirety for all purposes.

BACKGROUND OF THE INVENTION

Human parainfluenza virus type 3 (HPIV3) is a common cause of serious lower respiratory tract infection in infants and children less than one year of age. It is second only to respiratory syncytial virus (RSV) as a leading cause of hospitalization for viral lower respiratory tract disease in this age group (Collins et al., p. 1205–1243. In B. N. Fields (Knipe et al., eds), Fields Virology, 3rd ed, vol. 1. Lippincott-Raven Publishers, Philadelphia, 1996; Crowe et al., *Vaccine* 13:415–421, 1995; Marx et al., *J. Infect. Dis.* 176:1423–1427, 1997). Infections by this virus results in substantial morbidity in children less than 3 years of age. HPIV1 and HPIV2 are the principal etiologic agents of laryngotracheobronchitis (croup) and also can cause severe pneumonia and bronchiolitis (Collins et al., 3rd ed. In "*Fields Virology,*" B. N. Fields, D. M. Knipe, P. M. Howley, R. M. Chanock, J. L. Melnick, T. P. Monath, B. Roizman, and S. E. Straus, Eds., Vol. 1, pp. 1205–1243. Lippincott-Raven Publishers, Philadelphia, 1996). In a long term study over a 20-year period, HPIV1, HPIV2, and HPIV3 were identified as etiologic agents for 6.0, 3.2, and 11.5%, respectively, of hospitalizations for respiratory tract disease accounting in total for 18% of the hospitalizations, and, for this reason, there is a need for an effective vaccine (Murphy et al., *Virus Res* 11, 1–15, 1988). The parainfluenza viruses have also been identified in a significant proportion of cases of virally-induced middle ear effusions in children with otitis media (Heikkinen et al., *N. Engl. J. Med.* 340:260–4, 1999). Thus, there is a need to produce a vaccine against these viruses that can prevent the serious lower respiratory tract disease and the otitis media that accompanies these HPIV infections. HPIV1, HPIV2, and HPIV3 are distinct serotypes which do not elicit significant cross-protective immunity.

Despite considerable efforts to develop effective vaccine therapies against HPIV, no approved vaccine agents have yet been achieved for any HPIV serotype, nor for ameliorating HPIV related illnesses. To date, only two live attenuated PIV vaccine candidates have received particular attention. One of these candidates is a bovine PIV (BPIV3) strain that is antigenically related to HPIV3 and which has been shown to protect animals against HPIV3. BPIV3 is attenuated, genetically stable and immunogenic in human infants and children (Karron et al., *J. Inf. Dis.* 171:1107–14 (1995a); Karron et al., *J. Inf. Dis.* 172:1445–1450, (1995b)). A second PIV3 vaccine candidate, JS cp45, is a cold-adapted mutant of the JS wildtype (wt) strain of HPIV3 (Karron et al., (1995b), supra; Belshe et al., *J. Med. Virol.* 10:235–42 (1982)). This live, attenuated, cold-passaged (cp) PIV3 vaccine candidate exhibits temperature-sensitive (ts), cold-adaptation (ca), and attenuation (att) phenotypes which are stable after viral replication in vivo. The cp45 virus is protective against human PIV3 challenge in experimental animals and is attenuated, genetically stable, and immunogenic in seronegative human infants and children (Hall et al., *Virus Res.* 22:173–184 (1992); Karron et al., (1995b), supra The most promising prospects to date are live attenuated vaccine viruses since these have been shown to be efficacious in non-human primates even in the presence of passively transferred antibodies, an experimental situation that simulates that present in the very young infant who possesses maternally acquired antibodies (Crowe et al., *Vaccine* 13:847–855, 1995; Durbin et al., *J Infect Dis* 179:1345–1351, 1999). Two live attenuated PIV3 vaccine candidates, a temperature-sensitive (ts) derivative of the wild type PIV3 JS strain (designated P1V3cp45) and a bovine PIV3 (BPIV3) strain, are undergoing clinical evaluation (Karron et al., *Pediatr Infect Dis J* 15:650–654, 1996; Karron et al., *J Infect Dis* 171:1107–1114, 1995a; Karron et al., *J Infect Dis* 172, 1445–1450, 1995b). The live attenuated P1V3cp45 vaccine candidate was derived from the JS strain of HPIV3 via serial passage in cell culture at low temperature and has been found to be protective against HPIV3 challenge in experimental animals and to be satisfactorily attenuated, genetically stable, and immunogenic in seronegative human infants and children (Belshe et al, *J. Med. Virol.* 10:235–242, 1982; Belshe et al., *Infect Immun* 37:160–5, 1982; Clements et al., *J. Clin. Microbiol.* 29:1175–82, 1991; Crookshanks et al., *J. Med. Virol.* 13:243–9, 1984; Hall et al., *Virus Res.* 22:173–184, 1992; Karron et al., *J. Infect. Dis.* 172, 1445–1450, 1995b). Because these PIV3 candidate vaccine viruses are biologically derived, there is no proven methods for adjusting the level of attenuation should this be found necessary from ongoing clinical trials.

To facilitate development of PIV vaccine candidates, recombinant DNA technology has recently made it possible to recover infectious negative-stranded RNA viruses from cDNA (for reviews, see Conzelmann, *J. Gen. Virol.* 77:381–89 (1996); Palese et al., Proc. Natl. Acad. Sci. U.S.A. 93:11354–58, (1996)). In this context, recombinant rescue has been reported for infectious respiratory syncytial virus (RSV), rabies virus (RaV), simian virus 5 (SV5), rinderpest virus, Newcastle disease virus (NDV), vesicular stomatitis virus (VSV), measles virus (MeV), and Sendai virus (SeV) from cDNA-encoded antigenomic RNA in the presence of essential viral proteins (see, e.g., Garcin et al., *EMBO J.* 14:6087–6094 (1995); Lawson et al., Proc. Natl. Acad. Sci. U.S.A. 92:4477–81 (1995); Radecke et al., *EMBO J.* 14:5773–5784 (1995); Schnell et al., *EMBO J.* 13:4195–203 (1994); Whelan et al., *Proc. Natl. Acad. Sci. U.S.A.* 92:8388–92 (1995); Hoffman et al., *J. Virol.* 71:4272–4277 (1997); Kato et al., *Genes to Cells* 1:569–579 (1996), Roberts et al., *Virology* 247(1), 1–6 (1998); Baron et al., *J. Virol.* 71:1265–1271 (1997); International Publication No. WO 97/06270; Collins et al., *Proc. Natl. Acad. Sci. USA* 92:11563–11567 (1995); U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); U.S. patent application entitled PRODUCTION OF ATTENUATED CHIMERIC RESPIRATORY SYNCYTIAL VIRUS VACCINES FROM CLONED NUCLEOTIDE SEQUENCES, filed on Apr. 13, 1999 and identified by Ser. No. 09/291,894; U.S. Provisional Patent Application Ser. No. 60/129,006, filed Apr. 13, 1999; U.S. Provisional Patent Application Ser. No. 60/143,132, filed by Bucholz et al. on Jul. 9, 1999; Juhasz et al., *J. Virol.* 71(8):5814–5819 (1997); He et al. *Virology* 237:249–260 (1997); Peters et al. *J. Virol.* 73:5001–5009, 1999; Baron et al. *J. Virol.* 71:1265–1271 (1997); Whitehead et al., *Virology* 247(2):232–9 (1998a); Whitehead et al., *J. Virol.* 72(5): 4467–4471 (1998b); Jin et al. *Virology* 251:206–214 (1998); Bucholz et al. *J. Virol.* 73:251–259 (1999); and Whitehead et al., *J. Virol.* 73:(4)3438–3442 (1999), each incorporated herein by reference in its entirety for all purposes).

In more specific regard to the instant invention, a method for producing HPIV with a wt phenotype from cDNA was recently developed for recovery of infectious, recombinant HPIV3 JS strain (see, e.g., Durbin et al., *Virology* 235: 323–332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, these disclosures allow for genetic manipulation of viral cDNA cones to determine the genetic basis of phenotypic changes in biological mutants, e.g., which mutations in the HPIV3 cp45 virus specify its ts, ca and att phenotypes, and which gene(s) or genome segment(s) of BPIV3 specify its attenuation phenotype. Additionally, these and related disclosures render it feasible to construct novel PIV vaccine candidates having a wide range of different mutations and to evaluate their level of attenuation, immunogenicity and phenotypic stability (see also, U.S. Provisional Patent Application Ser. No. 60/143,134, filed by Bailey et al. on Jul. 9, 1999; and U.S. patent application Ser. No. 09/350,821, filed by Durbin et al. on Jul. 9, 1999, each incorporated herein by reference).

Thus, infectious wild type recombinant PIV3, (r)PIV3, as well as a number of ts derivatives, have now been recovered from cDNA, and reverse genetics systems have been used to generate infectious virus bearing defined attenuating mutations and to study the genetic basis of attenuation of existing vaccine viruses. For example, the three amino acid substitutions found in the L gene of cp45, singularly or in combination, have been found to specify the ts and attenuation phenotypes. Additional ts and attenuating mutations are present in other regions of the P1V3cp45. In addition a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3–1.cp45L (Skiadopoulos et al., *J Virol* 72:1762–8, 1998; Tao et al., *J Virol* 72:2955–2961, 1998; Tao et al., *Vaccine* 17:1100–1108, 1999, incorporated herein by reference). rPIV3-1.cp45L was attenuated in hamsters and induced a high level of resistance to challenge with PIV1. Yet another recombinant chimeric virus, designated rPIV3-1.cp45, has been produced that contains 12 of the 15 cp45 mutations, i.e., excluding the mutations that occur in HN and F. This recombinant vaccine candidate is highly attenuated in the upper and lower respiratory tract of hamsters and induces a high level of protection against HPIV1 infection (Skiadopoulos et al., *Vaccine* In press, 18:503–510, 1999).

Recently, a number of studies have focused on the possible use of viral vectors to express foreign antigens toward the goal of developing vaccines against a pathogen for which other vaccine alternatives are not proved successful. In this context, a number of reports suggest that foreign genes may be successfully inserted into a recombinant negative strand RNA virus genome or antigenome with varying effects (Bukreyev et al., *J. Virol.* 70:6634–41, 1996; Bukreyev et al., *Proc. Natl. Acad. Sci. USA* 96:2367–72, 1999; Finke et al. *J. Virol.* 71:7281–8, 1997; Hasan et al., *J. Gen. Virol.* 78:2813–20, 1997; He et al., *Virology* 237: 249–60, 1997; Jin et al., *Virology* 251:206–14, 1998; Johnson et al., *J. Virol.* 71:5060–8, 1997; Kahn et al., *Virology* 254:81–91, 1999; Kretzschmar et al., *J. Virol.* 71:5982–9, 1997; Mebatsion et al., *Proc. Natl. Acad. Sci. USA* 93:7310–4, 1996; Moriya et al., *FEBS Lett.* 425: 105–11, 1998; Roberts et al., *J. Virol.* 73:3723–32, 1999; Roberts et al., *J. Virol.* 72:4704–11, 1998; Roberts et al., *Virology* 247:1–6, 1998; Sakai et al., *FEBS Letter* 456: 221–226, 1999; Schnell et al., *Proc. Natl. Acad. Sci. USA* 93:11359–65, 1996a; Schnell et al., *J. Virol.* 70:2318–23, 1996b; Schnell et al., *Cell* 90:849–57, 1997; Singh et al., *J. Gen. Virol.* 80:101–6, 1999; Singh et al., *J. Virol.* 73:4823–8, 1999; Spielhofer et al., *J. Virol.* 72, 2150–9, 1998; Yu et al., *Genes to Cells* 2:457–66 et al., 1999; U.S. Provisional Patent Application Ser. No. 60/143,425, filed on Jul. 13, 1999, each incorporated herein by reference). When inserted into the viral genome under the control of viral transcription gene-start and gene-end signals, the foreign gene may be transcribed as a separate mRNA and yield significant protein expression. Surprisingly, in some cases foreign sequence has been reported to be stable and capable of expressing functional protein during numerous passages in vitro.

However, to successfully develop vectors for vaccine use, it is insufficient to simply demonstrate a high, stable level of protein expression. For example, this has been possible since the early-to-mid 1980s with recombinant vaccinia viruses and adenoviruses, and yet these vectors have proven to be disappointments in the development of vaccines for human use. Similarly, most nonsegmented negative strand viruses which have been developed as vectors do not possess properties or immunization strategies amenable for human use. Examples in this context include vesicular stomatitis virus, an ungulate pathogen with no history of administration to humans except for a few laboratory accidents; Sendai virus, a mouse pathogen with no history of administration to humans; simian virus 5, a canine pathogen with no history of administration to humans; and an attenuated strain of measles virus which must be administered systemically and would be neutralized by measles-specific antibodies present in nearly all humans due to maternal antibodies and widespread use of a licensed vaccine. Furthermore, some of these prior vector candidates have adverse effects, such as immunosupression, which are directly inconsistent with their use as vectors. Thus, one must identify vectors whose growth characteristics, tropisms, and other biological properties make them appropriate as vectors for human use. It is further necessary to develop a viable vaccination strategy, including an immunogenic and efficacious route of administration.

Among a host of human pathogens for which a vector-based vaccine approach may be desirable is the measles virus. A live attenuated vaccine has been available for more than three decades and has been largely successful in eradicating measles disease in the United States. However, the World Health Organization estimates that more than 45 million cases of measles still occur annually, particularly in developing countries, and the virus contributes to approximately one million deaths per year Measles virus is a member of the *Morbillivirus* genus of the Paramyxoviridae family (Griffin et al., In "Fields Virology", B. N. Fields, D. M. Knipe, P. M. Howley, R. M. Chanock, J. L. Melnick, T. P. Monath, B. Roizman, and S.

E. Straus, Eds., Vol. 1, pp. 1267–1312. Lippincott-Raven Publishers, Philadelphia, 1996). It is one of the most contagious infectious agents known to man and is transmitted from person to person via the respiratory route (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). The measles virus has a complex pathogenesis, involving replication in both the respiratory tract and various systemic sites (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996).

Although both mucosal IgA and serum IgG measles virus-specific antibodies can participate in the control of measles virus, the absence of measles virus disease in very young infants possessing maternally-acquired measles virus-specific antibodies identifies serum antibodies as a major mediator of resistance to disease (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). The two measles virus glycoproteins, the hemagglutinin (HA) and fusion (F) proteins, are the major neutralization and protective antigens (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996).

The currently available live attenuated measles vaccine is administered by a parenteral route (Griffin et al., In "Fields Virology" (B. N. Fields, D. M. Knipe, P. M. Howley, R. M. Chanock, J. L. Melnick, T. P. Monath, B. Roizinan, and S. E. Straus, Eds.), Vol. 1, pp. 1267–1312. Lippincott-Raven Publishers, Philadelphia, 1996). Both the wild type measles virus and the vaccine virus are very readily neutralized by antibodies, and the measles virus vaccine is rendered non-infectious by even very low levels of maternally-acquired measles virus-specific neutralizing antibodies (Halsey et al., N. Engl. J. Med. 313:544–9, 1985; Osterhaus et al., Vaccine 16:1479–81, 1998). Thus, the vaccine virus is not given until the passively-acquired maternal antibodies have decreased to undetectable levels. In the United States, measles virus vaccine is not given until 12 to 15 months of age, a time when almost all children are readily infected with the measles virus vaccine. In the developing world, measles virus continues to have a high mortality rate, especially in children within the latter half of the first year of life (Gellin et al., J. Infect. Dis. 170, S3–14, 1994; Taylor et al., Am. J. Epidemiol. 127:788–94, 1988). This occurs because the measles virus, which is highly prevalent in these regions, is able to infect that subset of infants in whom maternally-acquired measles virus-specific antibody levels have decreased to a non-protective level. Therefore, there is a need for a measles virus vaccine that is able to induce a protective immune response even in the presence of measles virus neutralizing antibodies with the goal of eliminating measles virus disease occurring within the first year of life as well as that which occurs thereafter. Given this need, there have been numerous attempts to develop an immunization strategy to protect infants in the latter half of the first year of life against measles virus, but none of these strategies has been effective to date.

The first strategy for developing an early measles vaccine involved administration of the licensed live attenuated measles virus vaccine to infants about six months of age by one of the following two methods (Cutts et al., Biologicals 25, 323–38, 1997). In one general protocol, the live attenuated measles virus was administered intranasally by drops (Black et al., New Eng. J. Med. 263, 165–169; 1960; Kok et al., Trans. R. Soc. Trop. Med. Hyg. 77:171–6, 1983; Simasathien et al., Vaccine 15:329–34, 1997) or into the lower respiratory tract by aerosol (Sabin et al., J. Infect. Dis. 152:1231–7, 1985), to initiate an infection of the respiratory tract. In a second protocol, the measles virus was given parenterally but at a higher dose than that employed for the current vaccine. The administration of vaccines that can replicate on mucosal surfaces has been successfully achieved in early infancy for both live attenuated poliovirus and rotavirus vaccines (Melnick et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 655–712. 2 vols. Lippencott-Raven Publishers, Philadelphia, 1996; Perez-Schael et al., N. Engl. J. Med. 337, 1181–7, 1997), presumably because passively-acquired IgG antibodies have less access to mucosal surfaces than they do to systemic sites of viral replication. In this situation, the live attenuated poliovirus vaccine viruses are able to infect the mucosal surface of the gastrointestinal tract or the respiratory tract of young infants, including those with maternal antibodies, resulting in the induction of a protective immune response.

Therefore, a plausible method is to immunize via the respiratory tract of the young infant with the live attenuated measles virus vaccine, since this is the natural route of infection with the measles virus. However, the live attenuated measles virus that is infectious by the parenteral route was inconsistently infectious by the intranasal route (Black et al., New Eng. J. Med. 263:165–169, 1960; Cutts et al., Biologicals 25, 323–38, 1997; Kok et al., Trans. R. Soc. Trop. Med. Hyg. 77:171–6, 1983; Simasathien et al., Vaccine 15:329–34, 1997), and this decreased infectivity was especially apparent for the Schwartz stain of measles virus vaccine which is the current vaccine strain. Presumably, during the attenuation of this virus by passage in tissue culture cells of avian origin, the virus lost a significant amount of infectivity for the upper respiratory tract of humans. Indeed, a hallmark of measles virus biology is that the virus undergoes rapid changes in biological properties when grown in vitro. Since this relatively simple route of immunization was not successful, a second approach was tried involving administration of the live virus vaccine by aerosol into the lower respiratory tract (Cutts et al., Biologicals 25, 323–38, 1997; Sabin et al., J. Infect. Dis. 152: 1231–7, 1985).

Infection of young infants by aerosol administration of measles virus vaccine was accomplished in highly controlled experimental studies, but it has not been possible to reproducibly deliver a live attenuated measles virus vaccine in field settings by aerosol to the young uncooperative infant (Cutts et al., Biologicals 25, 323–38, 1997). In another attempt to immunize six-month old infants, the measles vaccine virus was administered parenterally at a 10- to 100-fold increased dose (Markowitz et al., N. Engl. J. Med. 322:580–7, 1990). Although high-titer live measles vaccination improved seroconversion in infants 4–6 months of age, there was an associated increase in mortality in the high-titer vaccine recipients later in infancy (Gellin et al., J. Infect. Dis. 170:S3–14, 1994; Holt et al., J. Infect. Dis.

168:1087–96, 1993; Markowitz et al., *N. Engl. J. Med.* 322:580–7, 1990) and this approach to immunization has been abandoned.

A second strategy previously explored for a measles virus vaccine was the use of an inactivated measles virus vaccine, specifically, a formalin inactivated whole measles virus or a subunit virus vaccine prepared from measles virus (Griffin et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1267–1312. Lippincott-Raven Publishers, Philadelphia, 1996). However, the clinical use of the vaccines in the 1960's revealed a very serious complication, namely, that the inactivated virus vaccines potentiated disease rather than prevented it (Fulginiti et al., *JAMA* 202:1075–80, 1967). This was first observed with formalin-inactivated measles virus vaccine (Fulginiti et al., *JAMA* 202:1075–80, 1967). Initially, this vaccine prevented measles, but after several years vaccinees lost their resistance to infection. When subsequently infected with naturally circulating measles virus, the vaccinees developed an atypical illness with accentuated systemic symptoms and pneumonia (Fulginiti et al., *JAMA* 202:1075–80, 1967; Nader et al., *J. Pediatr.* 72:22–8, 1968; Rauh et al., *Am. J. Dis. Child* 109:232–7, 1965). Retrospective analysis showed that formalin inactivation destroyed the ability of the measles fusion (F) protein to induce hemolysis-inhibiting antibodies, but it did not destroy the ability of the HA (hemagglutinin or attachment) protein to induce neutralizing antibodies (Norrby et al., *J. Infect. Dis.* 132:262–9, 1975; Norrby et al., *Infect. Immun.* 11:231–9, 1975). When the immunity induced by the HA protein had waned sufficiently to permit extensive infection with wild type measles virus, an altered and sometimes more severe disease was seen at the sites of measles virus replication (Bellanti, *Pediatrics* 48:715–29, 1971; Buser, *N. Engl. J. Med.* 277:250–1, 1967). This atypical disease is believed to be mediated in part by an altered cell-mediated immune response in which Th-2 cells were preferentially induced leading to heightened disease manifestations at the sites of viral replication (Polack et al., *Nat. Med.* 5:629–34, 1999). Because of this experience with nonliving measles virus vaccines and also because the immunogenicity of such parenterally-administered vaccines can be decreased by passively-transferred antibodies, there has been considerable reluctance to evaluate such vaccines in human infants. It should be noted that disease potentiation appears to be associated only with killed vaccines.

Yet another strategy that has been explored for developing a vaccine against measles for use in young infants has been the use of viral vectors to express a protective antigen of the measles virus (Drillien et al., *Proc. Natl. Acad. Sci. USA* 85:1252–6, 1988; Fooks et al., *J. Gen. Virol.* 79:1027–31, 1998; Schnell et al., *Proc. Natl. Acad. Sci. USA* 93:11359–65, 1996a; Taylor et al., *Virology* 187:321–8, 1992; Wild et al., *Vaccine* 8:441–2, 1990; Wild et al., *J. Gen. Virol.* 73:359–67, 1992). A variety of vectors have been explored including poxviruses such as the replication-competent vaccinia virus or the replication-defective modified vaccinia virus Ankara (MVA) stain. Replication-competent vaccinia recombinants expressing the F or HA glycoprotein of measles virus were efficacious in immunologically naive vaccinees. However, when they were administered parenterally in the presence of passive antibody against measles virus, their immunogenicity and protective efficacy was largely abrogated (Galletti et al., *Vaccine* 13, 197–201, 1995; Osterhaus et al., *Vaccine* 16:1479–81, 1998; Siegrist et al., *Vaccine* 16:1409–14, 1998; Siegrist et al., *Dev. Biol. Stand.* 95:133–9, 1998).

Replication-competent vaccinia recombinants expressing the protective antigens of RSV have also been shown to be ineffective in inducing a protective immune response when they are administered parenterally in the presence of passive antibody (Murphy et al., *J. Virol.* 62:3907–10, 1988a), but they readily protected such hosts when administered intranasally. Unfortunately, replication-competent vaccinia virus recombinants are not sufficiently attenuated for use in immunocompromised hosts such as persons with human immunodeficiency virus (HIV) infection (Fenner et al., World Health Organization, Geneva, 1988; Redfield et al., *N. Engl. J. Med.* 316, 673–676, 1987), and their administration by the intranasal route even to immunocompetent individuals would be problematic. Therefore they are not being pursued as vectors for use in human infants, some of whom could be infected with HIV.

The MVA vector, which was derived by more than 500 passages in chick embryo cells (Mayr et al., *Infection* 3:6–14, 1975; Meyer et al., *J. Gen. Virol.* 72:1031–1038, 1991), has also been evaluated as a potential vaccine vector for the protective antigens of several paramyxoviruses (Durbin et al., *J. Infect. Dis.* 179:1345–51, 1999a; Wyatt et al., *Vaccine* 14, 1451–1458, 1996). MVA is a highly attenuated host range mutant that replicates well in avian cells but not in most mammalian cells, including those obtained from monkeys and humans (Blanchard et al., *J. Gen. Virol.* 79:1159–1167, 1998; Carroll et al., *Virology* 238:198–211, 1997; Drexler et al., *J. Gen. Virol.* 79, 347–352, 1998; Sutter et al., *Proc. Natl. Acad. Sci. U.S.A.* 89:10847–10851, 1992). Avipox vaccine vectors, which have a host range restriction similar to that of MVA, also have been constructed that express measles virus protective antigens (Taylor et al., *Virology* 187, 321–8, 1992). MVA is non-pathogenic in immunocompromised hosts and has been administered to large numbers of humans without incident (Mayr et al., *Zentralbl Bakteriol [B]* 167, 375–90, 1978; Stickl et al., *Dtsch. Med. Wochenschr.* 99:2386–92, 1974; Werner et al., *Archives of Virology* 64, 247–256, 1980). Unfortunately, both the immunogenicity and efficacy of MVA expressing a paramyxovirus protective antigen were abrogated in passively-immunized rhesus monkeys whether delivered by a parenteral or a topical route (Durbin et al., *Virology* 235:323–332, 1999). The immunogenicity of DNA vaccines expressing measles virus protective antigens delivered parenterally was also decreased in passively-immunized hosts (Siegrist et al., *Dev. Biol. Stand.* 95:133–9, 1998). Replication-defective vectors expressing measles virus protective antigens are presently being evaluated, including adenovirus-measles virus HA recombinants (Fooks et al., *J. Gen. Virol.* 79:1027–31, 1998). In this context, MVA recombinants expressing parainfluenza virus antigens, unlike replication-competent vaccinia virus recombinants, lacked protective efficacy when given by a mucosal route to animals with passively-acquired antibodies, and it is unlikely that they, or the similar avipox vectors, can be used in infants with maternally-acquired measles virus antibodies.

Based on the reports summarized above, it appears unlikely that a replication-competent or replication-defective poxvirus vector, or a DNA vaccine, expressing a measles virus protective antigen will be satisfactorily immunogenic or efficacious in infants possessing passively-acquired maternal measles virus-specific antibodies.

A recently developed replication-competent virus vector expressing measles virus HA that replicates in the respiratory tract of animal hosts has been developed, namely, vesicular stomatitis virus (VSV), a rhabdovirus which naturally infects cattle but not humans (Roberts et al., *J. Virol.* 73:3723–32, 1999; Schnell et al., *Proc. Natl. Acad. Sci. USA* 93:11359–65. 1996a). Since VSV is an animal virus that can cause disease in humans, development of this recombinant for use in humans will require that a VSV backbone that is satisfactorily attenuated in human infants be first identified (Roberts et al., *J. Virol.* 73:3723–32, 1999), but such clinical studies have not been initiated.

Although there have been numerous advances toward development of effective vaccine agents against PIV and other pathogens, including measles, there remains a clear need in the art for additional tools and methods to engineer safe and effective vaccines to alleviate the serious health problems attributable to these pathogens, particularly among young infants. Among the remaining challenges in this context is the need for additional tools to generate suitably attenuated, immunogenic and genetically stable vaccine candidates for use in diverse clinical settings against one or more pathogens. To facilitate these goals, existing methods for identifying and incorporating attenuating mutations into recombinant vaccine strains and for developing vector-based vaccines and immunization methods must be expanded. Surprisingly, the present invention fulfills these needs and provides additional advantages as described herein below.

SUMMARY OF THE INVENTION

The present invention provides chimeric parainfluenza viruses (PIVs) that are infectious in humans and other mammals and are useful in various compositions to generate desired immune responses against one or more PIVs, or against a PIV and one or more additional pathogens in a host susceptible to infection therefrom. In preferred aspects, the invention provides novel methods for designing and producing attenuated, chimeric PIVs that are useful as vaccine agents for preventing and/or treating infection and related disease symptoms attributable to PIV and one or more additional pathogens. Included within these aspects of the invention are novel, isolated polynucleotide molecules and vectors incorporating such molecules that comprise a chimeric PIV genome or antigenome including a partial or complete PIV vector genome or antigenome combined or integrated with one or more heterologous genes or genome segments that encode single or multiple antigenic determinants of a heterologous pathogen or of multiple heterologous pathogens. Also provided within the invention are methods and compositions incorporating a chimeric PIV for prophylaxis and treatment of infection by both a selected PIV and one or more heterologous pathogens, e.g., a heterologous PIV or a non-PIV pathogen such as a measles virus.

The invention thus involves methods and compositions for developing live vaccine candidates based on chimeras that employ a parainfluenza virus or subviral particle that is recombinantly modified to incorporate one or more antigenic determinants of a heterologous pathogen(s). Chimeric PIVs of the invention are constructed through a cDNA-based virus recovery system. Recombinant chimeric PIVs made from cDNA replicate independently and are propagated in a similar manner as biologically-derived viruses. The recombinant viruses are engineered to incorporate nucleotide sequences from both a vector (i.e., a "recipient" or "background") PIV genome or antigenome, and one or more heterologous "donor" sequences encoding one or more antigenic determinants of a different PIV or heterologous pathogen—to produce an infectious, chimeric virus or subviral particle. In this manner, candidate vaccine viruses are recombinantly engineered to elicit an immune response against one or more PIVs or a polyspecific response against a selected PIV and a non-PIV pathogen in a mammalian host susceptible to infection therefrom. Preferably the PIV and/or non-PIV pathogen(s) from which the heterologous sequences encoding the antigenic determinant(s) are human pathogens and the host is a human host. Also preferably, the vector PIV is a human PIV, although non-human PIVs, for example a bovine PIV (BPIV), can be employed as a vector to incorporate antigenic determinants of human PIVs and other human pathogens. Chimeric PIVs according to the invention may elicit an immune response against a specific PIV, e.g., HPIV1, HPIV2, HPIV3, or a polyspecific immune response against multiple PIVs, e.g., HPIV1 and HPIV2. Alternatively, chimeric PIVs of the invention may elicit a polyspecific immune response against one or more PIVs and a non-PIV pathogen such as measles virus.

Exemplary chimeric PIV of the invention incorporate a chimeric PIV genome or antigenome as described above, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric PIV of the invention include a partial or complete "vector" PIV genome or antigenome derived from or patterned after a human PIV or non-human PIV combined with one or more heterologous gene(s) or genome segment(s) of a different PIV or other pathogen to form the chimeric PIV genome or antigenome. In preferred aspects of the invention, chimeric PIV incorporate a partial or complete human PIV vector genome or antigenome combined with one or more heterologous gene(s) or genome segment(s) from a second human PIV or a non-PIV pathogen such as measles virus.

The PIV "vector" genome or antigenome typically acts as a recipient or carrier to which are added or incorporated one or more "donor" genes or genome segments of a heterologous pathogen. Typically, polynucleotides encoding one or more antigenic determinants of the heterologous pathogen are added to or substituted within the vector genome or antigenome to yield a chimeric PIV that thus acquires the ability to elicit an immune response in a selected host against the heterologous pathogen. In addition, the chimeric virus may exhibit other novel phenotypic characteristics compared to one or both of the vector PIV and heterologous pathogens. For example, addition or substitution of heterologous genes or genome segments within a vector PIV strain may additionally, or independently, result in an increase in attenuation, growth changes, or other desired phenotypic changes as compared with a corresponding phenotype of the unmodified vector virus and/or donor. In one aspect of the invention, chimeric PIVs are attenuated for greater efficacy as a vaccine candidate by incorporation of large polynucleotide inserts which specify the level of attenuation in the resulting chimeric virus dependent upon the size of the insert.

Preferred chimeric PIV vaccine candidates of the invention bear one or more major antigenic determinants of a human PIV, e.g., of HPIV1, HPIV2 or HPIV3, and thus elicit an effective immune response against the selected PIV in human hosts. The antigenic determinant which is specific for a selected human PIV may be encoded by the vector genome or antigenome, or may be inserted within or joined to the PIV vector genome or antigenome as a heterologous polynucleotide sequence from a different PIV. The major protective antigens of human PIVs are their HN and F glycoproteins, although other proteins can also contribute to a protective or therapeutic immune response. In this context, both humoral and cell mediated immune responses are advantageously elicited by representative vaccine candidates within the invention. Thus, polynucleotides encoding antigenic determinants that may be present in the vector genome or antigenome, or integrated therewith as a heterologous gene or genome segment, may encode one or more PIV N, P, C, D, V, M, F, HN and/or L protein(s) or selected immunogenic fragment(s) or epitope(s) thereof from any human PIV.

In addition to having one or more major antigenic determinants of a selected human PIV, preferred chimeric PIV vaccine viruses of the invention bear one or more major antigenic determinants of a second human PIV or of a non-PIV pathogen. In exemplary aspects, the chimeric PIV includes a vector genome or antigenome that is a partial or complete human PIV (HPIV) genome or antigenome, for example of HPIV3, and further includes one or more heterologous gene(s) or genome segment(s) encoding antigenic determinant(s) of at least one heterologous PIV, for example HPIV1 and/or HPIV2. Preferably, the vector genome or antigenome is a partial or complete HPIV3 genome or antigenome and the heterologous gene(s) or genome segment(s) encoding the antigenic determinant(s) is/are of one or more heterologous HPIV(s). In alternative embodiments, one or more genes or genome segments encoding one or more antigenic determinants of HPIV1 may be added to or substituted within the partial or complete HPIV3 genome or antigenome. Preferably, the antigenic determinant(s) of HPIV1 is/are selected from HPIV1 HN and F glycoproteins or comprise one or more antigenic domains, fragments or epitopes of the HN and/or F glycoproteins. In various exemplary embodiments, both of the HPIV1 genes encoding the HN and F glycoproteins are substituted for counterpart HPIV3 HN and F genes in the HPIV3 vector genome or antigenome. These constructs yield chimeric PIVs that elicit a mono- or poly-specific immune response in humans to HPIV3 and/or HPIV1.

In additional exemplary embodiments, one or more genes or genome segments encoding one or more antigenic determinants of HPIV2 is/are added to, or incorporated within, a partial or complete HPIV3 genome or antigenome, yielding a new or additional immunospecificity of the resultant chimera against HPIV2 alone, or against HPIV3 and HPIV2. In more detailed aspects, one or more HPIV2 genes or genome segments encoding one or more HN and/or F glycoproteins or antigenic domains, fragments or epitopes thereof is/are added to or incorporated within the partial or complete HPIV3 vector genome or antigenome.

In yet additional aspects of the invention, multiple heterologous genes or genome segments encoding antigenic determinants of multiple heterologous PIVs are added to or incorporated within a partial or complete PIV vector genome or antigenome, preferably an HPIV vector genome or antigenome. In one preferred embodiment, heterologous genes or genome segments encoding antigenic determinants from both HPIV1 and HPIV2 are added to or incorporated within a partial or complete HPIV3 vector genome or antigenome. In more detailed aspects, one or more HPIV1 genes or genome segments encoding one or more HN and/or F glycoproteins (or antigenic domains, fragments or epitopes thereof) and one or more HPIV2 genes or genome segments encoding HN and/or F glycoproteins, antigenic domains, fragments or epitopes, is/are added to or incorporated within the partial or complete HPIV3 vector genome or antigenome. In one example, both HPIV1 genes encoding HN and F glycoproteins are substituted for counterpart HPIV3 HN and F genes to form a chimeric HPIV3-1 vector genome or antigenome, which is further modified by addition or incorporation of one or more genes or gene segments encoding single or multiple antigenic determinants of HPIV2. This is readily achieved within the invention, for example, by adding or substituting a transcription unit comprising an open reading frame (ORF) of an HPIV2 HN within the chimeric HPIV3-1 vector genome or antigenome. Following this method, specific constructs exemplifying the invention are provided which yield chimeric PIVs having antigenic determinants of both HPIV1 and HPIV2, as exemplified by the vaccine candidates rPIV3-1.2HN and rPIV3-1cp45.2HN described herein below.

In alternative aspects of the invention, chimeric PIVs of the invention are based on a human PIV vector genome or antigenome which is employed as a recipient for incorporation of major antigenic determinants from a non-PIV pathogen. Pathogens from which one or more antigenic determinants may be adopted into the chimeric PIV vaccine candidate include, but are not limited to, measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. This assemblage of pathogens that may be thus targeted for vaccine development according to the methods of the invention is exemplary only, and those skilled in the art will understand that the use of PIV vectors for carrying antigenic determinants extends broadly to a large host of additional pathogens.

This, in various alternative aspects of the invention, a human PIV genome or antigenome can be employed as a vector for incorporation of one or more major antigenic determinants from a wide range of non-PIV pathogens. Representative major antigens that can be incorporated within chimeric PIVs of the invention include, but are not limited to the measles virus HA and F proteins; the F, G, SH and M2 proteins of subgroup A and subgroup B respiratory syncytial virus, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G Protein, Epstein Barr Virus gp350 protein; filovirus G protein, bunyavirus G protein, flavivirus E and NS1 proteins, and alphavirus E protein.

Various human PIV vectors can be employed to carry heterologous antigenic determinants of non-PIV pathogens to elicit one or more specific humoral or cell mediated immune responses against the antigenic determinant(s) carried by the chimeric vaccine virus and hence elicit an effective immune response against the wild-type "donor" pathogen in susceptible hosts. In preferred embodiments, one or more heterologous genes or genome segments from the donor pathogen is joined to or inserted within a partial or complete HPIV3 genome or antigenome. Alternatively, the heterologous gene or genome segment may be incorporated within a chimeric HPIV vector genome or antigenome, for example a partial or complete HPIV3 genome or antigenome bearing one or more genes or genome segments of a heterologous PIV. For example, the gene(s) or genome segment(s) encoding the antigenic determinant(s) of a non-PIV pathogen may be combined with a partial or complete chimeric HPIV3-1 vector genome or antigenome, e.g., as described above having one or both HPIV1 genes encoding HN and F glycoproteins substituted for counterpart HPIV3 HN and F genes. Alternatively, the gene(s) or genome segment(s) encoding the antigenic determinant(s) of a non-PIV pathogen may be combined with a partial or complete chimeric genome or antigenome that incorporates single or multiple antigenic determinants of HPIV2, e.g., an HPIV2 HN gene, within an HPIV1 or HPIV3 vector genome or antigenome, or a chimeric HPIV3-1 vector genome or antigenome as described above. The heterologous gene(s) or genome segment(s) encoding one or more measles antigenic determinant(s) may be combined with any of the PIV vectors or chimeric PIV vectors disclosed herein. In the examples provided herein, the vector genome or antigenome is a partial or complete HPIV3 genome or antigenome, or a chimeric HPIV genome or antigenome comprising a partial or complete HPIV3 genome or antigenome having one or more genes or genome segments encoding antigenic determinant(s) of a heterologous HPIV added or incorporated therein. In one such chimeric construct, a transcription unit comprising an open reading frame (ORF) of a measles virus HA gene is added to a HPIV3 vector genome or antigenome at various positions, yielding exemplary chimeric PIV/measles vaccine candidates rPIV3(HA HN-L), rPIV3(HA N-P), rcp45L(HA N-P), rPIV3(HA P-M), or rcp45L(HA P-M).

To construct chimeric PIV clones of the invention, a heterologous gene or genome segment of a donor PIV or non-PIV pathogen may be added or substituted at any operable position in the vector genome or antigenome. Often, the position of a gene or gene segment substitution will correspond to a wild-type gene order position of a counterpart gene or genome segment within the partial or complete PIV vector genome or antigenome. In other embodiments, the heterologous gene or genome segment is added or substituted at a position that is more promoter-proximal or promotor-distal compared to a wild-type gene order position of a counterpart gene or genome segment within the background genome or antigenome, to enhance or reduce expression, respectively, of the heterologous gene or genome segment. In more detailed aspects of the invention, a heterologous genome segment, for example a genome segment encoding an immunogenic ectodomain of a heterologous PIV or non-PIV pathogen, can be substituted for a corresponding genome segment in a counterpart gene in the PIV vector genome or antigenome to yield constructs encoding chimeric proteins, e.g. fusion proteins having a cytoplasmic tail and/or transmembrane domain of one PIV fused to an ectodomain of another PIV or non-PIV pathogen. In alternate embodiments, a chimeric PIV genome or antigenome may be engineered to encode a polyspecific chimeric glycoprotein in the recombinant virus or subviral particle having immunogenic glycoprotein domains or epitopes from two different pathogens. In yet additional embodiments, heterologous genes or genome segments from one PIV or non-PIV pathogen can be added (i.e., without substitution) within a PIV vector genome or antigenome to create novel immunogenic properties within the resultant clone. In these cases, the heterologous gene or genome segment may be added as a supernumerary gene or genome segment, optionally for the additional purpose of attenuating the resultant chimeric virus, in combination with a complete PIV vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete PIV vector genome or antigenome. Alternatively, the gene or genome segment can be inserted within other noncoding regions of the genome, for example, within 5' or 3' noncoding regions or in other positions where noncoding nucleotides occur within the vector genome or antigenome. In some instances, it may be desired to insert the heterologous gene or genome segment at a non-coding site corresponding to or overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

For the preferred purpose of constructing candidate vaccine viruses for clinical use, it is often desirable to adjust the attenuation phenotype of chimeric PIV of the invention by introducing additional mutations that increase or decrease the level of attenuation in the recombinant virus. Therefore, in additional aspects of the invention, attenuated, chimeric PIVs are produced in which the chimeric genome or antigenome is further modified by introducing one or more attenuating mutations that specify an attenuating phenotype in the resultant virus or subviral particle. These attenuating mutations may be generated de novo and tested for attenuating effects according to well known rational design mutagenesis strategies. Alternatively, the attenuating mutations may be identified in existing biologically derived mutant PIV or other viruses and thereafter incorporated into a chimeric PIV of the invention.

Preferred attenuating mutations in the latter context are readily identified and incorporated into a chimeric PIV, either by inserting the mutation within the vector genome or antigenome by cloning or mutagenizing the vector genome or antigenome to contain the attenuating mutation. Preferably, attenuating mutations are engineered within the vector genome or antigenome and are imported or copied from biologically derived, attenuated PIV mutants. These are recognized to include, for example, cold passaged (cp), cold adapted (ca), host range restricted (hr), small plaque (sp), and/or temperature sensitive (ts) PIV mutants. In exemplary embodiments, one or more attenuating mutations present in the well characterized JS HPIV3 cp45 mutant strain are incorporated within chimeric PIV of the invention, preferably including one or more mutations identified in the polymerase L protein, e.g., at a position corresponding to $Tyr_{942}$, $Leu_{992}$, or $Thr_{1558}$ of JS cp45. Alternatively or additionally, attenuating mutations present in the JS HPIV3 cp45 mutant strain are introduced in the N protein of chimeric PIV clones, for example which encode amino acid substitution(s) at a position corresponding to residues $Val_{96}$ or $Ser_{389}$ of JS cp45. Yet additional useful attenuating mutations encode amino acid substitution(s) in the C protein, e.g., at a position corresponding to $Ile_{96}$ of JS cp45. Other mutations identified in PIV3 JS cp45 that can be adopted to adjust attenuation of a chimeric PIV of the invention are found in the F protein, e.g., at a position corresponding to $Ile_{420}$ or $Ala_{450}$ of JS cp45, and in the HN protein, e.g., at a position corresponding to residue $Val_{384}$ of JS cp45.

Attenuating mutations from biologically derived PIV mutants for incorporation into chimeric PIV of the invention also include mutations in noncoding portions of the PIV genome or antigenome, for example in a 3' leader sequence.

Exemplary mutations in this context may be engineered at a position in the 3' leader of a recombinant virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45.

From PIV3 JS cp45 and other biologically derived PIV mutants, a large "menu" of attenuating mutations is provided, each of which mutations can be combined with any other mutation(s) for finely adjusting the level of attenuation in chimeric PIV vaccine candidates of the invention. In exemplary embodiments, chimeric PIVs are constructed which include one or more, and preferably two or more, mutations of HPIV3 JS cp45. Thus, chimeric PIVs of the invention selected for vaccine use often have two and sometimes three or more attenuating mutations from biologically derived PIV mutants or like model sources to achieve a satisfactory level of attenuation for broad clinical use. Preferably, these attenuating mutations incorporated within recombinant chimeric PIVs of the invention are stabilized by multiple nucleotide substitutions in a codon specifying the mutation.

Additional attenuating mutations can be readily adopted or engineered within chimeric PIVs of the invention that are identified in other viruses, particularly other nonsegmented negative stranded RNA viruses. This is accomplished by mapping a mutation identified in a heterologous negative stranded RNA virus to a corresponding, homologous site in a PIV vector genome or antigenome (or heterologous insert in the PIV chimera) and mutating the existing sequence in the "recipient" to the mutant genotype (either by an identical or conservative mutation), as described in U.S. Provisional Patent Application Ser. No. 60/129,006, filed on Apr. 13, 1999, incorporated herein by reference.

In yet additional aspects of the invention, chimeric PIVs, with or without attenuating mutations modeled after biologically derived attenuated mutant viruses, are constructed to have additional nucleotide modification(s) to yield a desired phenotypic, structural, or functional change. Typically, the selected nucleotide modification will be made within the partial or complete PIV vector genome, but such modifications can be made as well within any heterologous gene or genome segment that contributes to the chimeric clone. These modifications preferably specify a desired phenotypic change, for example a change in growth characteristics, attenuation, temperature-sensitivity, cold-adaptation, plaque size, host range restriction, or immunogenicity. Structural changes in this context include introduction or ablation of restriction sites into PIV encoding cDNAs for ease of manipulation and identification.

In preferred embodiments, nucleotide changes within the genome or antigenome of a chimeric PIV include modification of a viral gene by partial or complete deletion of the gene or reduction or ablation (knock-out) of its expression. Target genes for mutation in this context include any of the PIV genes, including the nucleocapsid protein N, phosphoprotein P, large polymerase subunit L, matrix protein M, hemagglutinin-neuraminidase protein HN, fusion protein F, and the products of the C, D and V open reading frames (ORFs). To the extent that the recombinant virus remains viable and infectious, each of these proteins can be selectively deleted, substituted or rearranged, in whole or in part, alone or in combination with other desired modifications, to achieve novel deletion or knock out mutants. For example, one or more of the C, D, and/or V genes may be deleted in whole or in part, or its expression reduced or ablated (e.g., by introduction of a stop codon, by a mutation in an RNA editing site, by a mutation that alters the amino acid specified by an initiation codon, or by a frame shift mutation in the targeted ORF(s)). In one embodiment, a mutation can be made in the editing site that prevents editing and ablates expression of proteins whose mRNA is generated by RNA editing (Kato et al., *EMBO* 16:578–587, 1997 and Schneider et al., *Virology* 227:314–322, 1997, incorporated herein by reference). Alternatively, one or more of the C, D, and/or V ORF(s) can be deleted in whole or in part to alter the phenotype of the resultant recombinant clone to improve growth, attenuation, immunogenicity or other desired phenotypic characteristics (see, U.S. patent application Ser. No. 09/350,821, filed by Durbin et al. on Jul. 9, 1999, incorporated herein by reference).

Alternative nucleotide modifications in chimeric PIV of the invention include a deletion, insertion, addition or rearrangement of a cis-acting regulatory sequence for a selected gene in the recombinant genome or antigenome. In one example, a cis-acting regulatory sequence of one PIV gene is changed to correspond to a heterologous regulatory sequence, which may be a counterpart cis-acting regulatory sequence of the same gene in a different PIV, or a cis-acting regulatory sequence of a different PIV gene. For example, a gene end signal may be modified by conversion or substitution to a gene end signal of a different gene in the same PIV strain. In other embodiments, the nucleotide modification may comprise an insertion, deletion, substitution, or rearrangement of a translational start site within the recombinant genome or antigenome, e.g., to ablate an alternative translational start site for a selected form of a protein.

In addition, a variety of other genetic alterations can be produced in a chimeric PIV genome or antigenome, alone or together with one or more attenuating mutations adopted from a biologically derived mutant PIV. For example, genes or genome segments from non-PIV sources may be inserted in whole or in part. In one such aspect, the invention provides methods for attenuating chimeric PIV vaccine candidates based on host range effects due to the introduction of one or more gene(s) or genome segment(s) from, e.g., a non-human PIV into a human PIV vector-based chimeric virus. For example, host range attenuation can be conferred on a HPIV-vector based chimeric construct by introduction of nucleotide sequences from a bovine PIV (BPIV) (see, e.g., (e.g., as disclosed in U.S. Provisional Application Ser. No. 60/143,134 filed on Jul. 9, 1999, incorporated herein by reference). These effects are attributed to structural and functional divergence between the vector and donor viruses and provide a stable basis for attenuation. For example, between HPIV3 and BPIV3 the percent amino acid identity for each of the N proteins is 86%, for P is 65%, M 93%, F 83%, HN 77%, and L 91%. All of these proteins are therefore candidates for introduction into a HPIV vector to yield an attenuated chimeric virus which cannot readily be altered by reversion. In exemplary embodiments, the vector genome or antigenome is an HPIV3 genome or antigenome and the heterologous gene or genome segment is a N ORF derived from a selected BPIV3 strain.

In yet additional aspects of the invention, the order of genes can be changed to cause attenuation or reduce or enhance expression of a particular gene. Alternatively, a PIV genome promoter can be replaced with its antigenome counterpart to yield additional desired phenotypic changes. Different or additional modifications in the recombinant genome or antigenome can be made to facilitate manipulations, such as the insertion of unique restriction sites in various intergenic regions or elsewhere. Nontranslated gene sequences can be removed to increase capacity for inserting foreign sequences.

In yet additional aspects, polynucleotide molecules or vectors encoding the chimeric PIV genome or antigenome can be modified to encode non-PIV sequences, e.g., a cytokine, a T-helper epitope, a restriction site marker, or a protein or immunogenic epitope of a microbial pathogen (e.g., virus, bacterium or fungus) capable of eliciting a protective immune response in an intended host. In one such embodiment, chimeric PIVs are constructed that incorporate a gene encoding a cytokine to yield novel phenotypic and immunogenic effects in the resulting chimera.

In addition to providing chimeric PIV for vaccine use, the invention provides related cDNA clones and vectors which incorporate a PIV vector genome or antigenome and heterologous polynucleotide(s) encoding one or more heterologous antigenic determinants, wherein the clones and vectors optionally incorporate mutations and related modifications specifying one or more attenuating mutations or other phenotypic changes as described above. Heterologous sequences encoding antigenic determinants and/or specifying desired phenotypic changes are introduced in selected combinations, e.g., into an isolated polynucleotide which is a recombinant cDNA vector genome or antigenome, to produce a suitably attenuated, infectious virus or subviral particle in accordance with the methods described herein. These methods, coupled with routine phenotypic evaluation, provide a large assemblage of chimeric PIVs having such desired characteristics as attenuation, temperature sensitivity, altered immunogenicity, cold-adaptation, small plaque size, host range restriction, genetic stability, etc. Preferred vaccine viruses among these candidates are attenuated and yet sufficiently immunogenic to elicit a protective immune response in the vaccinated mammalian host.

In related aspects of the invention, compositions (e.g., isolated polynucleotides and vectors incorporating a chimeric PIV-encoding cDNA) and methods are provided for producing an isolated infectious chimeric PIV. Included within these aspects of the invention are novel, isolated polynucleotide molecules and vectors incorporating such molecules that comprise a chimeric PIV genome or antigenome. Also provided is the same or different expression vector comprising one or more isolated polynucleotide molecules encoding N, P, and L proteins. These proteins can alternatively be expressed directly from the genome or antigenome cDNA. The vector(s) is/are preferably expressed or coexpressed in a cell or cell-free lysate, thereby producing an infectious chimeric parainfluenza virus particle or subviral particle.

The above methods and compositions for producing chimeric PIV yield infectious viral or subviral particles, or derivatives thereof. An infectious virus is comparable to the authentic PIV particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, and L proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule comprising a chimeric PIV genome or antigenome as described above, and an expression vector (the same or different vector) which comprises one or more isolated polynucleotide molecules encoding the N, P, and L proteins of PIV. One or more of these proteins also can be expressed from the genome or antigenome cDNA. Upon expression the genome or antigenome and N, P and L proteins combine to produce an infectious chimeric parainfluenza virus or subviral particle.

In other embodiments of the invention a cell or cell-free expression system (e.g., a cell-free lysate) is provided which incorporates an expression vector comprising an isolated polynucleotide molecule encoding a chimeric PIV, and an expression vector comprising one or more isolated polynucleotide molecules encoding N, P, and L proteins of a PIV. Upon expression, the genome or antigenome and N, P, and L proteins combine to produce an infectious PIV particle, such as a viral or subviral particle.

The chimeric PIVs of the invention are useful in various compositions to generate a desired immune response against one or more PIVs, or against PIV and a non-PIV pathogen, in a host susceptible to infection therefrom. Chimeric PIV recombinants are capable of eliciting a mono- or polyspecific protective immune response in an infected mammalian host, yet are sufficiently attenuated so as to not cause unacceptable symptoms of disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated chimeric parainfluenza virus or subviral particle as described above. In preferred embodiments, the vaccine is comprised of a chimeric PIV having at least one, and preferably two or more additional mutations or other nucleotide modifications that specify a suitable balance of attenuation and immunogenicity. The vaccine can be formulated in a dose of $10^3$ to $10^7$ PFU of attenuated virus. The vaccine may comprise attenuated chimeric PIV that elicits an immune response against a single PIV strain or against multiple PIV strains or groups. In this regard, chimeric PIV can be combined in vaccine formulations with other PIV vaccine strains, or with other viral vaccine viruses such as RSV.

In related aspects, the invention provides a method for stimulating the immune system of an individual to elicit an immune response against one or more PIVs, or against PIV and a non-PIV pathogen, in a mammalian subject. The method comprises administering a formulation of an immunologically sufficient amount a chimeric PIV in a physiologically acceptable carrier and/or adjuvant. In one embodiment, the immunogenic composition is a vaccine comprised of a chimeric PIV having at least one, and preferably two or more attenuating mutations or other nucleotide modifications specifying a desired phenotype and/or level of attenuation as described above. The vaccine can be formulated in a dose of $10^3$ to $10^7$ PFU of attenuated virus. The vaccine may comprise an attenuated chimeric PIV that elicits an immune response against a single PIV, against multiple PIVs, e.g., HPIV1 and HPIV3, or against one or more PIV(s) and a non-PIV pathogen such as measles or RSV. In this context, chimeric PIVs can elicit a monospecific immune response or a polyspecific immune response against multiple PIVs, or against one or more PIV(s) and a non-PIV pathogen. Alternatively, chimeric PIV having different immunogenic characteristics can be combined in a vaccine mixture or administered separately in a coordinated treatment protocol to elicit more effective protection against one PIV, against multiple PIVs, or against one or more PIV(s) and a non-PIV pathogen such as measles or RSV. Preferably the immunogenic compositions of the invention are administered to the upper respiratory tract, e.g., by spray, droplet or aerosol. Preferably the immunogenic composition is administered to the upper respiratory tract, e.g., by spray, droplet or aerosol.

RSV and PIV3 cause significant amount of illness within the first four months of life, whereas most of the illness caused by PIV1 and PIV2 occurs after six months of age (Collins et al., In *Fields Virology*, Vol. 1, pp. 1205–1243, Lippincott-Raven Publishers, Philadelphia, 1996; Reed et al., *J. Infect. Dis.* 175:807–13, 1997). A preferred immunization sequence employing live attenuated RSV and PIV vaccines is to administer RSV and PIV3 as early as one month of age (e.g., at one and two months of age) followed by a bivalent PIV1 and PIV2 vaccine at four and six months of age. It is thus desirable to employ the methods of the invention to administer multiple PIV vaccines, including one or more chimeric PIV vaccines, coordinately, e.g., simultaneously in a mixture or separately in a defined temporal sequence (e.g., in a daily or weekly sequence), wherein each vaccine virus preferably expresses a different heterologous protective antigen. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

Importantly, the presence of multiple PIV serotypes and their unique epidemiology with PIV3 disease occurring at an earlier age than that of PIV1 and PIV2 makes it desirable to sequentially immunize an infant with different PIV vectors each expressing the same heterologous antigenic determinant such as the measles virus HA. This sequential immunization permits the induction of the high titer of antibody to the heterologous protein that is characteristic of the secondary antibody response. In one embodiment, early infants (e.g. 2–4 month old infants) can be immunized with an attenuated chimeric virus of the invention, for example a chimeric HPIV3 expressing the measles virus HA protein and also adapted to elicit an immune response against HPIV3, such as rcp45L(HA P-M). Subsequently, e.g., at four months of age the infant is again immunized but with a different, secondary vector construct, such as the rPIV3-1 cp45L virus expressing the measles virus HA gene and the HPIV1 antigenic determinants as the functional, obligate glycoproteins of the vector. Following the first vaccination, the vaccinee will elicit a primary antibody response to both the PIV3 HN and F proteins and to the measles virus HA protein, but not to the PIV1 HN and F protein. Upon secondary immunization with the rPIV3-1 cp45L expressing the measles virus HA, the vaccinee will be readily infected with the vaccine because of the absence of antibody to the PIV1 HN and F proteins and will develop both a primary antibody response to the PIV1 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric vaccine viruses disclosed herein, simultaneous with stimulation of an initial and then secondary, high titer protective response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype. The success of sequential immunization with rPIV3 and rPIV3-1 virus vaccine candidates as described above has been demonstrated. (Tao et al., *Vaccine* 17:1100–8, 1999).

BRIEF DESCRIPTION OF THE DRAWINGS

The file of this patent contains at least one drawing/photograph executed in color. Copies of this patent with color drawing(s)/photograph(s) will be provided by the Office upon request and payment of the necessary fee.

FIG. 1A provides a diagram (top; not to scale) of the 1926 nt insert containing the complete open reading frame of the hemagglutinin (HA) gene of the Edmonston wildtype strain of measles virus engineered to express the measles virus HA from an extra transcriptional unit. The insert contains, in 5' to 3' order: an Af/II site; nts 3699–3731 from the HPIV3 antigenome which contains the P/M gene junction, including downstream noncoding sequence for the P gene, its gene-end signal, the intergenic region, and the M gene-start signal; three additional nts (GCG); the complete measles virus HA ORF; HPIV3 nt 3594–3623 from the downstream noncoding region of the P gene; and a second Af/II site. FIG. 1A, Panel 1 illustrates the complete antigenome of the JS wildtype strain of HPIV3 (rPIV3) with the introduced Af/II site in the 3'-noncoding region of the N gene before (top) and after (bottom) insertion of the measles HA ORF. FIG. 1A, Panel 2 illustrates the complete antigenome of the JS wildtype strain of HPIV3 (rPIV3) with the introduced Af/II site in the 3'-noncoding region of the P gene before (top) and after (bottom) insertion of the measles HA ORF.

FIG. 1B provides a diagram (top; not to scale) of the 2028 nt insert containing the compete ORF of the HA gene of measles virus. The insert contains, in 5' to 3' order: a StuI site; nts 8602 to 8620 from the HPIV3 antigenome, which consist of downstream noncoding sequence from the HN gene and its gene-end signal; the conserved HPIV3 intergenic trinucleotide; nts 6733 to 6805 from the HPIV3 antigenome, which contains the HN gene-start and upstream noncoding region; the measles virus HA ORF; HPIV3 nts 8525–8597, which are downstream noncoding sequences from the HN gene; and a second StuI site. The construction is designed to, upon insertion, regenerate the HPIV3 HN gene containing the StuI site, and place the measles virus ORF directly after it flanked by the transcription signals and noncoding region of the HPIV3 HN gene. The complete antigenome of HPIV3 JS wildtype (rPIV3) with the introduced StuI site at nt position 8600 in the 3'-noncoding region of the HN gene is illustrated in the next (middle) diagram. Below is the antigenome of HPIV3 expressing the measles HA protein inserted into the StuI site. The HA cDNA used for this insertion came from an existing plasmid, rather than from the Edmonston wild type measles virus, which was used for the insertions in the N/P and P/M regions. This cDNA had two amino acid differences from the HA protein inserted in FIG. 1A, and their location in the HA gene of measles virus is indicated by the asterisks in FIG. 1B.

FIGS. 9A–9C present multi-step growth curves of GU and NCR insertion mutations compared with rHPIV3 wt and rcp45$_L$. LLC-MK2 monolayers in 6-well plates were infected with each HPIV3 in triplicate at a multiplicity of infection (m.o.i.) of 0.01 and were washed 4 times after removal of the virus supernatant. At 0 hr and at 24 hrs intervals for 6 days post-infection, 0.5 ml virus medium from each well was harvested and 0.5 ml fresh medium was added to each well. Harvested samples were stored at −80° C. Virus present in the samples was quantified by titration on LLC-MK2 monolayers in 96-well plates incubated at 32° C. The titers of viruses are expressed as TCID$_{50}$/ml. The average of three independent infections from one experiment is shown. The lower limit of detection is 0.7 log$_{10}$ TCID$_{50}$/ml. FIG. 9A-GU insertion mutants; FIG. 9B-NCR insertion mutants; FIG. 9C-cp45L/GU insertion mutant.

DESCRIPTION OF THE SPECIFIC EMBODIMENTS

Figure 2:
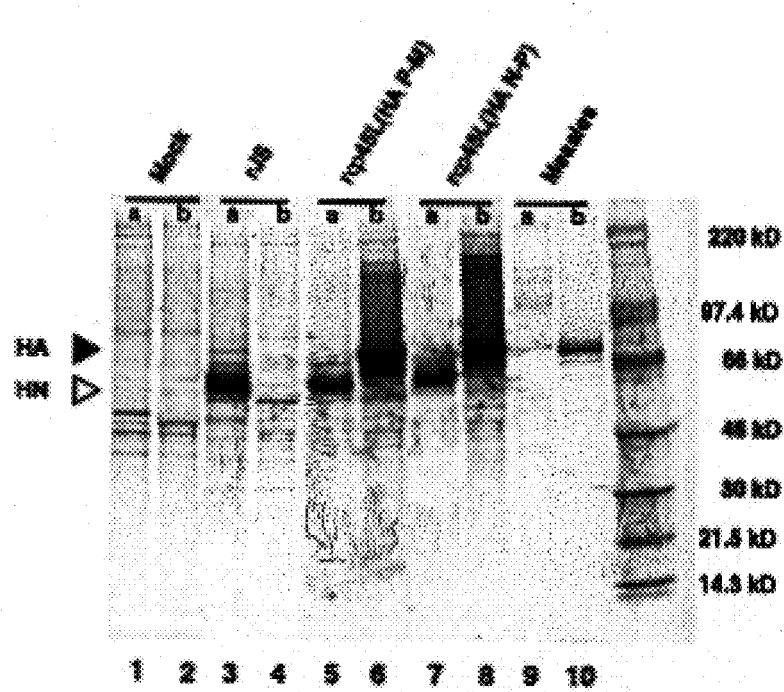
FIG. 2 illustrates expression of the HA protein of measles virus by rHPIV3-measles virus-HA chimeric viruses in LLC-MK2 cells. The figure presents a radioimmunoprecipitation assay (RIPA) demonstrating that the measles HA protein is expressed by the recombinant chimeric viruses rcp45L(HA P-M) and rcp45L(HA N-P), and by the Edmonston wild type strain of measles virus (Measles), but not by the rJS wild type HPIV3 (rJS). Lanes A—$^{35}$S-labeled infected cell lysates were immunoprecipitated by a mixture of three monoclonal antibodies specific to the HPIV3 HN protein). The 64 kD band corresponding to the HN protein (open arrow) is present in each of the three HPIV3 infected cell lysates (lanes 3, 5, and 7), but not in the measles virus infected cell lysates (lane 9), confirming that the rcp45L(HA P-M) and rcp45L(HA N-P) chimeras are indeed HPIV3 and express similar levels of HN proteins. Lanes (b)—$^{35}$S-labeled infected cell lysates were immunoprecipitated by a mixture of monoclonal antibodies which recognizes the HA glycoprotein of measles virus (79-XV-V17, 80-III-B2, 81-1-366) (Hummel et al., *J. Virol.* 69:1913–6, 1995; Sheshberadaran et al., *Arch. Virol.* 83:251–68, 1985, each incorporated herein by reference). The 76 kD band corresponding to the HA protein (closed arrow) is present in lysates from cells infected with the rcp45L(HA) chimeric viruses (lanes 6, 8) and the measles virus (lane 10), but not in the lysates from rJS infected cells (lane 4), a HPIV3 wild type virus which does not encode a measles virus HA gene.

The instant invention provides methods and compositions for the production and use of novel, chimeric parainfluenza viruses (PIVs) and associated vaccines. The chimeric viruses of the invention are infectious and immunogenic in humans and other mammals and are useful for generating immune responses against one or more PIVs, for example against one or more human PIVs (HPIVs). Alternatively, chimeric PIVs are provided that elicit an immune response against a selected PIV and one or more additional pathogens, for example against both a HPIV and measles virus. The immune response elicited can involve either or both humoral and/or cell mediated responses. Preferably, chimeric PIVs of the invention are attenuated to yield a desired balance of attenuation and immunogenicity for vaccine use.

The invention thus provides novel methods for designing and producing attenuated, chimeric PIVs that are useful as vaccine agents for preventing and/or treating infection and related disease symptoms attributable to PIV and other pathogens. In accordance with the methods of the invention, chimeric parainfluenza viruses or subviral particles are constructed using a PIV "vector" genome or antigenome that is recombinantly modified to incorporate one or more antigenic determinants of a heterologous pathogen. The vector genome or antigenome is comprised of a partial or complete PIV genome or antigenome, which may itself incorporate nucleotide modifications such as attenuating mutations. The vector genome or antigenome is modified to form a chimeric structure through incorporation of a heterologous gene or genome segment. More specifically, chimeric PIVs of the invention are constructed through a cDNA-based virus recovery system that yields recombinant viruses that incorporate a partial or complete vector or "background" PIV genome or antigenome combined with one or more "donor" nucleotide sequences encoding the heterologous antigenic determinant(s). Preferably the PIV vector comprises a HPIV genome or antigenome, although non-human PIVs, for example a bovine PIV (BPIV), can be employed as a vector to incorporate antigenic determinants of human PIVs and other human pathogens. In exemplary embodiments described herein, a human PIV3 (HPIV3) vector genome or antigenome is modified to incorporate one or more genes or genome segments that encode antigenic determinant(s) of one or more heterologous PIVs (e.g., HPIV1 and/or HPIV2), and/or a non-PIV pathogen (e.g., measles virus). Thus constructed, chimeric PIVs of the invention may elicit an immune response against a specific PIV, e.g., HPIV1, HPIV2, and/or HPIV3, or against a non-PIV pathogen. Alternatively, compositions and methods are provided for eliciting a polyspecific immune response against multiple PIVs, e.g., HPIV1 and HPIV3, or against one or more HPIVs and a non-PIV pathogen such as measles virus.

Exemplary chimeric PIV of the invention incorporate a chimeric PIV genome or antigenome as described above, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components. Additional PIV proteins may be included in various combinations to provide a range of infectious subviral particles, up to a complete viral particle or a viral particle containing supernumerary proteins, antigenic determinants or other additional components.

In preferred aspects of the invention, chimeric PIV incorporate a partial or complete human PIV vector genome or antigenome combined with one or more heterologous gene(s) or genome segment(s) from a second human PIV or a non-PIV pathogen such as measles virus. The PIV "vector" genome or antigenome typically acts as a recipient or carrier to which are added or incorporated one or more "donor" genes or genome segments of a heterologous pathogen. Typically, polynucleotides encoding one or more antigenic determinants of the heterologous pathogen are added to or substituted within the vector genome or antigenome to yield a chimeric PIV that thus acquires the ability to elicit an immune response in a selected host against the heterologous pathogen. In addition, the chimeric virus may exhibit other novel phenotypic characteristics compared to one or both of the vector PIV and heterologous pathogens.

The partial or complete vector genome or antigenome generally acts as a backbone into which heterologous genes or genome segments of a different pathogen are incorporated. Often, the heterologous pathogen is a different PIV from which one or more gene(s) or genome segment(s) is/are of are combined with, or substituted within, the vector genome or antigenome. In addition to providing novel immunogenic characteristics, the addition or substitution of heterologous genes or genome segments within the vector PIV strain may confer an increase or decrease in attenuation, growth changes, or other desired phenotypic changes as compared with the corresponding phenotype(s) of the unmodified vector and donor viruses. Heterologous genes and genome segments from other PIVs that may be selected as inserts or additions within chimeric PIV of the invention include genes or genome segments encoding the PIV N, P, C, D, V, M, F, HN and/or L protein(s) or one or more antigenic determinant(s) thereof.

Heterologous genes or genome segments of one PIV may be added as a supernumerary genomic element to a partial or complete genome or antigenome of a different PIV. Alternatively, one or more heterologous gene(s) or genome segment(s) of one PIV may be substituted at a position corresponding to a wild-type gene order position of a counterpart gene(s) or genome segment(s) that is deleted within the PIV vector genome or antigenome. In yet additional embodiments, the heterologous gene or genome segment is added or substituted at a position that is more promoter-proximal or promotor-distal compared to a wild-type gene order position of the counterpart gene or genome segment within the vector genome or antigenome to enhance or reduce, respectively, expression of the heterologous gene or genome segment.

The introduction of heterologous immunogenic proteins, protein domains and immunogenic epitopes to produce chimeric PIV is particularly useful to generate novel immune responses in an immunized host. Addition or substitution of an immunogenic gene or genome segment from one, donor pathogen within a recipient PIV vector genome or antigenome can generate an immune response directed against the donor pathogen, the PIV vector, or against both the donor pathogen and vector.

To achieve this purpose, chimeric PIV may be constructed that express a chimeric protein, for example an immunogenic glycoprotein having a cytoplasmic tail and/or transmembrane domain specific to a vector fused to a heterologous ectodomain of a different PIV or non-PIV pathogen to provide a fusion protein that elicits an immune response against the heterologous pathogen. For example, a heterologous genome segment encoding a glycoprotein ectodomain from a human PIV1 HN or F glycoprotein may be joined with a genome segment encoding the corresponding HPIV3 HN or F glycoprotein cytoplasmic and transmembrane domains to form a HPIV3-1 chimeric glycoprotein that elicits an immune response against HPIV1.

Briefly, PIV of the invention expressing a chimeric glycoprotein comprise a major nucleocapsid (N) protein, a nucleocapsid phosphoprotein (P), a large polymerase protein (L), and a HPIV vector genome or antigenome that is modified to encode a chimeric glycoprotein. The chimeric glycoprotein incorporates one or more heterologous antigenic domains, fragments, or epitopes of a second, antigenically distinct HPIV. Preferably, this is achieved by substitution within the HPIV vector genome or antigenome of one or more heterologous genome segments of the second HPIV that encode one or more antigenic domains, fragments, or epitopes, whereby the genome or antigenome encodes the chimeric glycoprotein that is antigenically distinct from the parent, vector virus.

In more detailed aspects, the heterologous genome segment or segments preferably encode a glycoprotein ectodomain or immunogenic portion or epitope thereof, and optionally include other portions of the heterologous or "donor" glycoprotein, for example both an ectodomain and transmembrane region that are substituted for counterpart glycoprotein ecto- and transmembrane domains in the vector genome or antigenome. Preferred chimeric glycoproteins in this context may be selected from HPIV HN and/or F glycoproteins, and the vector genome or antigenome may be modified to encode multiple chimeric glycoproteins. In preferred embodiments, the HPIV vector genome or antigenome is a partial HPIV3 genome or antigenome and the second, antigenically distinct HPIV is either HPIV1 or HPIV2. In one exemplary embodiment described below, both glycoprotein ectodomain(s) of HPIV2 HN and F glycoproteins are substituted for corresponding HN and F glycoprotein ectodomains in the HPIV3 vector genome or antigenome. In another exemplary embodiment, PIV2 ectodomain and transmembrane regions of one or both HN and/or F glycoproteins are fused to one or more corresponding PIV3 cytoplasmic tail region(s) to form the chimeric glycoprotein. Further details concerning these aspects of the invention are provided in United States Patent Application entitled CONSTRUCTION AND USE OF RECOMBINANT PARAINFLUENZA VIRUSES EXPRESSING A CHIMERIC GLYCOPROTEIN, filed on Dec. 10, 1999 by Tao et al. and identified by Ser. No. 09/459,062, incorporated herein by reference.

To construct chimeric PIVs of the invention carrying a heterologous antigenic determinant of a non-PIV pathogen, a heterologous gene or genome segment of the donor pathogen may be added or substituted at any operable position in the vector genome or antigenome. In one embodiment, heterologous genes or genome segments from a non-PIV pathogen can be added (i.e., without substitution) within a PIV vector genome or antigenome to create novel immunogenic properties within the resultant clone. In these cases, the heterologous gene or genome segment may be added as a supernumerary gene or genome segment, optionally for the additional purpose of attenuating the resultant chimeric virus, in combination with a complete PIV vector genome or antigenome. Alternatively, the heterologous gene or genome segment may be added in conjunction with deletion of a selected gene or genome segment in the vector genome or antigenome.

In preferred embodiments of the invention, the heterologous gene or genome segment is added at an intergenic position within the partial or complete PIV vector genome or antigenome. Alternatively, the gene or genome segment can be inserted within other noncoding regions of the genome, for example, within 5' or 3' noncoding regions or in other positions where noncoding nucleotides occur within the vector genome or antigenome. In one aspect, the heterologous gene or genome segment is inserted at a non-coding site overlapping a cis-acting regulatory sequence within the vector genome or antigenome, e.g., within a sequence required for efficient replication, transcription, and/or translation. These regions of the vector genome or antigenome represent target sites for disruption or modification of regulatory functions associated with introduction of the heterologous gene or genome segment.

As used herein, the term "gene" generally refers to a portion of a subject genome, e.g., a PIV genome, encoding an mRNA and typically begins at the upstream end with a gene-start (GS) signal and ends at the downstream end with the gene-end (GE) signal. The term gene is also interchangeable with the term "translational open reading frame", or ORF, particularly in the case where a protein, such as the PIV C protein, is expressed from an additional ORF rather than from a unique mRNA. In the exemplary case of HPIV3, the genome is a single strand of negative-sense RNA 15462 nucleotides (nt) in length (Galinski et al., *Virology* 165: 499–510, (1988); Stokes et al., *Virus Res.* 25:91–103 (1992)). At least eight proteins are encoded by the HPIV3 genome: the nucleocapsid protein N, the phosphoprotein P, the C and D proteins of unknown functions, the matrix protein M, the fusion glycoprotein F, the hemagglutinin-neuraminidase glycoprotein HN, and the large polymerase protein L (Collins et al., 3rd ed. In *"Fields Virology,"* B. N. Fields, D. M. Knipe, P. M. Howley, R. M. Chanock, J. L. Melnick, T. P. Monath, B. Roizman, and S. E. Straus, Eds., Vol. 1, pp. 1205–1243. Lippincott-Raven Publishers, Philadelphia, 1996). The viral genome of all PIVs also contains extragenic leader and trailer regions, possessing all or part of the promoters required for viral replication and transcription, as well as non-coding and intergenic regions. Thus, the PIV genetic map is represented as 3' leader-N-P/C/D/V-M-F-HN-L-5' trailer. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary genome sequences have been described for the human PIV3 strains JS (GenBank accession number Z11575, incorporated herein by reference) and Washington (Galinski M. S. In Kingsbury, D. W. (Ed.), the Parayxoviruses, pp. 537–568, Plenum Press, New York, 1991, incorporated herein by reference), and for the bovine PIV3 strain 910N (GenBank accession number D80487, incorporated herein by reference).

To construct chimeric PIVs of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof. When a subject genome segment encodes an antigenic determinant, the genome segment encodes at least one immunogenic epitope capable of eliciting a humoral or cell mediated immune response in a mammalian host. The genome segment may also encode an immunogenic fragment or protein domain. In other aspects, the donor genome segment may encode multiple immunogenic domains or epitopes, including recombinantly synthesized sequences that comprise multiple, repeating or different, immunogenic domains or epitopes.

Alternative chimeric PIV of the invention will contain protective antigenic determinants of HPIV1, HPIV2 and/or HPIV3. This is preferably achieved by expression of one or more HN and/or F genes or genome segments by the vector PIV, or as extra or substitute genes from the heterologous donor pathogen. In certain embodiments, a HPIV3-1 or HPIV3-2 chimeric virus may be constructed for use as a vaccine or vector strain, in which the HPIV1 or HPIV2 HN and/or F genes replace their PIV3 counterpart(s) (Skiadopoulos et al., *Vaccine* In press, 1999; Tao et al., *Vaccine* 17:1100–1108, 1999; U.S. patent application Ser. No. 09/083,793, filed May 22, 1998, each incorporated herein by reference). In this context, a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., *J Virol* 72:1762–8, 1998; Tao et al., *J Virol* 72:2955–2961, 1998; Tao et al., *Vaccine* 17:1100–1108, 1999, incorporated herein by reference). rPIV3-1.cp45L is attenuated in hamsters and induced a high level of resistance to challenge with PIV1. A recombinant chimeric virus, designated rPIV3-1.cp45, has also been produced that contains 12 of the 15 cp45 mutations, i.e., excluding the mutations in HN and F, and is highly attenuated in the upper and lower respiratory tract of hamsters (Skiadopoulos et al., *Vaccine* 18:503–510, 1999, incorporated herein by reference).

In preferred embodiments of the invention, the chimeric PIV bear one or more major antigenic determinants of a human PIV, or against multiple human PIVs, including HPIV1, HPIV2 or HPIV3. These preferred vaccine candidates elicit an effective immune response in humans against one or more selected HPIVs. As noted above, the antigenic determinant(s) that elicit(s) an immune response against HPIV may be encoded by the vector genome or antigenome, or may be inserted within or joined to the PIV vector genome or antigenome as a heterologous gene or gene segment. The major protective antigens of human PIVs are their HN and F glycoproteins. However, all PIV genes are candidates for encoding antigenic determinants of interest, including internal protein genes which may encode such determinants as, for example, CTL epitopes.

Preferred chimeric PIV vaccine viruses of the invention bear one or more major antigenic determinants from each of a plurality of HPIVs or from a HPIV and a non-PIV pathogen. Chimeric PIV thus constructed include a partial or complete HPIV genome or antigenome, for example of HPIV3, and one or more heterologous gene(s) or genome segment(s) encoding antigenic determinant(s) of a heterologous PIV, for example HPIV1 or HPIV2. In alternative embodiments, one or more genes or genome segments encoding one or more antigenic determinants of HPIV1 or HPIV2 may be added to or substituted within a partial or complete HPIV3 genome or antigenome. In various exemplary embodiments described below, both HPIV1 genes encoding the HN and F glycoproteins are substituted for counterpart HPIV3 HN and F genes in a chimeric PIV vaccine candidate. These and other constructs yield chimeric PIVs that elicit either a mono- or poly-specific immune response in humans to one or more HPIVs. Further detailed aspects of the invention are provided in United States Patent Application entitled CONSTRUCTION AND USE OF RECOMBINANT PARAINFLUENZA VIRUSES EXPRESSING A CHIMERIC GLYCOPROTEIN, filed on Dec. 10, 1999 by Tao et al. and identified by Ser. No. 09/459,062, and U.S. Provisional Patent Application entitled USE OF RECOMBINANT PARAINFLUENZA VIRUSES (PIVs) AS VECTORS TO PROTECT AGAINST INFECTION AND DISEASE CAUSED BY PIV AND OTHER HUMAN PATHOGENS, filed on Dec. 10, 1999 by Murphy et al. and identified by Ser. No. 60/170,195, each incorporated herein by reference.

In exemplary aspects of the invention, heterologous genes or genome segments encoding antigenic determinants from both HPIV1 and HPIV2 are added to or incorporated within a partial or complete HPIV3 vector genome or antigenome. For instance, one or more HPIV1 genes or genome segments encoding HN and/or F glycoproteins, or antigenic determinant(s) thereof, and one or more HPIV2 genes or genome segments encoding HN and/or F glycoproteins or antigenic determinants can be added to or incorporated within a partial or complete HPIV3 vector genome or antigenome. In one example described below, both HPIV1 genes encoding HN and F glycoproteins are substituted for counterpart HPIV3 HN and F genes to form a chimeric HPIV3-1 vector genome or antigenome. This vector construct can be further modified by addition or incorporation of one or more genes or gene segments encoding antigenic determinant(s) of HPIV2. Thus, specific constructs exemplifying the invention are provided which yield chimeric PIVs having antigenic determinants of both HPIV1 and HPIV2, as exemplified by the vaccine candidates rPIV3-1.2HN and rPIV3-1cp45.2HN described herein below.

In other preferred aspects of the invention, chimeric PIV incorporate a HPIV vector genome or antigenome modified to express one or more major antigenic determinants of non-PIV pathogen, for example measles virus. The methods of the invention are generally adaptable for incorporation of antigenic determinants from a wide range of additional pathogens within chimeric PIV vaccine candidates. In this regard the invention also provides for development of vaccine candidates against subgroup A and subgroup B respiratory syncytial viruses (RSV), mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses, among other pathogens. In this regard, pathogens that may be targeted for vaccine development according to the methods of the invention include viral and bacterial pathogens, as well as protozoans and multicellular pathogens. Useful antigenic determinants from many important human pathogens in this context are known or readily identified for incorporation within chimeric PIV of the invention. Thus, major antigens have been identified for the foregoing exemplary pathogens, including the measles virus HA and F proteins; the F, G, SH and M2 proteins of RSV, mumps virus HN and F proteins, human papilloma virus LI protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, flavivirus E and NS1 proteins, and alphavirus E. These major antigens, as well as other antigens known in the art for the enumerated pathogens and others, are well characterized to the extent that many of their antigenic determinants, including the full length proteins and their constituent antigenic domains, fragments and epitopes, are identified, mapped and characterized for their respective immunogenic activities.

Among the numerous, exemplary mapping studies that identify and characterize major antigens of diverse pathogens for use within the invention are epitope mapping studies directed to the hemagglutinin-neuraminidase (HN) gene of HPIV3. van Wyke Coelingh et al., *J. Virol.* 61(5): 1473–1477, 1987, incorporated herein by reference. This report provides detailed antigenic structural analyses for 16 antigenic variants of HPIV3 variants selected by using monoclonal antibodies (MAbs) to the HN protein which inhibit neuraminidase, hemagglutination, or both activities. Each variant possessed a single-point mutation in the HN gene, coding for a single amino acid substitution in the HN protein. Operational and topographic maps of the HN protein correlated well with the relative positions of the substitutions. Computer-assisted analysis of the HN protein predicted a secondary structure composed primarily of hydrophobic β sheets interconnected by random hydrophilic coil structures. The HN epitopes were located in predicted coil regions. Epitopes recognized by MAbs which inhibit neuraminidase activity of the virus were located in a region which appears to be structurally conserved among several paramyxovirus HN proteins and which may represent the sialic acid-binding site of the HN molecule.

This exemplary work, employing conventional antigenic mapping methods, identified single amino acids which are important for the integrity of HN epitopes. Most of these epitopes are located in the C-terminal half of the molecule, as expected for a protein anchored at its N terminus (Elango et al., *J. Virol.* 57:481–489, 1986). Previously published operational and topographic maps of the PIV3 HN indicated that the MAbs employed recognized six distinct groups of epitopes (I to VI) organized into two topographically separate sites (A and B), which are partially bridged by a third site (C). These groups of epitopes represent useful candidates for antigenic determinants that may be incorporated, alone or in various combinations, within chimeric PIVs of the invention. (See, also, Coelingh et al., *Virology* 143: 569–582, 1985; Coelingh et al., *Virology* 162:137–143, 1988; Ray et al., *Virology* 148:232–236, 1986; Rydbeck et al., *J. Gen. Virol.* 67:1531–1542, 1986, each incorporated herein by reference), Additional studies by van Wyke Coelingh et al., *J. Virol.* 63(1):375–382, 1989, provide further information relating to selection of PIV antigenic determinants for use within the invention. In this study, twenty-six monoclonal antibodies (MAbs) (14 neutralizing and 12 nonneutralizing) were used to examine the antigenic structure, biological properties, and natural variation of the fusion (F) glycoprotein of HPIV3. Analysis of laboratory-selected antigenic variants and of PIV3 clinical isolates indicated that the panel of MAbs recognizes at least 20 epitopes, 14 of which participate in neutralization. Competitive binding assays confirmed that the 14 neutralization epitopes are organized into three non-overlapping principal antigenic regions (A, B, and C) and one bridge site (AB), and that the 6 nonneutralization epitopes form four sites (D, E, F, and G). Most of the neutralizing MAbs were involved in nonreciprocal competitive binding reactions, suggesting that they induce conformational changes in other neutralization epitopes.

Other antigenic determinants for use within the invention have been identified and characterized for respiratory syncytial virus (RSV). For example, Beeler et al., *J. Virol.* 63(7):2941–2950, 1989, incorporated herein by reference, employed eighteen neutralizing monoclonal antibodies (MAbs) specific for the fusion glycoprotein of the A2 strain of RSV to construct a detailed topological and operational map of epitopes involved in RSV neutralization and fusion. Competitive binding assays identified three nonoverlapping antigenic regions (A, B, and C) and one bridge site (AB). Thirteen MAb-resistant mutants (MARMs) were selected, and the neutralization patterns of the MAbs with either MARMs or RSV clinical strains identified a minimum of 16 epitopes. MARMs selected with antibodies to six of the site A and AB epitopes displayed a small-plaque phenotype, which is consistent with an alteration in a biologically active region of the F molecule. Analysis of MARMs also indicated that these neutralization epitopes occupy topographically distinct but conformationally interdependent regions with unique biological and immunological properties. Antigenic variation in F epitopes was then examined by using 23 clinical isolates (18 subgroup A and 5 subgroup B) in cross-neutralization assays with the 18 anti-F MAbs. This analysis identified constant, variable, and hypervariable regions on the molecule and indicated that antigenic variation in the neutralization epitopes of the RSV F glycoprotein is the result of a noncumulative genetic heterogeneity. Of the 16 epitopes, 8 were conserved on all or all but 1 of 23 subgroup A or subgroup B clinical isolates. These antigenic determinants, including the full length proteins and their constituent antigenic domains, fragments and epitopes, all represent useful candidates for integration within chimeric PIV of the invention to elicit novel immune responses as described above. (See also, Anderson et al., *J. Infect. Dis.* 151:626–633, 1985; Coelingh et al., *J. Virol.* 63:375–382, 1989; Fenner et al., *Scand. J. Immunol.* 24:335–340, 1986; Fernie et al., *Proc. Soc. Exp. Biol. Med.* 171:266–271, 1982; Sato et al., *J. Gen. Virol.* 66:1397–1409, 1985; Walsh et al., *J. Gen. Virol.* 67:505–513, 1986, and Olmsted et al., *J. Virol.* 63(1):411–420, 1989, each incorporated herein by reference).

To express antigenic determinants of heterologous PIVs and non-PIV pathogens, the invention provides numerous human and non-human PIV vectors, including bovine PIV (BPIV) vectors. These vectors are readily modified according the recombinant methods described herein to carry heterologous antigenic determinants and elicit one or more specific humoral or cell mediated immune responses against the heterologous pathogen and vector PIV. In exemplary embodiments, one or more heterologous genes or genome segments from a donor pathogen is combined with a HPIV3 vector genome or antigenome. In other exemplary embodiments, the heterologous gene or genome segment is incorporated within a chimeric HPIV vector genome or antigenome, for example a chimeric HPIV3-1 vector genome or antigenome having one or both HPIV1 genes encoding the HN and F glycoproteins substituted for their counterpart HPIV3 HN and/or F gene(s). In more detailed embodiments, a transcription unit comprising an open reading frame (ORF) of the measles virus HA gene is added to a HPIV3 vector genome or antigenome at various positions, yielding exemplary chimeric PIV/measles vaccine candidates rPIV3(HA HN-L), rPIV3(HA N-P), rcp45L(HA N—P), rPIV3(HA P-M), or rcp45L(HA P-M). Alternatively, chimeric PIV for vaccine use may incorporate one or more antigenic determinants of HPIV2, for example an HPIV2 HN gene, within a chimeric HPIV3-1 vector genome or antigemome.

In other detailed embodiments of the invention, chimeric PIVs are engineered that incorporate heterologous nucleotide sequences encoding protective antigens from respiratory syncytial virus (RSV) to produce infectious, attenuated vaccine candidates. The cloning of RSV cDNA and other disclosure is provided in U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 (corresponding to International Publication No. WO 98/02530); U.S. patent application Ser. No. 09/291,894, filed on Apr. 13, 1999; U.S. Provisional Patent Application Ser. No. 60/129,006, filed on Apr. 13, 1999; Collins, et al., *Proc. Nat. Acad. Sci. USA* 92:11563–11567, 1995; Bukreyev, et al., *J Virol* 70:6634–41, 1996, Juhasz et al., *J. Virol.* 71(8):5814–5819, 1997; Durbin et al., *Virology* 235:323–332, 1997; He et al. *Virology* 237:249–260, 1997; Baron et al. *J. Virol.* 71:1265–1271, 1997; Whitehead et al., *Virology* 247(2): 232–9, 1998a; Whitehead et al., *J. Virol.* 72(5):4467–4471, 1998b; Jin et al. *Virology* 251:206–214, 1998; and Whitehead et al., *J. Virol.* 73:(4)3438–3442, 1999, and Bukreyev, et al., *Proc Nat Acad Sci USA* 96:2367–72, 1999, each incorporated herein by reference in its entirety for all purposes). Other reports and discussion incorporated or set forth herein identify and characterize RSV antigenic determinants that are useful within the invention.

PIV chimeras incorporating one or more RSV antigenic determinants, preferably comprise a human PIV (e.g., HPIV1, HPIV2, HPIV3) vector genome or antigenome with a heterologous gene or genome segment encoding an antigenic RSV glycoprotein, protein domain (e.g., a glycoprotein ectodomain) or one or more immunogenic epitopes. In one embodiment, one or more genes or genome segments from RSV F and/or G genes is/are combined with the vector genome or antigenome to form the chimeric PIV vaccine candidate. Certain of these constructs will express chimeric proteins, for example fusion proteins having a cytoplasmic tail and/or transmembrane domain of PIV fused to an ectodomain of RSV to yield a novel attenuated virus that elicits a multivalent immune response against both PIV and RSV As noted above, it is often desirable to adjust the phenotype of chimeric PIV for vaccine use by introducing additional mutations that increase or decrease attenuation or otherwise alter the phenotype of the chimeric virus. Detailed descriptions of the materials and methods for producing recombinant PIV from cDNA, and for making and testing various mutations and nucleotide modifications set forth herein as supplemental aspects of the present invention are provided in, e.g., Durbin et al., *Virology* 235:323–332, 1997; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference. In particular, these documents describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human PIV in accepted model systems, including murine and non-human primate model systems. In addition, these documents describe general methods for developing and testing immunogenic compositions, including monovalent and bivalent vaccines, for prophylaxis and treatment of PIV infection. Methods for producing infectious recombinant PIV by construction and expression of cDNA encoding a PIV genome or antigenome coexpressed with essential PIV proteins are also described in the above-incorporated documents, which include description of the following exemplary plasmids that may be employed to produce infectious PIV clones: p3/7(131)

(ATCC 97990); p3/7(131)2G (ATCC 97889); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

Also disclosed in the above-incorporated references are methods for constructing and evaluating infectious recombinant PIV that are modified to incorporate phenotype-specific mutations identified in biologically-derived PIV mutants, e.g., cold passaged (cp), cold adapted (ca), host range restricted (hr), small plaque (sp), and/or temperature sensitive (ts) mutants, for example the JS HPIV3 cp 45 mutant strain. Mutations identified in these mutants can be readily incorporated into chimeric PIV of the instant invention. In exemplary embodiments, one or more attenuating mutations occur in the polymerase L protein, e.g., at a position corresponding to $Tyr_{942}$, $Leu_{992}$, or $Thr_{1558}$ of JS cp45. Preferably, these mutations are incorporated in chimeric PIV of the invention by an identical, or conservative, amino acid substitution as identified in the biological mutant. In more detailed aspects, chimeric PIV for vaccine use incorporate one or more mutation wherein $Tyr_{942}$ is replaced by His, $Leu_{992}$ is replaced by Phe, and/or $Thr_{1558}$ is replaced by Ile. Substitutions that are conservative to these replacement amino acids are also useful to achieve desired attenuation in chimeric vaccine candidates.

Other exemplary mutations that can be adopted in chimeric PIVs from biologically derived PIV mutants include one or more mutations in the N protein, including specific mutations at a position corresponding to residues $Val_{96}$ or $Ser_{389}$ of JS cp45. In more detailed aspects, these mutations are represented as $Val_{96}$ to Ala or $Ser_{389}$ to Ala or substitutions that are conservative thereto. Also useful within chimeric PIV of the invention are amino acid substitution in the C protein, e.g., a mutation at a position corresponding to $Ile_{96}$ of JS cp45, preferably represented by an identical or conservative substitution of $Ile_{96}$ to Thr. Further exemplary mutations that can be adopted from biologically derived PIV mutants include one or more mutations in the F protein, including mutations adopted from JS cp45 at a position corresponding to residues $Ile_{420}$ or $Ala_{450}$ of JS cp45, preferably represented by acid substitutions $Ile_{420}$ to Val or $Ala_{450}$ to Thr or substitutions conservative thereto. Alternatively or in addition, chimeric PIV of the invention can adopt one or more amino acid substitutions in the HN protein, as exemplified by a mutation at a position corresponding to residue $Val_{384}$ of JS cp45, preferably represented by the substitution $Val_{384}$ to Ala.

Yet additional embodiments of the invention include chimeric PIV which incorporate one or more mutations in noncoding portions of the PIV genome or antigenome, for example in a 3' leader sequence, that specify desired phenotypic changes such as attenuation. Exemplary mutations in this context may be engineered at a position in the 3' leader of the chimeric virus at a position corresponding to nucleotide 23, 24, 28, or 45 of JS cp45. Yet additional exemplary mutations may be engineered in the N gene start sequence, for example by changing one or more nucleotides in the N gene start sequence, e.g., at a position corresponding to nucleotide 62 of JS cp45. In more detailed aspects, chimeric PIV incorporate a T to C change at nucleotide 23, a C to T change at nucleotide 24, a G to T change at nucleotide 28, and/or a T to A change at nucleotide 45. Additional mutations in extragenic sequences are exemplified by a A to T change in the N gene start sequence at a position corresponding to nucleotide 62 of JS.

These foregoing exemplary mutations which can be engineered in a chimeric PIV of the invention have been successfully engineered and recovered in recombinant PIV—as represented by the recombinant PIV clones designated rcp45, rcp45 L, rcp45 F, rcp45 M, rcp45 HN, rcp45 C, rcp45 F, rcp45 3'N, rcp3'NL, and rcp45 3'NCMFHN (Durbin et al., Virology 235:323–332, 1997; Skiadopolos et al., J. Virol. 72:1762–1768 (1998); Skiadopolos et al., J. Virol. 73:1374–1381, 1999; U.S. patent application Ser. No. 09/083,793, filed May 22, 1998; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In addition, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric vaccine candidate.

From JS cp45 and other biologically derived PIV mutants, a large "menu" of attenuating mutations is provided, each of which can be combined with any other mutation(s) for adjusting the level of attenuation, immunogenicity and genetic stability in chimeric PIV of the invention. In this context, many chimeric PIVs will include one or more, and preferably two or more, mutations from biologically derived PIV mutants, e.g., any one or combination of mutations identified in JS cp45. Preferred chimeric PIVs within the invention will incorporate a plurality and up to a full complement of the mutations present in JS cp45 or other biologically derived mutant PIV strains. Preferably, these mutations are stabilized against reversion in chimeric PIV by multiple nucleotide substitutions in a codon specifying each mutation.

Yet additional mutations that may be incorporated in chimeric PIV of the invention are mutations, e.g., attenuating mutations, identified in heterologous PIV or other non-segmented negative stranded RNA viruses. In particular, attenuating and other desired mutations identified in one negative stranded RNA virus may be "transferred", e.g., copied, to a corresponding position within the genome or antigenome of a chimeric PIV. Briefly, desired mutations in one heterologous negative stranded RNA virus are transferred to the chimeric PIV recipient (either in the vector genome or antigenome or in the heterologous donor gene or genome segment). This involves mapping the mutation in the heterologous mutant virus, identifying by routine sequence alignment the corresponding site in the recipient PIV, and mutating the native sequence in the PIV recipient to the mutant genotype (either by an identical or conservative mutation), as described in U.S. Provisional Patent Application Ser. No. 60/129,006, filed on Apr. 13, 1999, incorporated herein by reference. As this disclosure teaches, it is preferable to modify the recipient chimeric PIV genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution can be engineered at the corresponding residue(s) in the recombinant virus. Preferably the substitution will specify an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant PIV of the invention include other PIVs (e.g., HPIV1, HPIV2, HPIV3, BPIV and MPIV), RSV, Sendai virus (SeV), Newcastle disease virus (NDV), simian virus 5 (SV5), measles virus (MeV), rinderpest virus, canine distemper virus (CDV), rabies virus (RaV) and vesicular stomatitis virus (VSV), among others. A variety of exemplary mutations are disclosed, including but not limited to an amino acid substitution of phenylalanine at position 521 of the RSV L protein corresponding to and therefore transferable to a substitution of phenylalanine (or a conservatively related amino acid) at position 456 of the HPIV3 L protein. In the case of mutations marked by deletions or insertions, these can be introduced as corresponding deletions or insertions into the recombinant virus, however the particular size and amino acid sequence of the deleted or inserted protein fragment can vary.

Attenuating mutations in biologically derived PIV and other nonsegmented negative stranded RNA viruses for incorporation within chimeric PIV of the invention may occur naturally or may be introduced into wild-type PIV strains by well known mutagenesis procedures. For example, incompletely attenuated parental PIV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references. By "biologically derived PIV" is meant any PIV not produced by recombinant means. Thus, biologically derived PIV include all naturally occurring PIV, including, e.g., naturally occurring PIV having a wild-type genomic sequence and PIV having allelic or mutant genomic variations from a reference wild-type PIV sequence, e.g., PIV having a mutation specifying an attenuated phenotype. Likewise, biologically derived PIV include PIV mutants derived from a parental PIV by, inter alia, artificial mutagenesis and selection procedures.

As noted above, production of a sufficiently attenuated biologically derived PIV mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cp mutant or other partially attenuated PIV strain is adapted to efficient growth at a lower temperature by passage in culture. This selection of mutant PIV during cold-passage substantially reduces any residual virulence in the derivative strains as compared to the partially attenuated parent. Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene. The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

The JS cp45 HPIV3 mutant has been found to be relatively stable genetically, highly immunogenic, and satisfactorily attenuated. Nucleotide sequence analysis of this biologically derived virus, and of recombinant viruses incorporating various individual and combined mutations found therein, indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious PIV clones. This process coupled with evaluation of phenotype characteristics of parental and derivative viruses identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust chimeric PIV of the invention to an appropriate level of attenuation, immunogenicity, genetic resistance to reversion from an attenuated phenotype, etc., as desired. In accordance with the foregoing description, the ability to produce infectious PIV from cDNA permits introduction of specific engineered changes within chimeric PIV. In particular, infectious, recombinant PIVs are employed for identification of specific mutation(s) in biologically derived, attenuated PIV strains, for example mutations which specify ts, ca, att and other phenotypes. Desired mutations are thus identified and introduced into chimeric PIV vaccine strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific mutations associated with desired phenotypes, e.g., a cp or ts phenotype, into infectious chimeric PIV clones, the invention provides for other, site-specific modifications at, or within close proximity to, the identified mutation. Whereas most attenuating mutations produced in biologically derived PIVs are single nucleotide changes, other "site specific" mutations can also be incorporated by recombinant techniques into a chimeric PIV. As used herein, site-specific mutations include insertions, substitutions, deletions or rearrangements of from 1 to 3, up to about 5–15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a PIV clone, for example at or near a cis-acting regulatory sequence or nucleotide sequence encoding a protein active site, binding site, immunogenic epitope, etc. Site-specific PIV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant PIV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant PIV clone, yielding a PIV with greater genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5–10 and up to 15 nucleotides or more 5' or 3', relative to a targeted nucleotide position, e.g., to construct or ablate an existing cis-acting regulatory element.

In addition to single and multiple point mutations and site-specific mutations, changes to the chimeric PIV disclosed herein include deletions, insertions, substitutions or rearrangements of one or more gene(s) or genome segment(s). Particularly useful are deletions involving one or more gene(s) or genome segment(s), which deletions have been shown to yield additional desired phenotypic effects. Thus, U.S. patent application Ser. No. 09/350,821, filed by Durbin et al. on Jul. 9, 1999, incorporated herein by reference, describes methods and compositions whereby expression of one or more HPIV genes, for example one or more of the C, D, and/or V ORFs, is reduced or ablated by modifying the PIV genome or antigenome to incorporate a mutation that alters the coding assignment of an initiation codon or mutation(s) that introduce one or one or more stop codon(s). Alternatively, one or more of the C, D, and/or V ORFs can be deleted in whole or in part to render the corresponding protein(s) partially or entirely non-functional or to disrupt protein expression altogether. Chimeric PIV having such mutations in C, D, and/or V, or other non-essential gene(s), possess highly desirable phenotypic characteristics for vaccine development. For example, these modifications may specify one or more desired phenotypic changes including (i) altered growth properties in cell culture, (ii) attenuation in the upper and/or lower respiratory tract of mammals, (iii) a change in viral plaque size, (iv) a change in cytopathic effect, and (v) a change in immunogenicity. One exemplary "knock out" mutant PIV lacking C ORF expression, designated rC-KO, was able to induce a protective immune response against wild type HPIV3 challenge in a non-human primate model despite its beneficial attenuation phenotype.

Thus, in more detailed aspects of the instant invention, chimeric PIV incorporate deletion or knock out mutations in a C, D, and/or V ORF(s) or other non-essential gene which alters or ablates expression of the selected gene(s) or genome segment(s). This can be achieved, e.g., by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (e.g., growth, temperature restrictions on transcription, etc.). In more detailed aspects of the invention, chimeric PIVs are provided in which expression of one or more gene(s), e.g., a C, D, and/or V ORF(s), is ablated at the translational or transcriptional level without deletion of the gene or of a segment thereof, by, e.g., introducing multiple translational termination codons into a translational open reading frame (ORF), altering an initiation codon, or modifying an editing site. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described, to effectively preclude correcting mutations that may restore synthesis of a target protein. Several other gene knock-outs for the C, D, and/or V ORF(s) deletion and knock out mutants can be made using alternate designs and methods that are well known in the art (as described, for example, in (Kretschmer et al., *Virology* 216:309–316, 1996; Radecke et al., *Virology* 217:418–421, 1996; and Kato et al., *EMBO J.* 16:578–587, 1987; and Schneider et al., *Virology* 277:314–322, 1996, each incorporated herein by reference).

Nucleotide modifications that may be introduced into chimeric PIV constructs of the invention may alter small numbers of bases (e.g., from 15–30 bases, up to 35–50 bases or more), large blocks of nucleotides (e.g., 50–100, 100–300, 300–500, 500–1,000 bases), or nearly complete or complete genes (e.g., 1,000–1,500 nucleotides, 1,500–2,500 nucleotides, 2,500–5,000, nucleotides, 5,00–6,5000 nucleotides or more) in the vector genome or antigenome or heterologous, donor gene or genome segment, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In related aspects, the invention provides for supplementation of mutations adopted into a chimeric PIV clone from biologically derived PIV, e.g., cp and ts mutations, with additional types of mutations involving the same or different genes in a further modified PIV clone. Each of the PIV genes can be selectively altered in terms of expression levels, or can be added, deleted, substituted or rearranged, in whole or in part, alone or in combination with other desired modifications, to yield a chimeric PIV exhibiting novel vaccine characteristics. Thus, in addition to or in combination with attenuating mutations adopted from biologically derived PIV mutants, the present invention also provides a range of additional methods for attenuating or otherwise modifying the phenotype of a chimeric PIV based on recombinant engineering of infectious PIV clones. A variety of alterations can be produced in an isolated polynucleotide sequence encoding a targeted gene or genome segment, including a donor or recipient gene or genome segment in a chimeric PIV genome or antigenome for incorporation into infectious clones. More specifically, to achieve desired structural and phenotypic changes in recombinant PIV, the invention allows for introduction of modifications which delete, substitute, introduce, or rearrange a selected nucleotide or nucleotide sequence from a parent genome or antigenome, as well as mutations which delete, substitute, introduce or rearrange whole gene(s) or genome segment(s), within a chimeric PIV clone.

Thus provided are modifications in chimeric PIV of the invention which simply alter or ablate expression of a selected gene, e.g., by introducing a termination codon within a selected PIV coding sequence or altering its translational start site or RNA editing site, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s). In this context, any PIV gene or genome segment which is not essential for growth can be ablated or otherwise modified in a recombinant PIV to yield desired effects on virulence, pathogenesis, immunogenicity and other phenotypic characters. As for coding sequences, noncoding, leader, trailer and intergenic regions can be similarly deleted, substituted or modified and their phenotypic effects readily analyzed, e.g., by the use of minireplicons and recombinant PIV.

In addition, a variety of other genetic alterations can be produced in a PIV genome or antigenome for incorporation into a chimeric PIV, alone or together with one or more attenuating mutations adopted from a biologically derived mutant PIV, e.g., to adjust growth, attenuation, immunogenicity, genetic stability or provide other advantageous structural and/or phenotypic effects. These additional types of mutations are also disclosed in the foregoing incorporated references and can be readily engineered into chimeric PIV of the invention. For example, restriction site markers are routinely introduced within chimeric PIVs to facilitate cDNA construction and manipulation.

In addition to these changes, the order of genes in a chimeric PIV construct can be changed, a PIV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into chimeric PIV constructs of the invention include mutations directed toward cis-acting signals, which can be readily identified, e.g., by mutational analysis of PIV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which affect RNA replication or transcription. Any of these mutations can be inserted into a chimeric PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within chimeric PIVs of the invention may also include replacement of the 3' end of genome with its counterpart from antigenome, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315–324, 1996, incorporated herein by reference). Optimization by recombinant methods of the codon usage of the mRNAs encoding the HN and F proteins of PIV will provide improved expression for these genes.

In another exemplary embodiment, a sequence surrounding a translational start site (preferably including a nucleotide in the −3 position) of a selected PIV gene is modified, alone or in combination with introduction of an upstream start codon, to modulate PIV gene expression by specifying up- or down-regulation of translation. Alternatively, or in combination with other recombinant modifications disclosed herein, gene expression of a chimeric PIV can be modulated by altering a transcriptional GS or GE signal of any selected gene(s) of the virus. In alternative embodiments, levels of gene expression in a chimeric PIV vaccine candidate are modified at the level of transcription. In one aspect, the position of a selected gene in the PIV gene map can be changed to a more promoter-proximal or promotor-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel chimeric PIV vector virus having attenuated phenotypes, for example due to decreased expression of selected viral proteins involved in RNA replication, or having other desirable properties such as increased antigen expression.

In other embodiments, chimeric PIVs useful in vaccine formulations can be conveniently modified to accommodate antigenic drift in circulating virus. Typically the modification will be in the HN and/or F proteins. An entire HN or F gene, or a genome segment encoding a particular immunogenic region thereof, from one PIV strain or group is incorporated into a chimeric PIV genome or antigenome cDNA by replacement of a corresponding region in a recipient clone of a different PIV strain or group, or by adding one or more copies of the gene, such that multiple antigenic forms are represented. Progeny virus produced from the modified PIV clone can then be used in vaccination protocols against emerging PIV strains.

Replacement of a human PIV coding sequence or non-coding sequence (e.g., a promoter, gene-end, gene-start, intergenic or other cis-acting element) with a heterologous counterpart yields chimeric PIV having a variety of possible attenuating and other phenotypic effects. In particular, host range and other desired effects arise from substituting a bovine PIV (BPIV) or murine PIV (MPIV) protein, protein domain, gene or genome segment imported within a human PIV background, wherein the bovine or murine gene does not function efficiently in a human cell, e.g., from incompatibility of the heterologous sequence or protein with a biologically interactive human PIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into human PIV based on known aspects of bovine and human PIV structure and function.

In more detailed aspects, the invention provides methods for attenuating chimeric PIV vaccine candidates based on the further construction of chimeras between HPIV and a non-human PIV, for example HPIV3 and BPIV3 (e.g., as disclosed in U.S. Provisional Application Ser. No. 60/143,134 filed on Jul. 9, 1999, incorporated herein by reference). This method of attenuation is based on host range effects due to the introduction of one or more gene(s) or genome segment(s) of the non-human PIV into a human PIV vector-based chimeric virus. For example, there are numerous nucleotide and amino acid sequence differences between BPIV and HPIVs, which are reflected in host range differences. Between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., *J. Infect. Dis.* 157:655–662, 1988, incorporated herein by reference). Although the basis of the host range differences between HPIV3 and BPIV3 remains to be determined, it is likely that they will involve more than one gene and multiple amino acid differences. The involvement of multiple genes and possibly cis-acting regulatory sequences, each involving multiple amino acid or nucleotide differences, gives a very broad basis for attenuation, one which cannot readily be altered by reversion. This is in contrast to the situation with other live attenuated HPIV3 viruses which are attenuated by one or several point mutations. In this case, reversion of any individual mutation may yield a significant reacquisition of virulence or, in a case where only a single residue specified attenuation, complete reacquisition of virulence.

In exemplary embodiments of the invention, the vector genome or antigenome is an HPIV3 genome or antigenome, and the heterologous gene or genome segment is a N ORF derived from, alternatively, a Ka or SF strain of BPIV3 (which are 99% related in amino acid sequence). The N ORF of the HPIV3 background antigenome is substituted by the counterpart BPIV3 N ORF—yielding a novel recombinant chimeric PIV clone. Replacement of the HPIV3 N ORF of HPIV3 with that of BPIV3 Ka or SF results in a protein with approximately 70 amino acid differences (depending on the strain involved) from that of HPIV3 N. N is one of the more conserved proteins, and substitution of other proteins such as P, singly or in combination, would result in many more amino acid differences. The involvement of multiple genes and genome segments each conferring multiple amino acid or nucleotide differences provides a broad basis for attenuation which is highly stable to reversion.

This mode of attenuation contrasts sharply to HPIV vaccine candidates that are attenuated by one or more point mutations, where reversion of an individual mutation may yield a significant or complete reacquisition of virulence. In addition, several known attenuating point mutations in HPIV typically yield a temperature sensitive phenotype. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media. Thus, attenuation achieved solely by temperature sensitive mutations may not be ideal. In contrast, host range mutations present in chimeric PIV of the invention will not in most cases confer temperature sensitivity. Therefore, the novel method of PIV attenuation provided by these kinds of modifications will be more stable genetically and phenotypically and less likely to be associated with residual virulence in the upper respiratory tract compared to other known PIV vaccine candidates.

The above-incorporated reference discloses that both Ka and SF HPIV3/BPIV3 chimeric recombinants are viable and replicate as efficiently in cell culture as either HPIV3 or BPIV3 parent—indicating that the chimeric recombinants did not exhibit gene incompatibilities that restricted replication in vitro. This property of efficient replication in vitro is important since it permits efficient manufacture of this biological. Also, the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibit approximately a 60-fold or 30-fold reduction, respectively, in replication in the upper respiratory tract of rhesus monkeys compared to replication of HPIV3. Based on this finding, it is expected that other BPIV3 genes will also confer desired levels of host range restriction within chimeric PIV of the invention. Thus, according to the methods herein, a list of attenuating determinants will be readily identified in heterologous genes and genome segments of BPIV and other non-human PIVs that will confer, in appropriate combination, a desired level of host range restriction and immunogenicity on chimeric PIV selected for vaccine use.

In preferred chimeric vaccine candidates of the invention, attenuation marked by replication in the lower and/or upper respiratory tract in an accepted animal model for PIV replication in humans, e.g., hamsters or rhesus monkeys, may be reduced by at least about two-fold, more often about 5-fold, 10-fold, or 20-fold, and preferably 50–100-fold and up to 1,000-fold or greater overall (e.g., as measured between 3–8 days following infection) compared to growth of the corresponding wild-type or mutant parental PIV strain.

Infectious chimeric PIV vector clones of the invention can also be engineered according to the methods and compositions disclosed herein to enhance immunogenicity and induce a level of protection greater than that provided by infection with a wild-type, parental (i.e., vector or heterologous donor) PIV or non-PIV pathogen. For example, one or more supplemental immunogenic epitope(s), protein domains, or proteins from a heterologous PIV strain or type, or from a non-PIV pathogen such as measles or RSV, can be added to a chimeric PIV by appropriate nucleotide changes in the chimeric genome or antigenome. Alternatively, chimeric PIVs of the invention can be engineered to add or ablate (e.g., by amino acid insertion, substitution or deletion) immunogenic proteins, protein domains, or forms of specific proteins associated with desirable or undesirable immunological reactions.

Within the methods of the invention, additional genes or genome segments may be inserted into or proximate to the chimeric PIV vector genome or antigenome. These genes may be under common control with recipient genes, or may be under the control of an independent set of transcription signals. In addition to genes and genome segments encoding antigenic determinants, genes of interest in this context include genes encoding cytokines, for example, an interleukin (e.g., interleukin 2 (IL-2), interleukin 4 (IL-4), interleukin 5 (IL-5), interleukin 6 (IL6), interleukin 18 (IL-18)), tumor necrosis factor alpha (TNFα), interferon gamma (IFNγ), or granulocyte-macrophage colony stimulating factor (GM-CSF), as well as IL-2 through IL-18, especially IL-2, IL-6 and IL-12, and IL-18, gamma-interferon (see, e.g., U.S. Provisional Application Ser. No. 60/143,425 filed Jul. 13, 1999, incorporated herein by reference). Coexpression of these additional proteins provides the ability to modify and improve immune responses against chimeric PIV of the invention both quantitatively and qualitatively.

Deletions, insertions, substitutions and other mutations involving changes of whole viral genes or genome segments within chimeric PIV of the invention yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578–87, 1997, incorporated herein by reference). Ablation of such genes in vaccine viruses is expected to reduce virulence and pathogenesis and/or improve immunogenicity.

Introduction of the foregoing defined mutations into an infectious, chimeric PIV clone can be achieved by a variety of well known methods. By "infectious clone" with regard to DNA is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the PIV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of a PIV genome or antigenome is cloned into the plasmid pTZ18U, and used to transform CJ236 cells (Life Technologies, Gaithersburg, Md.). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The invention also provides methods for producing infectious chimeric PIV from one or more isolated polynucleotides, e.g., one or more cDNAs. According to the present invention cDNA encoding a PIV genome or antigenome is constructed for intracellular or in vitro coexpression with the necessary viral proteins to form infectious PIV. By "PIV antigenome" is meant an isolated positive-sense polynucleotide molecule which serves as the template for the synthesis of progeny PIV genome. Preferably a cDNA is constructed which is a positive-sense version of the PIV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, and L proteins.

For purposes of the present invention the genome or antigenome of the recombinant PIV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant PIV is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from cDNA-expressed genome or antigenome, the genome or antigenome is coexpressed with those PIV proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Infectious PIV of the invention are produced by intracellular or cell-free coexpression of one or more isolated polynucleotide molecules that encode a PIV genome or antigenome RNA, together with one or more polynucleotides encoding viral proteins necessary to generate a transcribing, replicating nucleocapsid. Among the viral proteins useful for coexpression to yield infectious PIV are the major nucleocapsid protein (N) protein, nucleocapsid phosphoprotein (P), large (L) polymerase protein, fusion protein (F), hemagglutinin-neuraminidase glycoprotein (HN), and matrix (M) protein. Also useful in this context are products of the C, D and V ORFs of PIV.

cDNAs encoding a PIV genome or antigenome are constructed for intracellular or in vitro coexpression with the necessary viral proteins to form infectious PIV. By "PIV antigenome" is meant an isolated positive-sense polynucleotide molecule which serves as a template for synthesis of progeny PIV genome. Preferably a cDNA is constructed which is a positive-sense version of the PIV genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant PIV (rPIV) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant PIV" is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from a cDNA-expressed PIV genome or antigenome, the genome or antigenome is coexpressed with those PIV N, P and L proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins.

In certain embodiments of the invention, complementing sequences encoding proteins necessary to generate a transcribing, replicating PIV nucleocapsid are provided by one or more helper viruses. Such helper viruses can be wild type or mutant. Preferably, the helper virus can be distinguished phenotypically from the virus encoded by the PIV cDNA. For example, it is desirable to provide monoclonal antibodies which react immunologically with the helper virus but not the virus encoded by the PIV cDNA. Such antibodies can be neutralizing antibodies. In some embodiments, the antibodies can be used in affinity chromatography to separate the helper virus from the recombinant virus. To aid the procurement of such antibodies, mutations can be introduced into the PIV cDNA to provide antigenic diversity from the helper virus, such as in the HN or F glycoprotein genes.

In alternate embodiments of the invention, the N, P, L and other desired PIV proteins are encoded by one or more non-viral expression vectors, which can be the same or separate from that which encodes the genome or antigenome. Additional proteins may be included as desired, each encoded by its own vector or by a vector encoding one or more of the N, P, L and other desired PIV proteins, or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210: 202–205 (1995), incorporated herein by reference in its entirety). The viral proteins, and/or T7 RNA polymerase, can also be provided by transformed mammalian cells or by transfection of preformed mRNA or protein.

A PIV antigenome may be constructed for use in the present invention by, e.g., assembling cloned cDNA segments, representing in aggregate the complete antigenome, by polymerase chain reaction or the like (PCR; described in, e.g., U.S. Pat. Nos. 4,683,195 and 4,683,202, and PCR Protocols: *A Guide to Methods and Applications*, Innis et al., eds., Academic Press, San Diego (1990), each incorporated herein by reference in its entirety) of reverse-transcribed copies of PIV mRNA or genome RNA. For example, a first construct is generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type (e.g., Grosfeld et al., (1995), supra), which would yield a 3' end containing a single nonviral nucleotide, or can be any of the other suitable ribozymes such as that of hepatitis delta virus (Perrotta et al., *Nature* 350:434–436, 1991), incorporated herein by reference in its entirety) which would yield a 3' end free of non-PIV nucleotides. The left- and right-hand ends are then joined via a common restriction site.

A variety of nucleotide insertions, deletions and rearrangements can be made in the PIV genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Alternative means to construct cDNA encoding the genome or antigenome include reverse transcription-PCR using improved PCR conditions (e.g., as described in Cheng et al., *Proc. Natl. Acad. Sci. USA* 91:5695–5699 (1994)), incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the larger size genome or antigenome.

Isolated polynucleotides (e.g., cDNA) encoding the genome or antigenome may be inserted into appropriate host cells by transfection, electroporation, mechanical insertion, transduction or the like, into cells which are capable of supporting a productive PIV infection, e.g., HEp-2, FRhL- DBS2, LLC-MK2, MRC-5, and Vero cells. Transfection of isolated polynucleotide sequences may be introduced into cultured cells by, for example, calcium phosphate-mediated transfection (Wigler et al., *Cell* 14: 725 (1978); Corsaro and Pearson, *Somatic Cell Genetics* 7: 603 (1981); Graham and Van der Eb, *Virology* 52: 456 (1973)), electroporation (Neumann et al., *EMBO J.* 1: 841–845 (1982)), DEAE-dextran mediated transfection (Ausubel et al., (ed.) *Current Protocols in Molecular Biology*, John Wiley and Sons, Inc., NY (1987), cationic lipid-mediated transfection (Hawley-Nelson et al., *Focus* 15: 73–79 (1993)) or a commercially available transfection regent, e.g., LipofectACE® (Life Technologies) or the like (each of the foregoing references are incorporated herein by reference in its entirety).

As noted above, in some embodiments of the invention the N, P, L and other desired PIV proteins are encoded by one or more helper viruses which is phenotypically distinguishable from that which encodes the genome or antigenome. The N, P, L and other desired PIV proteins can also be encoded by one or more expression vectors which can be the same or separate from that which encodes the genome or antigenome, and various combinations thereof. Additional proteins may be included as desired, encoded by its own vector or by a vector encoding one or more of the N, P, L and other desired PIV proteins, or the complete genome or antigenome.

By providing infectious clones of PIV the invention permits a wide range of alterations to be recombinantly produced within the PIV genome (or antigenome), yielding defined mutations which specify desired phenotypic changes. By "infectious clone" is meant cDNA or its product, synthetic or otherwise, RNA capable of being directly incorporated into infectious virions which can be transcribed into genomic or antigenomic RNA capable of serving as a template to produce the genome of infectious viral or subviral particles. As noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA subjects provide for better ease of manipulation than large cDNA subjects, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen® kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding an PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15–35 nucleotides in the case of genome segments encoding small functional domains of proteins, e.g., epitopic sites, to about 50, 75, 100, 200–500, and 500–1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock, et al., *J. Virol.* 67: 2772–8 (1993), incorporated herein by reference in its entirety), whose rescue-dependent status is useful in characterizing those mutants that may be too inhibitory to be recovered in replication-independent infectious virus.

Certain substitutions, insertions, deletions or rearrangements of genes or genome segments within recombinant PIV of the invention (e.g., substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, genome segments, proteins or protein regions, are typically from heterologous sources (e.g., from different PIV genes, or representing the same (i.e., homologous or allelic) gene or genome segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding genome segments embrace an assemblage of species having a range of size and sequence variations defined by a common biological activity among the domain or genome segment variants.

Counterpart genes and genome segments, as well as other polynucleotides disclosed herein for producing recombinant PIV within the invention, often share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant PIV of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis (2nd ed., E. S. Golub & D. R. Gren, eds., Sinauer Associates, Sunderland, Mass., 1991), incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). Moreover, amino acids may be modified by glycosylation, phosphorylation and the like.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. The recombinant PIV of the invention are not only viable and more appropriately attenuated than previous vaccine candidates, but are more stable genetically in vivo—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like.

Recombinant PIV of the invention can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV vaccine candidates are widely accepted in the art, and the data obtained therefrom correlate well with PIV infection, attenuation and immunogenicity in humans.

In accordance with the foregoing description, the invention also provides isolated, infectious recombinant PIV compositions for vaccine use. The attenuated virus which is a component of a vaccine is in an isolated and typically purified form. By isolated is meant to refer to PIV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated PIV of the invention may be produced by an infected cell culture, separated from the cell culture and added to a stabilizer.

For vaccine use, recombinant PIV produced according to the present invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, $Mg^{++}$ and HEPES, with or without adjuvant, as further described below.

PIV vaccines of the invention contain as an active ingredient an immunogenically effective amount of PIV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a PIV composition as described herein, via aerosol, droplet, oral, topical or other route, the immune system of the host responds to the vaccine by producing antibodies specific for PIV proteins, e.g., F and HN glycoproteins. As a result of the vaccination with an immunogenically effective amount of PIV produced as described herein, the host becomes at least partially or completely immune to PIV infection, or resistant to developing moderate or severe PIV infection, particularly of the lower respiratory tract.

The host to which the vaccines are administered can be any mammal which is susceptible to infection by PIV or a closely related virus and which host is capable of generating a protective immune response to the antigens of the vaccinizing strain. Accordingly, the invention provides methods for creating vaccines for a variety of human and veterinary uses.

The vaccine compositions containing the PIV of the invention are administered to a host susceptible to or otherwise at risk for PIV infection to enhance the host's own immune response capabilities. Such an amount is defined to be a "immunogenically effective dose." In this use, the precise amount of PIV to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the vaccine formulations should provide a quantity of modified PIV of the invention sufficient to effectively protect the host patient against serious or life-threatening PIV infection.

The PIV produced in accordance with the present invention can be combined with viruses of other PIV serotypes or strains to achieve protection against multiple PIV serotypes or strains. Alternatively, protection against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may protect against different strains of the same or different serotype.

In some instances it may be desirable to combine the PIV vaccines of the invention with vaccines which induce protective responses to other agents, particularly other childhood viruses. In another aspect of the invention the PIV can be employed as a vector for protective antigens of other pathogens, such as respiratory syncytial virus (RSV) or measles virus, by incorporating the sequences encoding those protective antigens into the PIV genome or antigenome which is used to produce infectious PIV, as described herein.

In all subjects, the precise amount of recombinant PIV vaccine administered, and the timing and repetition of administration, will be determined based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the vaccine formulations should provide a quantity of attenuated PIV sufficient to effectively stimulate or induce an anti-PIV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated PIV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered PIV strain expressing a cytokine or an additional protein rich in T cell epitopes may be particularly advantageous for adults rather than for infants.

PIV vaccines produced in accordance with the present invention can be combined with viruses expressing antigens of another subgroup or strain of PIV to achieve protection against multiple PIV subgroups or strains. Alternatively, the vaccine virus may incorporate protective epitopes of multiple PIV strains or subgroups engineered into one PIV clone, as described herein.

The PIV vaccines of the invention elicit production of an immune response that is protective against serious lower respiratory tract disease, such as pneumonia and bronchiolitis when the individual is subsequently infected with wild—type PIV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred PIV vaccine candidates of the invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of PIV vaccine candidates may be determined by, for example, quantifying the amount of virus present in the respiratory tract of an immunized host and comparing the amount to that produced by wild-type PIV or other attenuated PIV which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of PIV in the nasopharynx of an infected host are well known in the literature.

Levels of induced immunity provided by the vaccines of the invention can also be monitored by measuring amounts of neutralizing secretory and serum antibodies. Based on these measurements, vaccine dosages can be adjusted or vaccinations repeated as necessary to maintain desired levels of protection. Further, different vaccine viruses may be advantageous for different recipient groups. For example, an engineered PIV strain expressing an additional protein rich in T cell epitopes may be particularly advantageous for adults rather than for infants.

In yet another aspect of the invention the PIV is employed as a vector for transient gene therapy of the respiratory tract. According to this embodiment the recombinant PIV genome or antigenome incorporates a sequence which is capable of encoding a gene product of interest. The gene product of interest is under control of the same or a different promoter from that which controls PIV expression. The infectious PIV produced by coexpressing the recombinant PIV genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant PIV is administered in, an amount sufficient to result in the expression of therapeutic or prophylactic levels of the desired gene product. Representative gene products which may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation. These examples document construction of representative chimeric PIVs bearing one or more heterologous antigenic determinant(s) according to the above described methods. In one example, the HA gene of the measles virus is inserted as an extra gene into one of three gene junctions of a JS wild type or attenuated strain of HPIV3, namely, the N/P, P/M, or HN/L junction, and recombinant chimeric viruses were recovered. Insertion of the measles HA gene at three different positions in the HPIV3 genome illustrates the range of useful constructs for transferring antigenic determinants from foreign pathogens into PIV vectors. Further, it is expected that inserted gene units that are more 3'-leader proximal will be transcribed and expressed at higher levels than the same gene units located more distally, which will allow for closer modulation of heterologous gene expression (Collins et al., 3rd ed. In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1205–1243. Lippincott-Raven Publishers, Philadelphia, 1996).

The chimeric rHPIV bearing the measles virus HA insertion in a wild type rHPIV3 background replicated efficiently in vitro but was restricted in replication in hamsters compared to that of the rHPIV3 virus from which it was derived. Similarly, the recombinant chimeric HPIV3 bearing the measles virus HA insertion in an attenuated rHPIV3 background replicated in vitro and in hamsters to a level that was also slightly less than that of the attenuated rHPIV3cp45L mutant virus from which it was derived. The amount of HA protein expressed by cells infected with the attenuated rHPIV3-measles virus HA recombinants with the HA gene in the N/P or P/M junction was very high and even exceeded that seen in cells infected with native measles virus. The level of replication of the rHPIV3cp45L with a measles virus HA insert in the N/P or P/M junction was 10-fold lower in the upper respiratory tract of the hamster than that of the rHPIV3-cp45L parent virus indicating that gene insertions can unexpectedly contribute to the attenuation of an HPIV3 vector. These results which identify a unique host range phenotype are unexpected.

Importantly, infection of hamsters with each recombinant chimeric virus tested induced high levels of antibody to both HPIV3 and to measles virus. Animals immunized with the attenuated recombinant chimeric HPIV3 carrying the HA insertion were highly resistant to replication of HPIV3 challenge virus. While the wild type measles virus does not replicate efficiently in hamsters and thus cannot be used in challenge study, the protective efficacy of the attenuated recombinant chimeric vaccine is readily apparent from the high levels of neutralizing antibody induced. These levels are associated with a high level of resistance to measles in humans (Chen et al., *J. Infect. Dis.* 1.62:1036–42, 1990).

It is further demonstrated in the examples that attenuated chimeric recombinant HPIV vectors, combining a backbone of HPIV3 and one or more antigenic determinants of HPIV1, can also be used as vectors to express additional foreign antigens (e.g., of HPIV2 or a non-PIV virus). This aspect of the invention takes advantage of the efficient growth and excellent attenuation properties of the HPIV3 backbone to carry antigenic determinants of multiple heterologous pathogens, as exemplified by HPIV1 and HPIV2. The cDNA encoding rPIV3-1 (a non-attenuated recombinant bearing major antigens of HPIV1) or rPIV3-1cp45 (an attenuated recombinant bearing HPIV1 major antigens) was modified by the insertion of a gene unit containing the ORF of HPIV2 HN gene between the gene units containing the F and HN ORFs of HPIV1. The recombinant chimeric viruses, designated rPIV3-1.2HN and rPIV3-1cp45.2HN, were readily recovered and replicated efficiently in tissue culture. Each virus exhibited a level of temperature sensitivity of replication in vitro similar to that of its rPIV3-1 or rPIV3-1cp45 parent virus. The insertion of the PIV2 HN attenuated both the rPIV3-1 and rPIV3-cp45 viruses in hamsters, a finding similar to that observed with the insertion of the measles viruses HA into rJS and into rPIV3cp45. Infection of hamsters with these antigenic rPIV3-1 recombinants bearing the PIV2 HN gene insert induced serum antibody responses reactive against both HPIV1 and HPIV2.

Thus, it is possible to use an attenuated rHPIV3 or rHPIV3-1 vaccine candidate as a vector to infect the respiratory tract of susceptible hosts and thereby induce a vigorous antibody response to foreign protective antigens expressed from an extra gene unit, as well as against the HPIV vector itself. The presence of three antigenic serotypes of HPIV, which do not provide significant cross-protection, allows for more effective, sequential immunization of human infants with antigenically distinct variants of HPIV each bearing the same or different heterologous antigenic determinant(s), e.g., a protective antigen, antigenic domain or epitope of measles virus or of one or more different viral or microbial pathogens. Sequential immunization permits development of a primary immune response to the foreign protein, =which is boosted during subsequent infections with a secondary, antigenically-distinct HPIV bearing one or more heterologous antigenic determinants, e.g., a protective antigen, antigenic domain or epitope of measles virus or of one or more different viral or microbial pathogens. In this way, the immunity induced to one HPIV vector can be circumvented by boosting with an antigenically distinct HPIV vector. In this context, successful immunization of animals that are immune to PIV3 has been achieved with attenuated PIV3-1 vaccine candidates, confirming the feasibility of sequential immunization with serotypically distinct PIV viruses even if these PIVs share proteins other than HN and F. (Tao et al., *Vaccine* 17:1100–8, 1999). In this study, the immunogenicity and efficacy of rPIV3-1.cp45L against PIV1 challenge was examined in hamsters with and without prior immunity to PIV3. rPIV3-1.cp45L efficiently infected hamsters previously infected with wild type or attenuated PIV3, but there was approximately a five-fold reduction in replication of rPIV3-1.cp45L virus in the PIV3-immune animals. However, rPIV3-1.cp45L immunization of PIV3-immune animals induced a vigorous serum antibody response to PIV1 and reduced replication of PIV1 challenge virus 1000-fold in the lower respiratory tract and 200-fold in the upper respiratory tract. These results demonstrate that the recombinant chimeric rPIV3-1.cp45L candidate vaccine can induce immunity to PIV1 even in animals immune to PIV3. This establishes the feasibility of employing a sequential immunization schedule in which a recombinant chimeric rPIV3-1.cp45L or other PIV vaccine virus is given following a live attenuated PIV3 vaccine. since rPIV3-1.cp45L readily induced protective immunity against itself, it would also induce an effective immune response to any vectored protective antigen that it was carrying. Also, the PIVs and RSV have the unusual property of being able to reinfect the respiratory tract, although reinfections typically are not associated with serious disease. Thus, vector based vaccine constructs of the invention are useful to boost immune responses by a second, third or fourth administration of the same HPIV vector or by sequential use of different vectors.

In preferred sequential vaccination methods of the invention, it is desirable to sequentially immunize an infant with different PIV vectors each expressing the same heterologous antigenic determinant such as the measles virus HA. This sequential immunization permits the induction of the high titer of antibody to the heterologous protein that is characteristic of the secondary antibody response. In one embodiment, early infants (e.g. 2–4 month old infants) are immunized with an attenuated chimeric HPIV3 expressing a heterologous antigenic determinant, for example the measles virus HA protein, and also adapted to elicit an immune response against HPIV3. One exemplary vaccine candidate useful in this context is the rcp45L(HA P-M) recombinant. Subsequently, e.g., at four months of age the infant is again immunized but with a different, secondary PIV vector construct antigenically distinct from the first. An exemplary vaccine candidate in this context is the rPIV3-1 cp45L virus expressing the measles virus HA gene and HPIV1 antigenic determinants as functional, obligate glycoproteins of the vector. Following the first vaccination, the vaccinee will elicit a primary antibody response to both the PIV3 HN and F proteins and to the measles virus HA protein, but not to the PIV1 HN and F protein. Upon secondary immunization with the rPIV3-1 cp45L expressing the measles virus HA, the vaccinee will be readily infected with the vaccine because of the absence of antibody to the PIV1 HN and F proteins and will develop both a primary antibody response to the PIV1 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric vaccine viruses disclosed herein, simultaneous with stimulation of an initial and then secondary, high titer protective response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype.

Further in accordance with this aspect of the invention, exemplary coordinate vaccination protocols may incorporate two, three, four and up to six or more separate chimeric HPIV vaccine viruses administered simultaneously (e.g., in a polyspecific vaccine mixture) in a primary vaccination step, e.g., at one, two or four months of age. For example, two or more and up to a full panel of HPIV-based vaccine viruses can be administered that separately express one or more antigenic determinants (i.e., whole antigens, immunogenic domains, or epitopes) selected from the G protein of RSV subgroup A, the F protein of RSV subgroup A, the G protein of RSV subgroup B, the F protein of RSV subgroup B, the HA protein of measles virus, and/or the F protein of measles virus. Coordinate booster administration of these same PIV3-based vaccine constructs can be repeated at two months of age. Subsequently, e.g., at four months of age, a separate panel of 2–6 or more antigenically distinct (referring to vector antigenic specificity) live attenuated HPIV-based vaccine viruses can be administered in a secondary vaccination step. For example, secondary vaccination may involve concurrent administration of a mixture or multiple formulations that contain(s) multiple HPIV3-1 vaccine constructs that collectively express RSV G from subgroup A, RSV F from subgroup A, RSV F from subgroup B, RSV G from subgroup B, measles virus HA, and/or measles virus F, or antigenic determinants from any combination of these proteins. This secondary immunization provides a boost in immunity to each of the heterologous RSV and measles virus proteins or antigenic determinant(s) thereof. At six months of age, a tertiary vaccination step involving administration of one-six or more separate live attenuated PIV3-2 vector-based vaccine recombinants can be coordinately administered that separately or collectively express RSV G from subgroup A, RSV F from subgroup A, RSV G from subgroup B, RSV F from subgroup B, measles virus HA, and/or measles virus F, or antigenic determinant(s) thereof. Optionally at this step in the vaccination protocol, rPIV3 and rPIV3-1 vaccines may be administered in booster formulations. In this way, the strong immunity characteristic of secondary antibody to PIV1, PIV2, PIV3, RSV A, RSV B, and measles viruses are all induced within the first six months of infancy. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

In other aspects of the invention, insertion of heterologous nucleotide sequences into HPIV vaccine candidates are employed separately to modulate the level of attenuation of candidate vaccine recombinants, e.g., for the upper respiratory tract. Thus, it is possible to insert nucleotide sequences into a rHPIV that both direct the expression of a foreign protein and that attenuate the virus in an animal host, or to use nucleotide insertions separately to attenuate candidate vaccine viruses. To define some of the rules that govern the effect of gene insertion on attenuation, gene units of varying lengths were inserted into a wild type HPIV3 backbone and the effects of gene unit length on attenuation were examined. These novel gene unit insertions were engineered to not contain a significant ORF which permitted an evaluation of the effect of gene unit length independently of an effect of the expressed protein of that gene. These heterologous sequences were inserted as an extra gene unit of sizes between 168 nt and 3918 nt between the HN and L genes. In addition, control cDNA constructions and viruses were made in which insertions of similar sizes were placed in the 3'-noncoding region of the HN gene and hence did not involve the addition of an extra gene. These viruses were made to assess the effect of an increase in the overall genome length and in gene number on attenuation. The insertion of an extra gene unit is expected to decrease the transcription of genes downstream of the insertion site which will affect both the overall abundance and ratios of the expressed proteins. As demonstrated herein, gene insertions or extensions larger than about 3000 nts in length attenuated the wild type virus for the upper and lower respiratory tract of hamsters. Gene insertions of about 2000 nts in length further attenuated the rHPIV3cp45L vaccine candidate for the upper respiratory tract. In summary, gene insertions can have the dual effect of both attenuating a candidate vaccine virus and inducing a protective effect against a second virus. Gene extensions in the 3'-noncoding region of a gene, which cannot express additional proteins, can also be attenuating in and of themselves. Within these methods of the invention, gene insertion length is a determinant of attenuation.

GU and NCR insertions within recombinant PIV of the invention produce an attenuation phenotype characterized by efficient replication in vitro and decreased replication in vivo, a phenotype not previously described for other paramyxovirus insertions. The mechanism of attenuation resulting from a GU insertion may result from one or more of the following factors acting predominantly in vivo. The addition of an extra gene unit may decrease the level of transcription of downstream genes since there is a transcriptional gradient in which more promoter-proximal genes are transcribed at a higher rate than the more promoter-distal genes. The decreased expression of the downstream gene products resulting from the decreased abundance of their mRNAs could result in attenuation if their gene product is limiting or if a specific ratio of gene products that is required for efficient replication is altered. It is thought that the transcription gradient is a consequence of the transcriptase complex falling off the template during transcription as well as during the transfer across gene junctions. Alternatively, the increase in the overall length of the genome and the extra mRNAs transcribed may increase the level of viral double stranded RNA made which in turn may induce a higher level of the antiviral activity of the interferon system. Finally, the overall level of genome replication may be reduced due to the increase in length of the genome and the antigenome. This may result from a disengagement of replicas complexes from the template during replication of the genomic RNA or antigenomic RNA. The decreased amount of genome available for packaging into virions may result in a decrease in virus yield which results in attenuation.

The mechanism of attenuation resulting from a NCR insertion may result from one or more of the following factors. The extra length of the 3'-end of HN mRNA resulting from the NCR insertion may contribute to the instability of the mRNA and lead to a decrease in the expression of the HN protein. Alternatively, the increase in the overall length of the genome and the extra length of the HN mRNA may increase the level of viral double stranded RNA made that can induce a higher level of the antiviral activity of the interferon system. Alternatively or additionally, the overall level of genome replication may be reduced due to the increase in length of the genome and the antigenome. This may result from a disengagement of replicas complexes from the template during replication of the genomic RNA or antigenomic RNA. The decreased amount of genome available for packaging into virions could result in a decrease in virus yield which results in attenuation. Finally, the addition of extra nucleotides to the 3' end of the HN gene could decrease the level of transcription of downstream genes since the transcriptase complex could fall off the template during transcription of the extra nucleotides at the 3' end of the HN gene.

The in vitro and in vivo growth properties of the GU and NCR insertions into PIV3 are distinct from previous findings with other single-stranded, negative-sense RNA viruses, cited above. Previously tested insertions examined expressed proteins, whereby the independent effect of the length of insertions on viral growth in vivo cannot be determined. The present findings demonstrate that the GU and NCR insertions greater than 3% b specify an attenuation phenotype that is independent of expressed protein. Shorter insertions, e.g., greater than about 2% b, specify further attenuation in a partially attenuated recipient. Also unexpectedly, the GU and NCR insertions specify restricted replication in vivo in the absence of restricted replication in vitro. In addition, the attenuation phenotype in vivo is seen when the insertion is either in the form of a GU or a NCR insertion—other documented insertions are in the form of GU only. Thus, the attenuation of replication in vivo specified by a GU or NCR insertion that does not encode a protein represents a unique way to attenuate members of the Mononegavirales in vivo.

EXAMPLE I

Construction of cDNAs Encoding a Chimeric HPIV3/Measles Virus-HA Antigenome and Recovery of Infectious Virus The full-length cDNA clones, p3/7(131)2G+, encoding the complete 15462 nucleotide antigenome of the JS PIV3 wt virus, and pFLCcp45L, which encodes the antigenome of the derivative of JS wt containing three cp45-specific temperature-sensitive mutations in the L ORF of PIV3, have been previously described (Durbin et al., *Virology* 235: 323–332, 1997a; Skiadopoulos et al., *J. Virol.* 72:1762–8, 1998, each incorporated herein by reference). These clones were used as vectors for the insertion of the HA gene of measles virus to create both wildtype and attenuated HPIV3 chimeric constructs which express a heterologous antigenic determinant, exemplified by the HA protein, of measles virus. The size of each insert containing the HA gene of measles was a multiple of six such that the chimeric virus recovered from the cDNA would conform to the rule of six (Durbin et al., *Virology* 234:74–83, 1997b, incorporated herein by reference).

Construction of Full-Length Chimeric HPIV3 cDNAs Encoding the HA Protein of Measles Virus in the N/P or P/M Junctions.

The PmlI to BamHI fragment of p3/7(131)2G+ (nt 1215–3903 of the PIV3 antigenome) was subcloned into the plasmid pUC119 {pUC119(PmlI-BamHI)} which had been modified to include a PmlI site in the multiple cloning region. Two independent single-stranded mutagenesis reactions were performed on pUC119(PmlI-BamHI) using Kunkel's method (Kunkel et al., *Methods Enzymol.* 154: 367–382, 1987, incorporated herein by reference); the first reaction introduced an Af/II site in the 3' (downstream)-noncoding region of the N gene by mutating the CTAAAT (SEQ ID NO: 7) sequence at nts 1677–1682 of the antigenome to CTTAAG (SEQ ID NO: 8) (pAf/II N-P), and the second, separate, reaction introduced an Af/II site in the in the 3'-noncoding region of the P gene by mutating the TCAATC sequence at nts 3693–3698 of the antigenome to CTTAAG (SEQ ID NO:8) (pAf/II P-M).

Figure 1A:
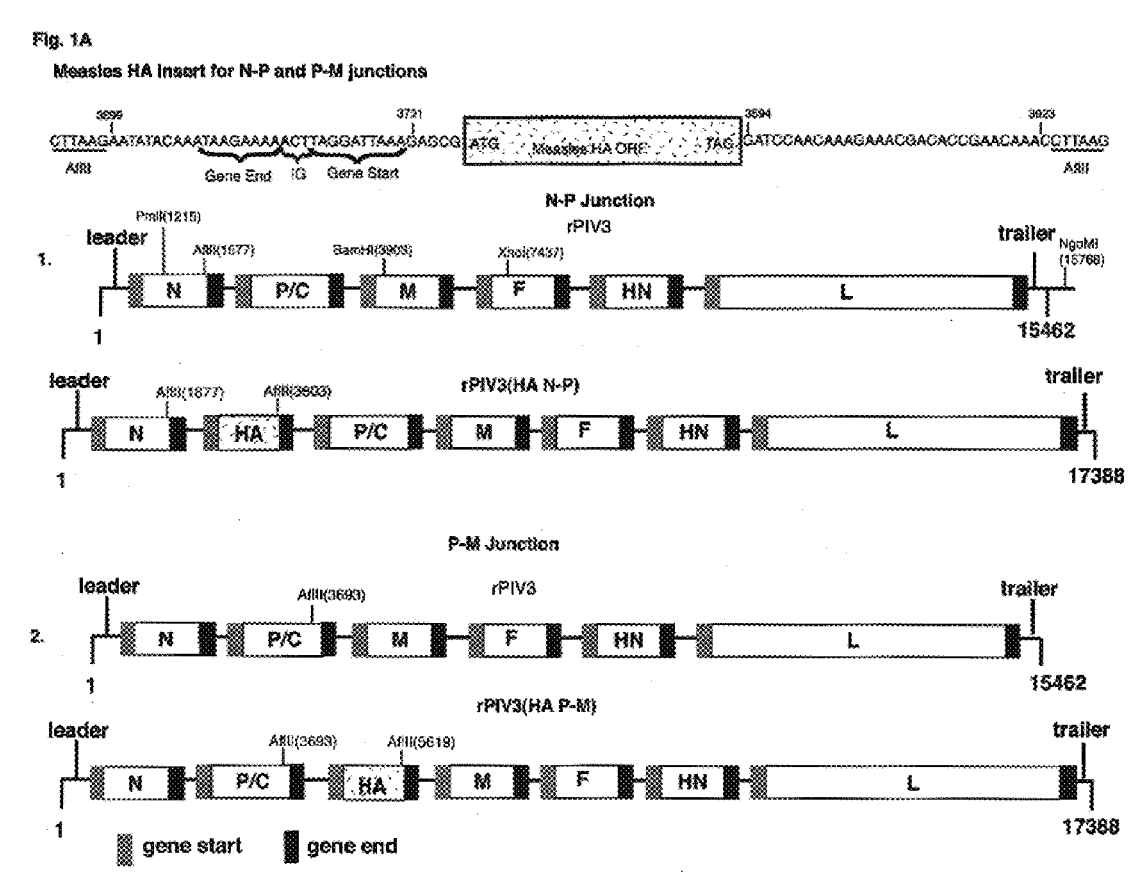

The HA ORF of measles virus Edmonston strain was amplified from Edmonston wild type virus by reverse transcription polymerase chain reaction (RT-PCR). The nt sequence of the Edmonston wild type HA open reading frame (ORF) is in GenBank Accession # U03669, incorporated herein by reference (note that this sequence is the ORF only without the upstream 3 nts or the stop codon). Measles virus RNA was purified from clarified medium using TRIzol-LS (Life Technologies, Gaithersburg, Md.) following the manufacturer's recommended procedure. RT-PCR was performed with the Advantage RT-for-PCR and Advantage-HF PCR kits (Clontech, Palo Alto, Calif.) following the recommended protocols. Primers were used to generate a PCR fragment spanning the entire ORF of the measles virus HA gene flanked by PIV3 non-coding sequence and Af/II restriction sites. The forward primer 5'-TTAATCTT AAGAATATACAAATAAGAAAAACTTAGGATTAAA-GAGCGATGTCACC ACAACGAGACCGGATAAATGC-CTTCTAC-3' (SEQ ID NO: 10) encodes an Af/II site (italicized) upstream of PIV3 noncoding sequence derived from the N/P gene junction-nts 3699–3731 (underlined), containing GE, IG and GS sequences (FIG. 1A) and the beginning of the measles HA ORF (bolded) preceded by three non-HPIV3, non-measles virus nts designated in the primer. The reverse primer 5'-ATTATTGCTTAAG GTTTGTTCGGTGTCGTTTCTTTGTTGGATCCTATCT-GCGATTGG TTCCATCTTC-3' (SEQ ID NO: 11) encodes an Af/II site (italicized) downstream (in the positive-sense complement) of PIV3 noncoding sequence derived from the P gene, nt 3594–3623 (underlined), and the end of the measles HA ORF (bolded). The resultant PCR fragment was then digested with Af/II and cloned into p(Af/II N-P) and p(Af/II P-M) to create pUC119(HA N-P) and pUC119(HA P-M) respectively. pUC119(HA N-P) and pUC119(HA P-M) were sequenced over the entire Af/II insert using dRhodamine Terminator Cycle Sequencing Ready Reaction (ABI prism, PE Applied Biosystems, Foster city, CA), and the sequence was confirmed to be correct.

The PmlI to BamHI fragments of pUC119(HA N-P) and pUC119(HA P-M) were separately cloned into the full-length antigenome cDNA plasmid p3/7(131)2G+ as previously described (Durbin et al., *Virology* 235:323–332, 1997a, incorporated herein by reference) to create pFLC(HA N-P) and pFLC(HA P-M) (FIG. 1). The XhoI-NgoMI fragment (nt 7437–15929) of pFLCcp45L was then cloned into the XhoI-NgoMI window of both pFLC(HA N-P) and pFLC(HA P-M) to create pFLCcp45L(HA N-P) and pFLCcp45L(HA P-M). pFLCcp45L encodes the three amino acid changes in the L gene of PIV3 cp45 (aa position 942, 992, and 1558) which confer most of the temperature-sensitivity and attenuation of the cp45 vaccine candidate virus (Skiadopoulos et al., *J. Virol.* 72:1762–8, 1998, incorporated herein by reference), and the transfer of the XhoI-NgoMI fragment transferred those mutations.

Construction of Full-Length HPIV3 Chimeric cDNAs Encoding the HA Protein of Measles in the HN/L Junction A HPIV3 chimeric cDNA was constructed by PCR to include a heterologous polynucleotide sequence, exemplified by the measles virus HA gene, encoding a heterologous antigenic determinant of the measles virus, flanked by the transcription signals and the noncoding regions of the HPIV3 HN gene. This cDNA was designed to be combined with an rPIV3 vector as an extra gene following the HN gene. First, using Kunkel mutagenesis (Kunkel et al., *Methods Enzymol.* 154:367–382, 1987, incorporated herein by reference), a StuI site was introduced in the 3'-noncoding region of the HN gene by mutating the AGACAA (SEQ ID NO: 12) sequence at nts 8598–8603 of the antigenome to AGGCCT (SEQ ID NO: 13) yielding plasmid p3/7(131)2G-Stu (FIG. 1B). A cDNA containing the measles HA ORF flanked by HPIV3 sequences (see FIG. 1B) was then constructed in three pieces by PCR. The first PCR synthesized the left-hand, upstream piece of the gene. The forward primer 5'-GACAATAGGCCT AAAAGGGAAATATAAAAAACTTAGGAGTAAAGTT-ACGCAATCC-3' (SEQ ID NO: 14) contains a StuI site (italicized) followed by HPIV3 sequence (underlined) which includes the downstream end of the HN gene (HPIV3 nts 8602–8620), an intergenic region, and the gene-start signal and sequence from the upstream end of the HN gene (HPIV3 nt 6733–6753). The reverse primer 5'-GTAGAACGCGTT-TATCCGGTCTCGTTGTGGTGACAT CTCGAATTTGGATTTGTCTATTGGGTCCTTCC-3' (SEQ ID NO: 15) contains an MluI site (italicized) downstream of the start of the measles HA ORF (bolded) followed by the complement to HPIV3 nts 6744–6805 (underlined), which are part of the upstream HN noncoding region. The MluI site present in the introduced measles virus ORF was created by changing nt 27 from T (in the wild type Edmonston HA gene) to C and nt 30 from C to G. Both of these changes are noncoding in the measles virus ORF. The PCR was performed using p3/7(131)2G-Stu as template. The resulting product, termed PCR fragment 1, is flanked by a StuI site at the 5'-end and an MluI site at the 3'-end and contains the first 36 nt of the measles HA ORF downstream of noncoding sequence from the HPIV3 HN gene. The second PCR reaction synthesized the right-hand end of the HN gene. The forward primer 5'-CAGTCACCCGGGAA-GATGGAACCAATCGCAGATAG TCATAATTAACCATAATATGCATCAATCTATCTATAA-TACAA-3' (SEQ ID NO: 16) contains the XmaI (italics) and the end of the measles HA ORF (bold), followed by HPIV3 nts 8525–8566 (underlined) representing part of the downstream nontranslated region of the HN gene. The reverse primer 5'-CCATGTAATTGAATCCCCCAACACTAGC-3' (SEQ ID NO: 17), spans HPIV3 nts 11448–11475, located in the L gene. The template for the PCR was p3/7(131)2G-Stu. PCR fragment 2 which resulted from this reaction contains the last 35 nt of the measles HA ORF and approximately 2800 nt of the L ORF of PIV3 and is flanked by an XmaI site and an SphI site (which occurs naturally at HPIV3 position 11317). The third PCR reaction amplified the largest, central portion of the measles HA ORF from the template cDNA p™-7, a plasmid which contains the HA ORF of the Edmonston strain of measles virus supplied by the ATCC. Sequence analysis of this plasmid showed that the measles virus HA ORF contained in PTM-7 contains 2 amino acid differences from p™-7 ob the Edmonston wild type HA sequence used for insertion into the N-P and M-P junction, and these were at amino acid positions 46 (F to S) and at position 481 (Y to N). The forward primer 5'-CG-GATAAACGCGTTCTACAAAGATAACC-3' (SEQ ID NO: 18) (MluI site italicized) and reverse primer 5'-CCATCTTCCCGGGTGACTGTGCAGC-3' (SEQ ID NO: 19)(XmaI site italicized) amplified PCR fragment 3 which contained nts 19–1838 of the measles HA ORF. To assemble the pieces, PCR fragment 1 was digested with StuI and MluI while PCR fragment 3 was digested with MluI and XmaI. These two digested fragments were then cloned by triple ligation into the StuI-XmaI window of pUC118 which had been modified to include a StuI site in its multiple cloning region. The resultant plasmid, pUC118(HA 1+3) was digested with StuI and XmaI while PCR fragment 2 was digested with XmaI and SphI. The two digested products were then cloned into the StuI-SphI window of p3/7(131) 2G-Stu, resulting in the plasmid pFLC(HA HN-L). The StuI-SphI fragment, including the entire measles HA ORF, was then sequenced using dRhodamine Terminator Cycle Sequencing Ready Reaction (ABI prism, PE Applied Biosystems, Foster city, CA). The chimeric construct sequence was confirmed. In this way, the measles virus HA ORF flanked by HPIV3 transcription signals was inserted as an extra gene into the N/P, P/M, or HN/L junction of an antigenomic cDNA vector comprising a wild type HPIV3 or into the N/P or P/M junction of an antigenomic cDNA vector comprising an attenuated HPIV3.

Recovery of Chimeric rPIV3 Wild Type and rcp45L Expressing the HA Protein of Measles Virus The five full-length vector cDNAs bearing the measles HA ORF as a separate gene were transfected separately into HEp-2 cells on six-well plates (Costar, Cambridge, Mass.) together with the support plasmids {pTM(N), pTM(P no C), and pTM(L)}, and LipofectACE (Life Technologies), and the cells were simultaneously infected with MVA-T7, a replication-defective vaccinia virus recombinant encoding the bacteriophage T7 polymerase protein as previously described (Durbin et al., *Virology* 235:323–332, 1997; Durbin et al., *Virology* 234:74–83, 1997, each incorporated herein by reference). pTM(P no C) is a derivative of pTM(P) (Durbin et al., *Virology* 261:319–330, 1999) in which the C ORF expression has been silenced by mutation of the C start codon. After incubation at 32° C. for three days, the transfection harvest was passaged onto a fresh monolayer of Vero cells in a T25 flask and incubated for 5 days at 32° C. (referred to as passage 1). The presence of HPIV3 in the passage 1 harvest was determined by plaque titration on LLC-MK2 monolayer cultures with plaques visualized by immunoperoxidase staining with HPIV3 HN-specific and measles HA-specific monoclonal antibodies as previously described (Durbin et al., *Virology* 235:323–332, 1997, incorporated herein by reference).

The rPIV3(HA HN-L) virus present in the supernatant of the appropriate passage 1 harvest was biologically-cloned by plaque purification three times on LLC-MK2 cells as previously described (Hall et al., *Virus Res.* 22:173–184, 1992, incorporated herein by reference). rPIV3(HA N-P), rcp45L (HA N-P), rPIV3(HA P-M), and rcp45L(HA P-M) were biologically-cloned from their respective passage 1 harvests by terminal dilution using serial 2-fold dilutions on 96-well plates (12 wells per dilution) of Vero cell monolayers. The biologically-cloned recombinant viruses from the third round of plaque purification or from the second or third round of terminal dilution were then amplified twice in LLC-MK2 cells {rPIV3(HA HN-L} or Vero cells {rPIV3

(HA N-P), rcp45L(HA N-P), rPIV3(HA P-M), rcp45L(HA P-M)} at 32° C. to produce virus for further characterization. As a first step in confirming and characterizing the recombinant chimeric PIV3s expressing the HA glycoprotein of measles virus, each passage 1 harvest was analyzed by RT-PCR using three different primer pairs; one pair for each location of the HA ORF insert. The first primer pair amplified a fragment of PIV3 spanning nucleotides 1596–1968 of the full-length HPIV3 genome, which includes the N/P insertion site. This fragment size increased to 2298 nucleotides with the measles HA ORF inserted between the N and P genes. The second primer pair amplified a fragment of PIV3 spanning nucleotides 3438–3866 of the full-length HPIV3 genome, which includes the P/M insertion site. With the measles HA ORF inserted between the P and M genes, this fragment size increased to 2352 nucleotides. The third primer pair amplified a fragment of PIV3 spanning nucleotides 8466–8649 of the full-length antigenome. With the measles HA ORF inserted between the HN and L genes, this fragment size increased to 2211 nucleotides, which includes the HN/L insertion site. All five recovered viruses contained an insert of the appropriate size at the appropriate location. The generation of each PCR product was dependent upon the inclusion of reverse transcriptase, indicating that each was derived from RNA and not from contaminating cDNA.

Monolayers of LLC-MK2 cells in T25 flasks were infected at a multiplicity of infection (MOI) of 5 with either rcp45L(HA N-P), rcp45L(HA P-M), rJS or were mock infected. Monolayers of Vero cells in T25 flasks were infected with the Edmonston wild type strain of measles virus at an MOI of 5, Vero cell monolayers were chosen for the measles Edmonston virus infection because measles virus does not grow well in LLC-MK2 cells. At 24 hours post-infection, the monolayer was washed with methionine-minus DMEM (Life Technologies). $^{35}S$ methionine was added to DMEM-minus media at a concentration of 10 uCi/ml and 1 ml was added to each flask which was then incubated at 32° C. for 6 hours. The cells were harvested and washed 3 times in PBS. The cell pellets were resuspended in 1 ml RIPA buffer {1% (w/v) sodium deoxycholate, 1% (v/v) Triton X-100 (Sigma), 0.2% (w/v) SDS, 150 mM NaCl, 50 mM Tris-HCl, pH 7.4}, freeze-thawed and clarified by centrifugation at 6500 × G for 5 minutes. The cell extract was transferred to a fresh eppendorf tube and a mixture of monoclonal antibodies which recognizes the HA glycoprotein of measles virus (79-XV-V17, 80-III-B2, 81-1-366) (Hummel et al., J. Virol. 69:1913–6, 1995; Sheshberadaran et al., Arch. Virol. 83:251–68, 1985, each incorporated herein by reference) or which recognizes the HN protein (101/1, 403/7, 166/11) of PIV3 (van Wyke Coelingh et al., Virology 160:465–72, 1987, incorporated herein by reference) was added to each sample and incubated with constant mixing for 2 hours at 4° C. Immune complexes were precipitated by adding 200 μl of a 10% suspension of protein A Sepharose beads (Sigma, St. Louis, Mo.) to each sample followed by constant mixing at 4° C. overnight Each sample was suspended in 90 μl of IX loading buffer and 10 μl of reducing agent was added. After heating at 70° C. for 10 minutes, 20 μl of each sample was loaded onto a 4–12% polyacrylamide gel (NuPAGE, Novex, San Diego, Calif.) per the manufacturer's recommendations. The gel was dried and autoradiographed (FIG. 2). rcp45L(HA P-M) and rcp45L(HA N-P) encoded a protein precipitated by the anti-measles HA monoclonal antibodies which was the same size as the authentic measles HA protein. rcp45L(HA P-M) and rcp45L(HA N-P) expressed the measles virus HA protein to a greater extent than did the Edmonston wild type strain of measles virus indicating that these constructs efficiently expressed the measles virus HA from the N/P and P/M junctions of the attenuated strain rcp45L. rcp45L(HA N-P) and rcp45L(HA P-M) were confirmed to be HPIV3-based by their reactivity with the PIV3 anti-HN monoclonal antibodies.

The Temperature Sensitivity of Replication of rPIV3 Parent and rPIV3(HA) Chimeric Viruses In Vitro The level of temperature sensitivity of replication of the chimeric rPIV3s bearing the measles virus HA insertion was evaluated to assess whether acquisition of the HA insert modified the level of replication in the chimeric virus compared to the parental, vector virus at various temperatures (Table 1). Serial 10-fold dilutions of rcp45L, rcp45L (N-P), rcp45L(HA P-M), rPIV3(HA HN-L), rPIV3(HA P-M), or rJS were carried out in L-15 supplemented with 5% FBS, 4 mM glutamine, and 50 μg/ml gentamicin on LLC-MK2 cell monolayers in 96 well plates and incubated at 32, 36, 37, 38, 39, or 40° C. for 6 days. Virus was detected by hemadsorption and reported as $\log_{10}$ TCID$_{50}$/ml. Interestingly, chimeric derivatives of both wild type vector viruses bearing the measles virus HA gene, rPIV3(HA HN-L) and rPIV3(HA P-M), were slightly restricted in replication at 40° C. (Table 1). The two attenuated rPIV3s bearing the measles virus HA gene, rcp45L(N-P) and rcp45L(HA P-M), possessed a level of temperature sensitivity similar to that of the rcp45L parental, vector virus with rcp45L(HA P-M) being slightly more ts than its parent. Thus, the viruses bearing the inserts replicated in tissue culture similarly to the parental vector rPIV3 from which they were derived, with only a slight increase in temperature sensitivity. These results indicate that rPIV3 can readily serve as a vector to accommodate the HA insert at different sites without major alteration in replication in vitro, and that rPIV3(HA) chimeric viruses can readily accommodate the further addition of one or more attenuating mutations.

TABLE 1

Replication at permissive and elevated temperatures of recombinant HPIV3s expressing the HA protein of measles virus as an extra gene in the N-P, P-M, or HN-L junctions.

| | Virus titer ($\log_{10}$TCID$_{50}$/ml) at indicated temperature | | | | | |
|---|---|---|---|---|---|---|
| Virus | 32° C[1]. | 36° C. | 37° C. | 38° C. | 39° C. | 40° C. |
| rcp45L[2] | 8.2 | 8.2 | 7.2 | <u>5.2</u>[6] | 3.4 | 3.0 |
| rcp45L (HA P-M)[3] | 7.4 | 6.7 | <u>5.2</u> | 4.2 | 1.4 | 1.4 |
| rcp45L (HA N-P)[3] | 7.4 | 7.2 | 5.7 | <u>4.2</u> | 2.2 | ≦1.2 |
| rPIV3 (HA HN-L)[4] | 7.7 | 8.2 | 7.0 | 7.7 | 6.7 | <u>5.2</u> |
| rPIV3 (HA P-M)[4] | 7.7 | 7.4 | 6.7 | 6.2 | 6.2 | <u>4.7</u> |
| PIV3-rJS[5] | 8.7 | 9.0 | 9.0 | 8.4 | 8.2 | 9.0 |

[1]Permissive temperature.
[2]Recombinant ts derivative of the JS wild type strain of HPIV3, bearing 3 attenuating amino acid substitutions derived from cp45.
[3]Recombinant attenuated ts derivative of JS wild type HPIV3 expressing the HA protein of measles virus.
[4]Recombinant wild type HPIV3 expressing the HA protein of measles virus.
[5]Recombinant wild type HPIV3, strain JS.
[6]Underlined titer represents the lowest restrictive temperature at which a 100-fold or greater reduction in titer from that at 32° C. is seen and defines the shut-off temperature of the virus.

EXAMPLE II

Chimeric rPIV3s Bearing an Antigenic Determinant of Measles Virus Replicate Efficiently in Hamsters and Induce High Titers of Antibodies Against Both HPIV3 and Measles Determination of the Level of Replication and Immunogenicity of the rPIV3(Ha) Viruses in Hamsters The levels of replication of chimeric rPIV3s bearing an antigenic determinant of the measles virus was compared with that of their parent rPIV3s to determine if the acquisition of the determinant, exemplified by an HA insert, significantly modified their ability to replicate and to induce an immune response in vivo. In two different experiments, groups of 6 or 7 4–6 week-old Golden Syrian hamsters were inoculated intranasally with 0.1 ml of EMEM (Life Technologies) containing $10^{6.0}$ PFU of rJS, rcp45L, rcp45L(HA P-M), rcp45L(HA N-P), rPIV3(HA HN-L), or rPIV3(HA P-M) (Tables 2 and 3). On day 4 post-inoculation the hamsters were sacrificed and the lungs and nasal turbinates were harvested. The nasal turbinates and lungs were homogenized in 10% or 20% w/v suspension of L-15 (Quality Biologicals, Gaithersburg, Md.) respectively, and the samples were rapidly frozen. Virus present in the samples was titered on 96 well plates of LLC-MK2 cell monolayers and incubated at 32° C. for 7 days. Virus was detected by hemadsorption, and the mean $\log_{10} TCID_{50}/g$ was calculated for each group of hamsters. Insertion of the HA gene into wild type rJS (Table 2) restricted its replication 4 to 20-fold in the upper respiratory tract and up to five-fold in the lower respiratory tract indicating only a slight effect of the acquisition of the HA gene on replication of wild type rJS virus in hamsters. The replication of each of the two rcp45(HA) antigenic chimeras was 10-fold less in the upper respiratory tract of hamsters (Table 3)-than that of rcp45L, the recombinant parent virus bearing the three attenuating ts mutations in the L protein, but was the same as the rcp45L parent in the lower respiratory tract. Thus, for each of the two rcp45(HA) antigenic chimeras there was a slight, but statistically significant, reduction in replication in the upper respiratory tract of hamsters indicating that the acquisition of the HA gene by rcp45L increased its attenuation for the upper, but not the lower, respiratory tract. Thus, the effect of the insertion of the HA gene on the replication of wild type or attenuated PIV3 was comparable in the upper respiratory tract.

TABLE 2

Replication of wildtype rPIV3(HA) chimeric viruses in the upper and lower respiratory tract of hamsters

| Virus[1] | # Animals | Virus Titer ($\log_{10} TCID_{50}$/gm ± S.E.[2]) [Tukey-Kramer Grouping][3] | |
|---|---|---|---|
| | | Nasal Turbinates | Lungs |
| rcp45L | 8 | 4.0 ± 0.1 [A] | 1.5 ± 0.1 [A] |
| rPIV3(HA N-P) | 8 | 5.1 ± 0.1 [B] | 5.9 ± 0.1 [B] |
| rPIV3(HA P-M) | 8 | 5.9 ± 0.1 [C] | 6.7 ± 0.2 [C] |
| rPIV3(HA HN-L) | 8 | 5.9 ± 0.2 [C] | 5.8 ± 0.1 [B] |
| rJS | 8 | 6.5 ± 0.1 [D] | 6.6 ± 0.2 [C] |

[1]Animals received $10^6 TCID^{50}$ of the indicated virus given intranasally in a 0.1 ml inoculum and the lungs and nasal turbinates were harvested 4 days later.
[2]Standard Error.
[3]Mean virus titers were assigned to statistically similar groups (A-D) by the Tukey-Kramer test. Therefore, means in each column with different letters are significantly different ($\alpha = 0.05$) and those with the same letter are not significantly different.

TABLE 3

Replication of the rPIV3cp45L(HA) antigenic chimeric viruses in the upper and lower respiratory tract of hamsters

| Virus[1] | # Animals | Virus Titer ($\log_{10} TCID_{50}$/gm ± S.E.[2]) [Tukey-Kramer Grouping][3] | |
|---|---|---|---|
| | | Nasal Turbinates | Lungs |
| rcp45L | 6 | 4.7 ± 0.2 [A] | 2.9 ± 0.1 [A] |
| rcp45L(HA N-P) | 6 | 3.7 ± 0.2 [B] | 2.9 ± 0.1 [A] |
| rcp45L(HA P-M) | 7 | 3.7 ± 0.1 [C] | 2.9 ± 0.2 [A] |
| rJS | 7 | 6.5 ± 0.1 [D] | 5.6 ± 0.2 [B] |

[1]Animals received $10^6$ pfu of the indicated virus given intranasally in a 0.1 ml inoculum and the lungs and nasal turbinates were harvested 4 days later.
[2]Standard Error.
[3]Mean virus titers were assigned to statistically similar groups (A-D) by the Tukey-Kramer test. Therefore, means in each column with different letters are significantly different ($\alpha = 0.05$) and those with the same letter are not significantly different.

The ability of the chimeric rHPIV3 (HA) viruses to induce an immune response to HPIV3 and to measles virus was studied next. Groups of 6–24 Golden Syrian hamsters (age 4–6 weeks) were infected as described above with either $10^{6.0}$ PFU rJS, rPIV3(HA P-M), rcp45L, rcp45L(HA P-M), or rcp45L(HA N-P) (Table 4) on day 0. Serum was collected from each hamster on day −1 and on day 25 post-inoculation. The serum antibody response to HPIV3 was evaluated by hemagglutination-inhibition (HAI) assay as previously described (van Wyke Coelingh et al., *Virology* 143:569–582, 1985, incorporated herein by reference), and the serum antibody response to measles virus was evaluated by 60% plaque-reduction assay as previously described (Coates et al., *Am. J. Epidemiol.* 83:299–313, 1966, incorporated herein by reference). These results were compared with that from an additional control group of cotton rats that received $10^{5.0}$ of the live-attenuated measles virus (Moraten strain) administered intramuscularly on day 0. Cotton rats, rather than hamsters, were used in this group because measles virus is only weakly infectious for hamsters. As can be seen in Table 4, each of the PIV3(HA) chimeric viruses was able to elicit a robust serum neutralizing antibody response against measles virus. There was no significant difference between the amount of serum neutralizing antibody elicited by the attenuated derivative rcp45L(HA P-M) as compared to its counterpart in the wild type background, rPIV3 (HA P-M). Furthermore, the level of measles virus-neutralizing serum antibodies induced by the rPIV3(HA) recombinants were on average 5-fold greater than that achieved by the intramuscular immunization with the live attenuated measles virus vaccine. In addition, the serum antibody response to HPIV3 produced by all the chimeric viruses was also robust and comparable to that produced by infection with wild type rJS.

TABLE 4 rPIV3(HA) antigenic chimeric viruses elicit an excellent serum antibody response to both measles virus and PIV3

| Virus[1] | # Animals | Serum antibody titer to measles virus (60% plaque reduction neutralization titer, mean reciprocal log$_2$ ± S.E.[2]) | | Serum antibody response to HPIV3 (HAI titer; mean reciprocal log$_2$ ± S.E.) | |
|---|---|---|---|---|---|
| | | Day 0 | Day 25 | Day 0 | Day 25 |
| rcp45L[3] | 18 | ≦3.3 ± 0 | ≦3.3 ± 0 | ≦2.0 ± 0 | 10.7 ± 0.2 |
| rcp45L (HA P-M)[4] | 24 | ≦3.3 ± 0 | 12.8 ± 0.1 | ≦2.0 ± 0 | 9.2 ± 0.2 |
| rcp45L (HA N-P)[5] | 6 | ≦3.3 ± 0 | 13.4 ± 0.4 | ≦2.0 ± 0 | 10.8 ± 0.3 |
| rPIV3 (HA P-M)[6] | 6 | ≦3.3 ± 0 | 13.3 ± 0.3 | ≦2.0 ± 0 | 10.3 ± 0.2 |
| Measles virus (Moraten)[7] | 4 | ≦3.3 ± 0 | 10.8 ± 0.2 | ≦2.0 ± 0 | ≦2.0 ± 0 |
| rJS[8] | 6 | ≦3.3 ± 0 | ≦3.3 ± 0 | ≦2.0 ± 0 | 10.7 ± 0.2 |

[1]Virus was administered at a dose of 10$^{6.0}$ PFU in a 0.1 ml inoculum intranasally on day 0 to all animals with the exception of those in the measles virus group which received virus by intramuscular injection.
[2]Standard Error.
[3]Recombinant attenuated HPIV3 with three temperature sensitive (ts) mutations in the L protein, derived from cp45.
[4]Recombinant attenuated HPIV3 in the cp45L background with the HA ORF of measles virus in the P/M noncoding region of rPIV3.
[5]Recombinant attenuated HPIV3 in the cp45L background with the HA ORF of measles virus in the N/P noncoding region of rPIV3.
[6]Recombinant HPIV3 with the HA ORF of measles virus in the P/M noncoding region of wild type rPIV3.
[7]The live attenuated measles vaccine virus, Moraten strain, was administered at a dose of 10$^5$ pfu in a 0.1 inoculum by IM injection to 4 cotton rats in a separate study. All other animals were hamsters.
[8]Recombinant wildtype HPIV3.

Six hamsters from each group and from a control group similarly infected with RSV were challenged on day 25 with 10$^{6.0}$ pfu of biologically-derived HPIV3 wildtype virus given intranasally in a 0.1 ml inoculum. The lungs and nasal turbinates were harvested on day 4 and processed as described above. Virus present in the samples was titered on 96 well plates of LLC-MK2 cell monolayers and incubated at 32° C. for 7 days. Virus was detected by hemadsorption and the mean log$_{10}$ TCID$_{50}$/g was calculated for each group of hamsters. As shown in Table 5, those hamsters which had received the chimeric viruses, whether in the attenuated or wild type backbone, were highly protected against replication of challenge wild type HPIV3 in both the upper and the lower respiratory tract. Thus, despite the slight attenuating effect of the acquisition of the measles virus HA gene on replication of the rcp45(HA) chimeric viruses, infection with either rcp45L(HA P-M) or rcp45L(HA N-P) induced a high level of protection against HPIV3 as indicated by approximately a 1000-fold reduction of its replication in the upper and lower respiratory tract of hamsters. Since wild type measles virus does not replicate efficiently in hamsters, it cannot be used to challenge this host. However, it is expected that the attenuated chimeric rcp45L(HA) vaccine candidates will be highly efficacious against measles virus since high levels of neutralizing antibody, ie., mean titer of greater than 1:5000, were induced. Comparable levels of measles virus antibodies are associated with strong resistance to measles virus disease in humans (Chen et al., *J. Infect. Dis.* 162:1036–42, 1990, incorporated herein by reference).

TABLE 5

Attenuated and wildtype HPIV3-measles HA chimeric viruses are highly protective against replication of challenge wildtype PIV3 in the upper and lower respiratory tracts of hamsters.

| Animals Immunized with[1] | # Animals | Virus titer (log$_{10}$TCID$_{50}$/g) [Tukey-Kramer Grouping[3]] | | Reduction in Titer (log$_{10}$) | |
|---|---|---|---|---|---|
| | | Nasal Turbinates | Lungs | Nasal Turbinates | Lungs |
| RSV | 6 | 7.0 ± 0.3 [A] | 5.7 ± 0.4 [A] | NA[2] | NA |
| rcp45L (HA P-M) | 6 | 3.4 ± 0.3 [B] | 2.9 ± 0.0 [B] | 3.6 | 2.8 |
| rcp45L (HA N-P) | 6 | 2.6 ± 0.3 [B] | 3.4 ± 0.2 [B] | 4.4 | 2.3 |
| rPIV3 (HA P-M) | 6 | 2.0 ± 0.3 [B] | 3.2 ± 0.1 [B] | 5.0 | 2.5 |
| rcp45L | 6 | 1.9 ± 0.2 [B,C] | 3.6 ± 0.1 [B] | 5.1 | 2.1 |
| rJS | 6 | <1.4 ± 0.0 [C] | 2.9 ± 0.2 [B] | >5.7 | 2.8 |

[1]All groups were challenged with 10$^6$ pfu biologically-derived JS wildtype PIV3 in a 0.1 ml inoculum given intranasally.
[2]Not applicable.
[3]Mean virus titers were assigned to statistically similar groups (A-C) by the Tukey-Kramer test. Therefore, means in each column with different letters are significantly different (α = 0.05) and means with the same letter are not significantly different.

EXAMPLE III

Figure 3:
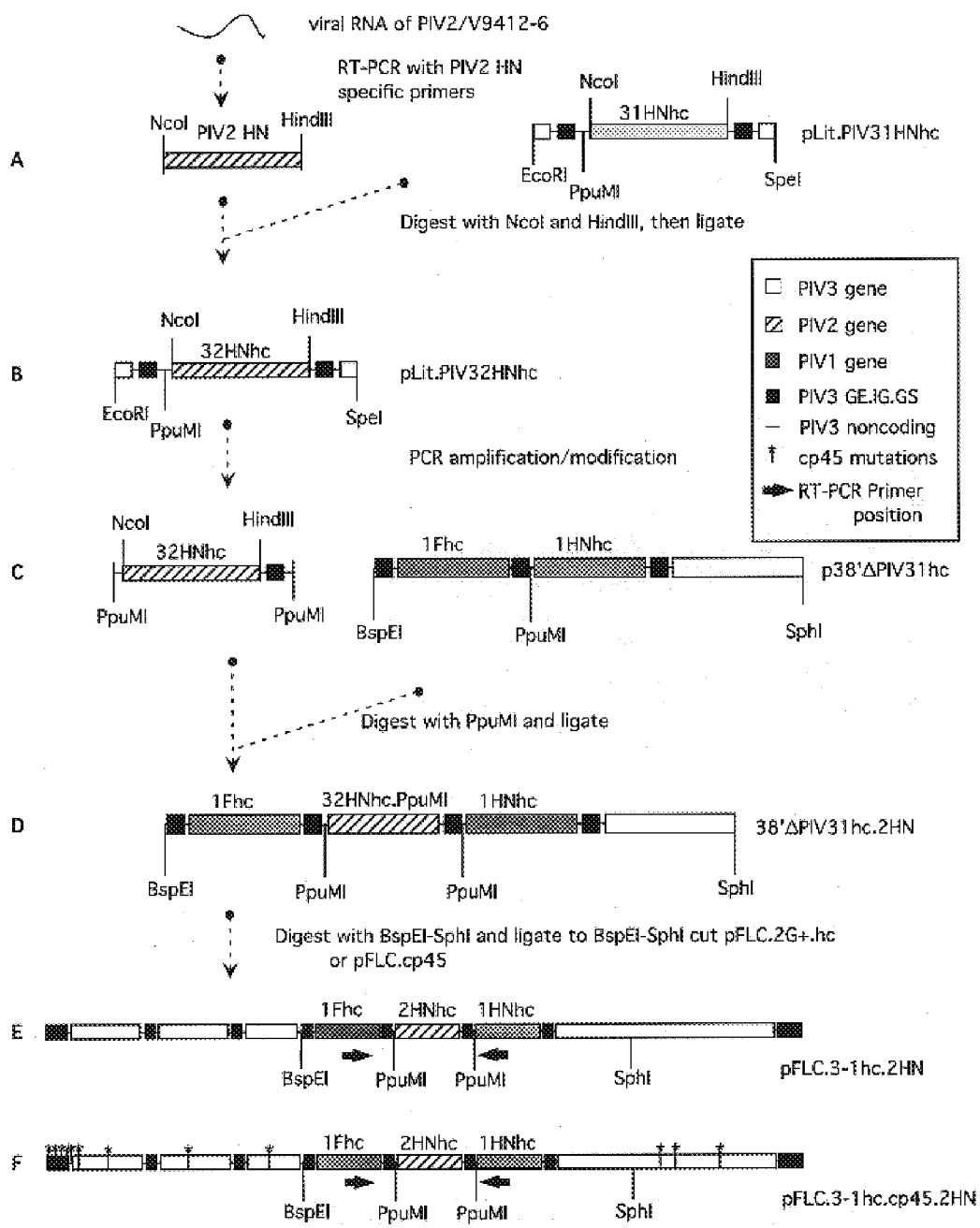
FIG. 3 illustrates insertion of the HPIV2 HN gene as an extra transcription/translation unit into the antigenomic cDNA encoding rPIV3-1 or rPIV3-1cp45 chimeric virus (Note: rPIV3-1 is a rPIV3 in which the HN and F genes were replaced by those of HPIV1, and rPIV3-1cp45 is a version which cont multiple cloning site, so that the total length of the insert would conform to the rule of six.
Figure 4:
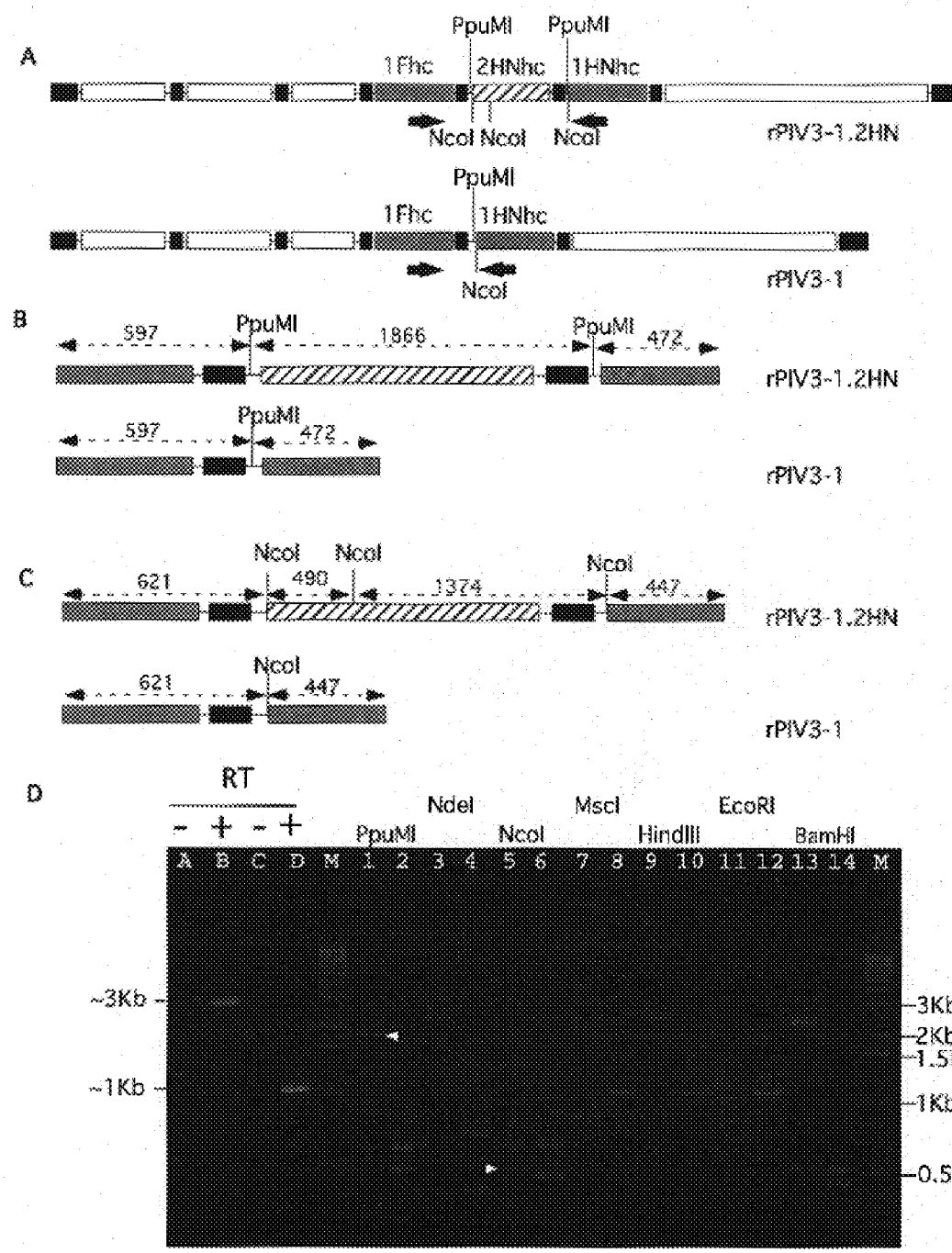
Figure 5:
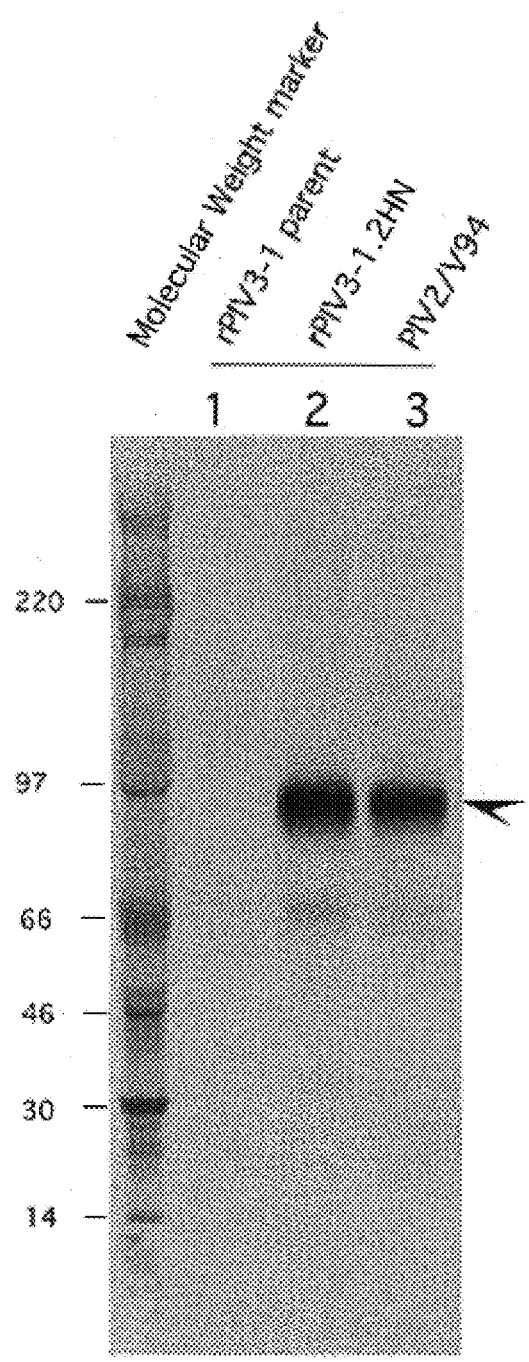

Construction of Antigenomic cDNAs Encoding a Chimeric HPIV3-1 Vector Bearing a HPIV2 HN Gene as an Extra Transcription/Translation Unit Inserted Between the F and HN Genes and Recovery of Infectious Viruses rPIV3-1 is a recombinant chimeric HPIV3 in which the HN and F genes have been replaced by those of HPIV1 (see, e.g., Skiadopoulos et al., *Vaccine* 18:503–510, 1999; Tao et al., *Vaccine* 17:1100–1108, 1999; U.S. patent application Ser. No. 09/083,793, filed May 22, 1998, each incorporated herein by reference). In the present example, the HN gene of HPIV2 was inserted into the rPIV3-1 chimeric virus that served as a vector to produce a chimeric derivative virus, bearing an introduced heterologous antigenic determinant from HPIV2, able to protect against both HPIV1 and HPIV2. The HPIV2 HN gene also was inserted into an attenuated derivative of rPIV3-1, designated rPIV3-1cp45, which contains 12 of the 15 cp45 mutations, i.e., those mutations on genes other than HN and F, inserted into the rPIV3 backbone (Skiadopoulos et al., *Vaccine* 18:503–510, 1999). The source of the HPIV2 wild type virus was the wild type strain V9412-6 (designated PIV2/V94) (Tao et al., *Vaccine* 17:1100–1108, 1999), which was isolated in Vero cells from a nasal wash that was obtained in 1994 from a child with a natural HPIV2 infection. PIV2/V94 was plaque purified 3 times on Vero cells before being amplified twice on Vero cells using OptiMEM tissue culture medium without FBS. A cDNA clone of the HN gene of PIV2/V94 was generated from virion RNA by reverse transcription (RT) using random hexamers and Superscript Preamplification System (Life Technologies) followed by PCR using Advantage cDNA Synthesis kit (Clontech, Palo Alto, Calif.) and synthetic primers which introduced NcoI-HindIII sites flanking the HN cDNA (FIG. 3A). The sequences of these primers were: (with HPIV specific sequences in upper case, restriction sites underlined, nts which are non-HPIV or which are altered from wt in lower case, and start and stop codons in bold), upstream HPIV2 HN 5'-ggg ccATGGAAGATTACAGCAAT-3' (SEQ ID NO: 20); downstream HPIV2 HN 5'-caataagcTTAAAGCATTAGTTCCC-3' (SEQ ID NO: 21). The HN PCR fragment was digested with NcoI-HindIII and cloned into pLit.PIV31HNhc to generate pLit.32HNhc (FIG. 3 B). The HPIV2 HN heterologous gene insert in pLit.32HNhc was completely sequenced using the ThermoSequenase Kit and $^{33}$P-labeled terminators (Pharmacia Amersham, Piscataway, N.J.) and was confirmed to contain the authentic sequence of the PIV2/94 HN coding region.

The HPIV2 HN gene in pLit.32HNhc was further modified by PCR and Deep Vent thermostable DNA polymerase (New England Biolab, Beverly, Mass.) to introduce PpuMI sites for cloning into the unique PpuMI site in p38'ΔPIV31hc, FIG. 3C (Skiadopoulos et al., *Vaccine* 18:503–510, 1999). The sequences of these primers were (with HPIV specific sequences in upper case, relevant restriction sites underlined, non-HPIV nt or nt altered from wt in lower case): upstream HPIV2 HN 5'-gcgatgggcccGAGGAAGGACCCAATAGACA-3' (SEQ ID NO: 22); downstream HPIV2

5'-cccgggtcctgATTTCCCGAGCACGCTTTG-3' (SEQ ID NO. 23). The modified cDNA bearing the HPIV2 HN ORF consists of (from left to right) a partial 5'-untranslated region (5'-UTR) of HPIV3 HN including the PpuMI site at the 5'-end, the HPIV2 HN ORF, the 3'-UTR of HPIV3 HN, a complete set of HPIV3 transcription signals (i.e. gene stop, intergenic region and gene start sequences) whose sequences match those at the HPIV3 HN and L gene junction, a partial 5'-UTR of HPIV3 L, and an added PpuMI site at its 3'-end (FIG. 3C). This fragment was digested with PpuMI and inserted into p38'ΔPIV31hc digested with PpuMI to generate p38'ΔPIV31hc.2HN (FIG. 3D). The inserted PpuMI cassette was sequenced in full and found to be as designed. The insert from p38'ΔPIV31hc.2HN was isolated as a 8.5% b BspEI-SphI fragment and introduced into the BspEI-SphI window of pFLC.2G+.hc or pFLCcp45 to generate pFLC.31hc.2HN or pFLC.31hc.cp45.2HN, respectively (FIG. 3, E and F). pFLC.2G+.hc and pFLCcp45 are full-length antigenomic clones encoding wt rPIV3-1 and rPIV3cp45, respectively, as described previously (Skiadopoulos et al., *J. Virol.* 73:1374–81, 1999; Tao et al., *J. Virol.* 72:2955–2961, 1998, each incorporated herein by reference).

Confluent HEp-2 cells were transfected with pFLC.31hc.2HN or pFLC.3-1hc.cp45.2HN plus the pTM (N), pTM(P no C), and pTM(L) support plasmids in the presence of MVA-T7 as previously described (Durbin et al., *Virology* 235:323–332, 1997, incorporated herein by reference). The recombinant chimeric viruses recovered from transfection were activated by addition of TPCK trypsin (Catalog No. 3741, Worthington Biochemical Corp., Freehold, N.J.) as were all passages and titrations of viruses bearing the HPIV1 HN and F glycoproteins as described previously (Tao et al., *J. Virol.* 72:2955–2961, 1998, incorporated herein by reference). Recovered chimeric recombinant viruses rPIV3-1.2HN and rPIV3-1cp45.2HN were purified by plaque-to-plaque-to-plaque passage on LLC-MK2 monolayer in agarose overlay as previously described (Tao et al., *Vaccine* 17:1100–1108, 1999, incorporated herein by reference).

To determine if the rPIV3-1.2HN and rPIV3-1cp45.2HN recombinants contain the heterologous HPIV2 HN gene, viral RNA from each recovered recombinant chimeric virus was amplified on LLC-MK2 cells and concentrated by polyethylene glycol (PEG) precipitation (Mbiguino et al., *J. Virol. Methods* 31:161–170, 1991, incorporated herein by reference). Virion RNA (vRNA) was extracted with Trizol (Life Technologies) and used as template to synthesize first strand cDNA using Superscript Preamplification system (Life Technologies, Gaithersburg, Md.) and random hexamer primers as described above. The synthesized cDNA was amplified by PCR with the Advantage cDNA Synthesis kit (Clontech, Palo Alto, Calif.) with primers specific for HPIV1 F and HPIV1 HN coding region (for HPIV1 F 5'-AGTGGCTAATTGCATTGCATCCACAT-3' (SEQ ID NO: 24) and for HPIV1 HN 5'-GCCGTCTGCATGGTGAATAGCAAT-3') (SEQ ID NO: 25). The relative locations of the PIV1 F and HN primers are indicated by arrows in FIGS. 3 and 4. Amplified DNA fragments were digested and analyzed on agarose gels (FIG. 4). Data for rPIV3-1cp45.2HN is not shown, but was comparable and confirmed in structure. rPIV3-1.2HN and rPIV3-1cp45.2HN each contained the insert of the expected size, and the digestion patterns with a number of restriction enzymes confirmed the identity and authenticity of the inserts. The presence of the cp45 mutations in rPIV3-1cp45.2HN was also confirmed.

To confirm the expression of HPIV2 HN by the rPIV3-1.2HN chimeric virus, LLC-MK2 monolayers in T25 flasks were infected with PIV2/V94, rPIV3-1, or rPIV3-1.2HN at a MOI of 5 in 5 ml of serum-free OptiMEM containing 0.5 μg/ml TPCK trypsin. After incubation for 18 hours at 32° C., the flasks were washed three times with 5 ml of methionine and cysteine deficient DMEM (BioWhittacker, Walkersville, Md.). Cells were then fed with 1 ml of methionine and cysteine deficient DMEM supplemented with 120 μCi of ProMix $^{35}$S-methionine and $^{35}$S-cysteine mixture (Pharmacia Amersham, Piscataway, N.J.) and incubated for 18 hours at 32° C. Cells were scraped into medium, pelleted by brief centrifugation in a microfuge, and washed three times with cold PBS. Each cell pellet was resuspended in 1 ml RIPA buffer (1% sodium deoxycholate, 1% Triton X-100, 0.2% SDS, 150 mM NaCl, and 50 mM Tris-HCl, pH7.4) containing 250 units/ml of Benzonase (Sigma), freeze/thawed once, and clarified by centrifugation at 12,000×g for 5 min in a microfuge. Clarified supernatants were transferred to a clean microfuge tube, mixed with 50 μl of anti-HPIV2 HN monoclonal antibody (mAb) 150S1 (Tsurudome et al., *Virology* 171:38–48, 1989, incorporated herein by reference), and incubated with mixing at 4° C. for 3 hours. The monoclonal antibody was precipitated by the addition to each tube of 0.2 ml of 10% Protein A sepharose suspension (in RIPA buffer) and incubation with mixing at 4° for 18 hours. The beads were washed three times with RIPA buffer and pelleted by brief centrifugation in a microfuge. Each sample was suspended in 90 μl of 1× loading buffer, and 10 μl was resolved on a 4–12% SDS polyacrylamide gel (PAGE; NOVEX, San Diego, Calif.). The gel was dried and autoradiographed (FIG. 5). The mAb, specific to PIV2 HN, precipitated a protein from both rPIV3-1.2HN and PIV2/V94 infected LLC-MK2 cells, but not from rPIV3-1-infected cells, with a size expected for the 86 kD Kd HN protein of HPIV2 (Rydbeck et al., *J. Gen. Virol.* 69:931–5, 1988, incorporated herein by reference).

EXAMPLE IV

The rPIV3-1 Viruses Carrying an HPIV2 Antigenic Determinant Exhibit Temperature Sensitive Phenotypes Similar to Those of their Parental Vector Viruses The level of temperature sensitivity of replication of rPIV3-1.2HN and rPIV3-1.cp45.2HN in LLC-MK2 cells was evaluated to determine if the acquisition of the HN ORF of HPIV2 by rPIV3-1 wild type or attenuated viruses employed as vectors altered the level of temperature sensitivity of replication in the resultant chimeric derivatives bearing the heterologous antigenic determinant of HPIV2 compared to the parental, vector viruses (Table 6). rPIV3-1.2HN and rPIV3-1cp45.2HN, along with control viruses, were serially diluted 1:10 in 1× L15 supplemented with 0.5 µg/ml TPCK trypsin and used to infect LLC-MK2 monolayers in 96 well plates in quadruplicate. Infected plates were placed at various temperatures for 7 days before the virus titers were determined by hemadsorption using 0.2% guinea pig erythrocytes (in 1×PBS). The virus titers are presented as $\log_{10}$ TCID$_{50}$±standard error (S.E.). As shown in Table 6, rPIV3-1.2HN and rPIV3-1cp45.2HN exhibited a level of temperature sensitivity similar to that of their parental, vector viruses, i.e. rPIV3-1 and rPIV3-1cp45, respectively, each of which lacks the HPIV2 HN insert. This indicated that the introduction of one extra transcription/translation unit in rPIV3-1.2HN and rPIV3-1cp45.2HN, does not significantly alter their level of temperature sensitivity of replication in vitro.

TABLE 6

The rPIV3-1 viruses carrying the PIV2 HN insertion have a temperature sensitive phenotype similar to that of their parental virus.

| Virus | Titer at 32° C.[a] ($\log_{10}$TCID$_{50}$) | Titer reduction ($\log_{10}$TCID$_{50}$) at various temperatures (° C.)[a] | | | | | |
|---|---|---|---|---|---|---|---|
| | | 35°[b] | 36° | 37° | 38° | 39° | 40° |
| PIV2/V9412 | 7.8 | 0.3 | (0.1)[c] | 0.0 | (0.4) | (0.4) | 0.0 |
| PIV1/Wash64 | 8.5 | 1.5 | 1.1 | 1.4 | 0.6 | 0.5 | 0.9 |
| rPIV3/JS | 7.9 | 0.3 | 0.1 | 0.1 | (0.3) | (0.4) | 0.4 |
| PIV3 cp45 | 7.8 | 0.5 | 0.3 | 1.3 | <u>3.4</u>[d] | 6.8 | 6.9 |
| rPIV3-1 | 8.0 | 0.8 | 0.5 | 0.6 | 0.9 | 1.1 | <u>2.6</u> |
| rPIV3-1.2HN | 8.3 | 0.5 | (0.3) | 0.3 | 0.6 | 1.5 | <u>2.6</u> |
| rPIV3-1cp45 | 8.0 | 0.5 | 0.4 | <u>3.4</u> | 4.8 | 6.6 | 7.5 |
| rPIV3-1 cp45.2HN | 8.0 | 0.3 | 1.4 | <u>2.9</u> | 5.3 | 7.6 | 7.6 |

[a]Data presented are means of two experiments.
[b]Data at 35° C. were from single experiment.
[c]Numbers in parentheses represent titer increase.
[d]Underlined value indicates shut-off temperature at which the virus titer showed a reduction of 100-fold or more in comparison to the titer at 32° C.

EXAMPLE V

Replication and Immunogenicity of rHPIV3-1.2HN Chimeric Viruses in Animals

To determine the level of replication of the chimeric viruses in vivo, Golden Syrian hamsters in groups of six were inoculated intranasally with 0.1 ml of 1× L-15 medium containing $10^{5.3}$TCID$_{50}$ (or $10^6$ pfu) of virus (Table 7). Four days after infection, hamsters were sacrificed and their lungs and nasal turbinates harvested. Virus titers, expressed as mean $\log_{10}$ TCID$_5$O/gram of tissue (Table 7), were determined. rPIV3-1 expressing the PIV2 HN gene, termed rPIV2-1.2HN, is more restricted in replication than its rPIV3-1 parent as indicated by a 30-fold reduction in virus titer in both the upper and lower respiratory tracts of hamsters. Thus, the insertion of a transcription/translation unit expressing the PIV2 HN protein into rPIV3-1 attenuates the virus for hamsters. The attenuating effect of insertion of a transcription/translation unit containing PIV2 HN ORF into rPIV3-1 was slightly more than that observed for the insertion of a similar unit containing the measles HA ORF into the recombinant JS strain of wild type PIV3. The rPIV3-1cp45.2HN virus was 1,000-fold more restricted in replication than the rPIV3-1cp45 parent indicating that the attenuating effect of the PIV2 HN insertion and the cp45 mutations are additive. It should be possible to adjust the level of attenuation as needed by adding fewer cp45 mutations than the 12 that are present in rPIV3-1.cp45.2HN.

TABLE 7

The chimeric rPIV3-1 expressing the HN glycoprotein of PIV2 (rPIV3-1.2HN) is attenuated in the respiratory tract of hamsters

| Experiment No. | Virus | Virus titer in indicated tissue $\log_{10}$TCID$_{50}$/g ± S.E.)[c] | |
|---|---|---|---|
| | | NT | Lungs |
| 1[a] | rPIV3-1 | 6.9 ± 0.1 [A][d] | 6.0 ± 0.3 [A] |
| | rPIV3-1.2HN | 5.4 ± 0.2 [B] | 4.4 ± 0.4 [C] |
| 2[b] | rPIV3-1 | 6.7 ± 0.1 [A] | 6.6 ± 0.2 [A] |
| | rPIV3-1.2HN | 5.1 ± 0.1 [B, C] | 5.2 ± 0.2 [B] |
| | rPIV3-1cp45 | 4.6 ± 0.3 [C] | 1.8 ± 0.4 [D] |
| | rPIV3-1cp45.2HN | 1.5 ± 0.1 [D] | ≦1.2 [D] |
| | rPIV3/JS | 6.5 ± 0.2 [A] | 6.7 ± 0.1 [A] |
| | rcp45 | 4.9 ± 0.2 [B, C] | 1.2 ± 0.04 [D] |

[a]Groups of six animals were inoculated intranasally with $10^6$ pfu of indicated virus in 0.1 ml medium on day 0.
[b]Groups of 6 hamsters were inoculated intranasally as in Experiment 1 with $10^{5.3}$ TCID$_{50}$ of indicated virus on day 0.
[c]Lungs and nasal turbinates of the hamsters were harvested on day 4. Virus titers in tissue were determined and the titer expressed as $\log_{10}$TCID$_{50}$/gram ± standard error (S.E.). NT = nasal turbinates.
[d]Means in each column with a different letter are significantly different (a = 0.05) by Duncan's Multiple Range test whereas those with the same letter are not significantly different.

Since the single rPIV3-1.2HN virus expresses protective antigens of PIV1 (the F and HN glycoprotein) and PIV2 (the HN glycoprotein only), infection with this virus will induce resistance against challenge with either PIV1 or PIV2 wild type viruses. To verify this, Golden Syrian hamsters in groups of 12 were immunized intranasally with $10^{5.3}$ TCID$_{50}$ of virus as described above. Half of the hamsters were challenged with PIV2 on day 29, the remaining half with PIV1 on day 32. Hamster lung and nasal turbinate tissues were harvested 4 days after challenge, and titer of challenge virus were determined as described above (Table 8). Sera were obtained before and 28 days after immunization and tested for their neutralizing antibody titer against PIV1 and PIV2.

TABLE 8

The chimeric rPIV3-1 virus expressing the HN glycoprotein of PIV2 (rPIV3-1.2HN) protects hamsters against challenge with both PIV1 and PIV2

| | Serum neutralizing antibody titer against indicated virus (reciprocal mean $\log_2$ ± SE)[b] | | | | Titer of challenge virus in indicated tissues ($\log_{10}\text{TCID}_{50}/g$ ± SE)[c] | | | |
|---|---|---|---|---|---|---|---|---|
| | PIV 1 | | PIV2 | | PIV1 | | PIV2 | |
| Immunizing virus[a] | pre | post | pre | post | NT | Lung | NT | Lung |
| rPIV3/JS | ≤4.0 ± 0.0 | ≤4.0 ± 0.0 | 4.5 ± 0.1 | 4.6 ± 0.2 | 5.4 ± 0.2 | 5.1 ± 0.1 | 6.8 ± 0.2 | 6.0 ± 0.3 |
| PIV2 | ≤4.0 ± 0.0 | ≤4.0 ± 0.0 | 4.3 ± 0.2 | 9.6 ± 0.2 | 5.7 ± 0.2 | 5.7 ± 0.2 | ≤1.2 | ≤1.2 |
| rPIV3-1 | 4.2 ± 0.1 | 8.5 ± 0.3 | 4.0 ± 0.0 | 4.2 ± 0.1 | ≤1.2 | ≤1.2 | 6.3 ± 0.1 | 6.5 ± 0.2 |
| rPIV3-1.2 HN | ≤4.0 ± 0.0 | 6.2 ± 0.2 | 4.1 ± 0.1 | 8.3 ± 0.2 | 2.3 ± 0.5 | ≤1.2 | ≤1.2 | ≤1.2 |
| rPIV3-1cp45 | ≤4.0 ± 0.0 | 6.2 ± 0.4 | ≤4.0 ± 0.0 | 4.0 ± 0.0 | 3.6 ± 0.3 | 2.7 ± 0.5 | 6.0 ± 0.1 | 5.7 ± 0.4 |
| rPIV3-1cp45.2HN | 4.0 ± 0.9 | 4.1 ± 0.1 | 4.0 ± 0.0 | 4.2 ± 0.1 | 5.1 ± 0.2 | 4.8 ± 0.2 | 6.8 ± 0.1 | 6.6 ± 0.2 |

[a]Hamsters in groups of 12 were immunized with $10^{5.3}$ TCID$_{50}$ of indicated virus intranasally on day 0.
[b]Serum was diluted 1:10 with OptiMEM and heat-inactivated by incubation at 56° for 30 min. The serum neutralizing antibody titer was determined on LLC-MK2, and the titers are expressed as reciprocal mean $\log_2$ ± standard error (SE).
[c]Half of the hamsters from each immunized group were challenged with $10^6$ TCID$_{50}$ PIV2 on day 29, and the remaining half were challenged with $10^6$ TCID$_{50}$ PIV1 on day 32. Tissue samples were harvested 4 days after challenge, and challenge virus titers are expressed as $\log_{10}$TCID$_{50}$/gram of tissue ± SE. NT = nasal turbinates.

As expected PIV3 provided no resistance against either PIV1 or PIV2 (Tao, *Vaccine* 17:1100–1108, 1999), while previous infection with PIV2 wild type virus and rPIV3-1 induced complete resistance to replication of PIV2 and PIV1 challenge viruses, respectively. In contrast to these viruses that provided protection against only one virus, rPIV3-1.2HN induced antibody to both PIV1 and PIV2 and included strong resistance to both PIV1 and PIV2 as indicated by the 1,000- to 10,000-fold reduction in replication of each virus in the upper and lower respiratory tract of rPIV3-1.2HN immunized hamsters. This indicated that a single recombinant chimeric PIV can induce resistance against two human viral pathogens. However, the derivative of rPIV3-1.2HN carrying the cp45 mutations failed to induce significant resistance to replication of wild type PIV1 or PIV2 challenge virus indicating that this particular recombinant chimeric virus is over-attenuated in hamsters. Introduction of one or several selected cp45 mutations, rather than the complete set of 12 mutations, into rPIV3-1.2HN can be done to adjust the level of attenuation of rPIV3-1.2HN to an appropriate level.

EXAMPLE VI

Construction of cDNAs Encoding rHPIV3 Viruses Containing Nucleotide Insertions

As discussed above, insertion of the measles HA ORF between either the N/P or P/M gene junction of the attenuated vector virus, rPIV3cp45L, as well as at the N/P, P/M, and HN/L junctions of wild type PIV3, further restricted its replication in the upper respiratory tract of hamsters, indicating that insertion of an additional gene at either location within the HPIV3 genome can augment attenuation of candidate vaccine viruses. In these exemplary aspects of the invention, the gene insert was relatively large (approximately 1900 nts). Further examples are provided herein that indicate the size of the insert specifies a selectable level of attenuation of the resulting recombinant virus. This was evaluated by introducing sequences of various lengths which were derived from a heterologous virus, exemplified by the RSV A2 strain, as single gene units (GUs) between the HPIV3 HN and L ORFs. The inserts were designed specifically to lack any significant ORF, whereby any effects observed would not be complicated by possible contribution of expressed protein. In order to distinguish between effects due to increased genome length versus expression of an additional mRNA, a second series of constructs was made in which inserts of similar sizes were introduced into the downstream noncoding region (NCR) of the HN gene. Thus, two series of rPIV3s were made containing insertions of increasing length: in the GU series, the insert was added as an extra gene encoding an extra mRNA, while in the NCR series the insert was made so that the gene number was unchanged.

Figure 6:
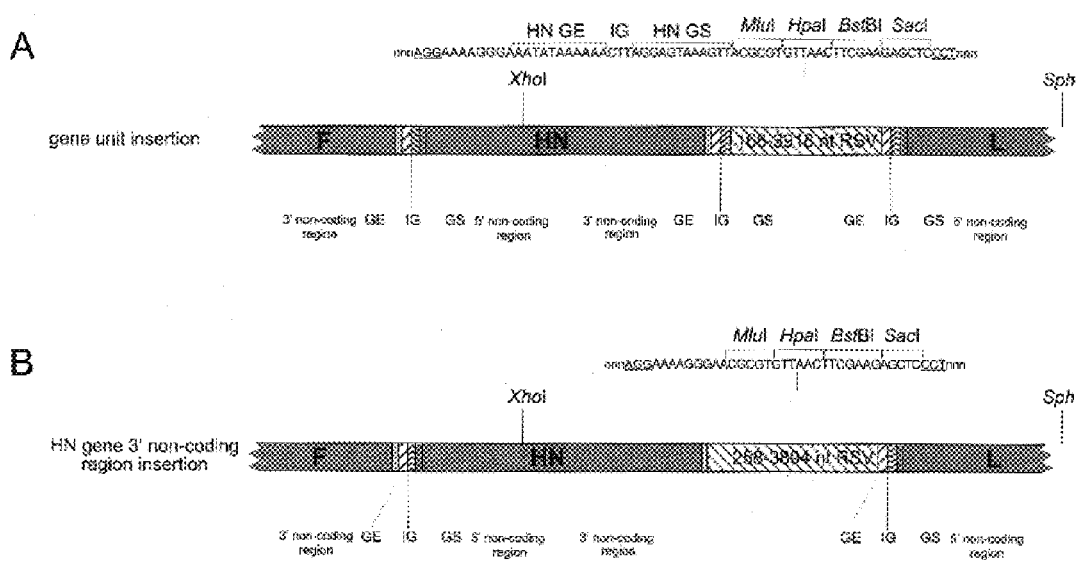
In FIG. 6, Panel B, HN gene 3'-NCR insertions were cloned into the HpaI site of the indicated 32 nt multiple cloning site, which had been cloned into the StuI restriction site as described in FIG. 6, Panel A. Inserted sequences were made to conform to the rule of six by insertion of short oligonucleotide duplexes into the MluI site in the multiple cloning site.
Figure 7:
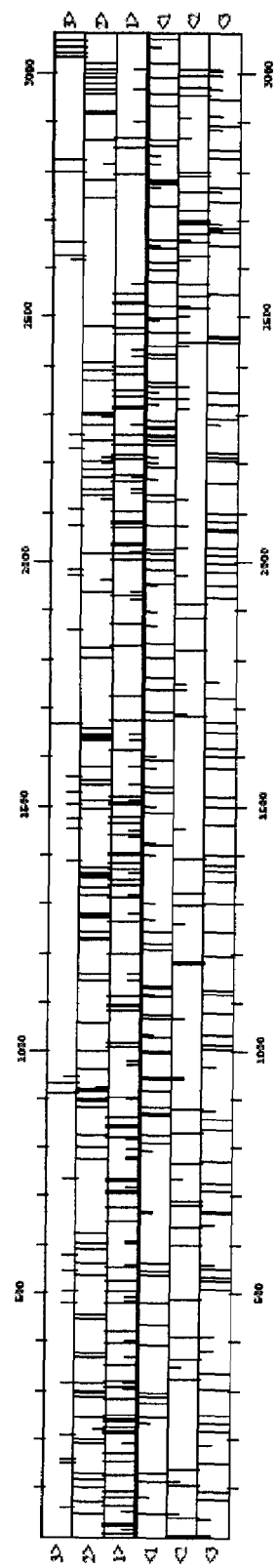
FIG. 7 illustrates open reading frames (ORFs) in the 3079 bp RSV insert. The six possible reading frames in the 3079 bp RSV fragment are shown (three in each orientation; 3, 2, 1, −1, −2, −3). Short bars represent translation start codons. Long bars represent translation stop codons. The 3079 bp fragment was inserted into the HN 3' NCR(NCR ins) or between the HN and L genes as a gene unit (GU ins) in such an orientation that the reading frames encountered by the PIV3 translation machinery correspond to −3, −2 and −1 in the figure. These reading frames contain numerous stop codons across the entire length of the sequence, and should therefore not produce any functional proteins.
Figure 8:
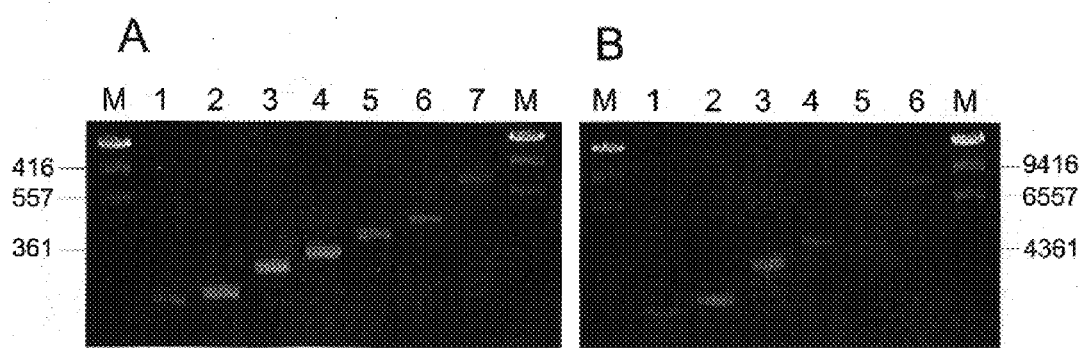
FIG. 8 demonstrates that rPIV3 insertion and extension mutants contain inserts of the appropriate size. RT-PCR was performed using a PIV3-specific primer pair flanking the insertion site, and RT-PCR products were separated by agarose gel electrophoresis. The expected size of the RT-PCR fragment for rPIV3 wt (also referred to as rJS) is 3497 bp and that for each of the other rPIV3s GU or NCR mutants is increased in length depending on the size of the insertion. Panel A depicts GU insertion (ins) mutants: 1. rPIV3 wt; 2. r168 nt GU ins; 2. r678 nt GU ins; 3. r996 nt GU ins; 4. r1428 nt GU ins; 5. r1908 nt GU ins; 6. r3918 nt GU ins. M: HindIII restriction enzyme digestion products of lamda phage DNA. Sizes of relevant size markers are indicated. Panel B depicts NCR insertion mutants: 1. rPIV3 wt; 2. r258 nt NCR ins; 3. r972 nt NCR ins; 4. r1404 nt NCR ins; 5. r3126 nt NCR ins; 6. r3894 nt NCR ins. M: HindIII restriction enzyme digestion products of lamda phage DNA. Sizes of relevant size markers are indicated.

Construction of cDNAs Encoding rHPIV3 Viruses Containing GU and 3'-NCR Insertions Insertion mutations were constructed in a pUC based plasmid, pUC118-Stu, containing the XhoI to SphI fragment (HPIV3 nts 7437–11317) of the full length HPIV3 clone p3/7(131)2G-Stu. Two separate plasmids were constructed as acceptor plasmids for insertion of GUs and HN gene 3'-NCR extensions (FIG. 6). In each, a synthetic oligonucleotide duplex containing multiple cloning sites was inserted into the unique Stu I site. The inserted sequence for the GU insertion plasmid contained a HN gene-end (GE) signal sequence, the conserved intergenic (IG) trinucleotide sequence, and a L gene-start (GS) signal sequence, cis-acting sequences that direct termination of the HN gene transcription and initiation of transcription of the inserted sequence, respectively (FIG. 6). Additional unique restriction endonuclease sites were included in the multiple cloning region to facilitate subsequent screening and subcloning. The 3'-NCR extension acceptor plasmid was similarly designed and constructed, but it lacked the cis-acting GE, IG, and GS sequences at its 5'-end (FIG. 6B, Table 9). The RSV antigenomic plasmid d53RSVsites or subgenomic plasmid pUC118FM2 (Table 9) were digested with the appropriate restriction enzymes, and fragments of the desired sizes were isolated by electrophoresis on agarose gels and ligated individually into the unique HpaI site of the GU or the HN gene 3'-NCR extension acceptor plasmid (FIG. 6; Table 9). Clones were screened to identify ones in which the RSV restriction fragments were inserted in the reverse orientation, an orientation in which all reading frames contained multiple stop codons (FIG. 7). Short synthetic oligonucleotide duplexes ranging in size from 13 to 17 nucleotides also were inserted as necessary into the GU or 3'-NCR acceptor plasmids to modify the genome length to conform to the "rule of six" (Table 9). The specific RSV sequences and size of the short synthetic oligonucleotides added are summarized in Table 9. Plasmid clones were sequenced through all restriction enzyme sites used for subcloning, and XhoI-SphI fragments containing insertion mutations conforming to the rule of six, either as GUs or HN gene NCR extensions, were cloned into the full-length PIV3 cDNA plasmid p3/7(131)2G+. One insert, containing the 1908 GU insert, also was placed into an antigenomic cDNA bearing the three L mutations of cp45.

tion was performed on vRNA using the Superscript II Preamplification System (Life Technologies) with random hexamer primers. The Advantage cDNA PCR kit (Clontech, CA) and sense (PIV3 nt 7108–7137) and antisense primers (PIV3 nt 10605–10576) were used to amplify fragments for restriction endonuclease digestion or sequence analysis. The PCR fragments were analyzed by agarose gel electrophoresis (FIG. 8) and sequencing. Each of the recovered rPIV3 insertion mutants contained insertions of the indicated sizes and they were next evaluated for their biological properties.

TABLE 9

Sources of nucleotides used to create the gene unit (GU) and HN gene 3' non coding region (NCR) extension insertions.

| Restriction fragment size (nts) | Restriction sites and nt position in the RSV antigenome | GU multiple cloning site (58 nt) + rule of 6 oligonucleotide[e] | GU insertion (total nts inserted) | NCR multiple cloning site (32 nt) + rule 6 oligonucleotide[e] | NCR insertion (total nts inserted) |
|---|---|---|---|---|---|
| 97[a] | Ssp1-Ssp1; 7272–7369 | +58 + 13 | 168 | nd | nd |
| 212[b] | Hpa1-Hpa1; 12243–12455 | nd | nd | +32 + 14 | 258 |
| 603[b] | Ssp1-Ssp1; 309–912 | +58 + 17 | 678 | nd | nd |
| 925[b] | Hpa1-Hpa1; 12455–13380 | +58 + 13 | 996 | +32 + 15 | 972 |
| 1356[b, c] | HincII-HincII; 5060–6417 | +58 + 14 | 1428 | +32 + 16 | 1404 |
| 1850[b, d] | Hpa1-Hpa1; 12455–13380 | +58 + 0 | 1908 | nd | nd |
| 3079[b] | EcoRV-Ec/13611; 1403–4482 | nd | nd | +32 + 15 | 3126 |
| 3845[b] | Sca1-Sca1; 344–4189 | +58 + 15 | 3918 | +32 + 17 | 3894 |

[a]Source of RSV sequence is pUC118FM2, a plasmid containing a subgenomic cDNA fragment of RSV subgroup A as described previously (Juhasz, K. et al, J Virol., 71:5814–5819, 1997.).
[b]Source of RSV sequence is D53 sites, a plasmid containing the entire RSV subgroup A cDNA sequence with several introduced point mutations as described previously. The previously described D53 sites plasmid was used to derive the rAsites virus descried in Whitehead, S., et al. J. Virol.,72:4467–4471, 1998.
[c]The gel purified 1356 nt fragment contained a 1 nt deletion compared to the predicted 1357 nt restriction endonuclease cleavage product.
[d]The 1850 nt fragment is a product of two 3' to 3' adjoined 925 nt restriction fragments.
[e]The following oligonucleotides were inserted into the MluI restriction site to conform all the inserted foreign sequences to the rule of six: 13 mer: CGCGGCAGGCCTG (SEQ ID NO: 26); 14 mer: CGCGGCGAGGCCTG (SEQ ID NO: 27); 15 mer: CGCGAGGCCTCCGCG (SEQ ID NO: 28); 16 mer: CGCGCCGCGGAGGCCT (SEQ ID NO: 29); 17 mer: CGCGCCCGCGGAGGCCT (SEQ ID NO: 30). nd, not done.

Recovery of Recombinant PIV3s Bearing Insertion Mutations

Full-length antigenomic cDNA derivatives bearing the insertion mutations and three support plasmids pTM(N), pTM(P no C) and pTM(L) (Durbin et al., *Virology* 235: 323–332, 1997; Durbin et al., *Virology* 261:319–330, 1999, each incorporated herein by reference) were transfected into HEp-2 monolayers in 6-well plates (Costar, MA) using LipofectACE (Life Technologies, MD), and the monolayers were infected with MVA-T7 as described previously (Durbin et al., *Virology* 235:323–332, 1997; Skiadopoulos et al., *J. Virol.* 72:1762–8, 1998, each incorporated herein by reference). After incubation at 32° C. for 4 days, the transfection harvest was passaged onto LLC-MK2 cells in T-25 flasks which were incubated at 32° C. for four to eight days. The clarified medium supernatant was subjected to plaque purification on LLC-MK2 cells as described previously (Durbin et al., *Virology* 235:323–332, 1997; Hall et al., *Virus Res.* 22:173–184, 1992; Skiadopoulos et al., *J. Virol.* 72:1762–8, 1998, each incorporated herein by reference). Each biologically-cloned recombinant virus was amplified twice in LLC-MK2 cells at 32° C. to produce virus for further characterization. Virus was concentrated from clarified medium by polyethylene glycol precipitation (Mbiguino et al., *J. Virol. Methods* 31:161–170, 1991, incorporated herein by reference), and viral RNA (vRNA) was extracted with Trizol Reagent (Life Technologies). Reverse transcrip-

EXAMPLE VII

Figure 9A:
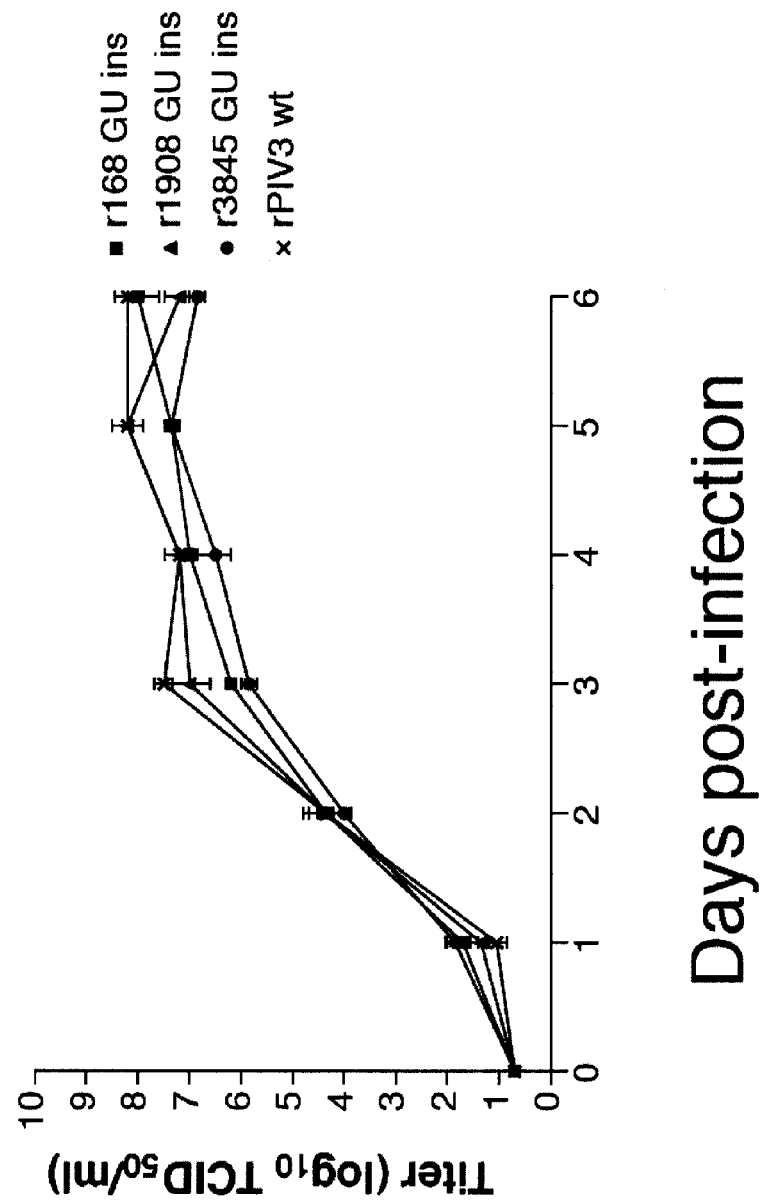
Figure 9B:
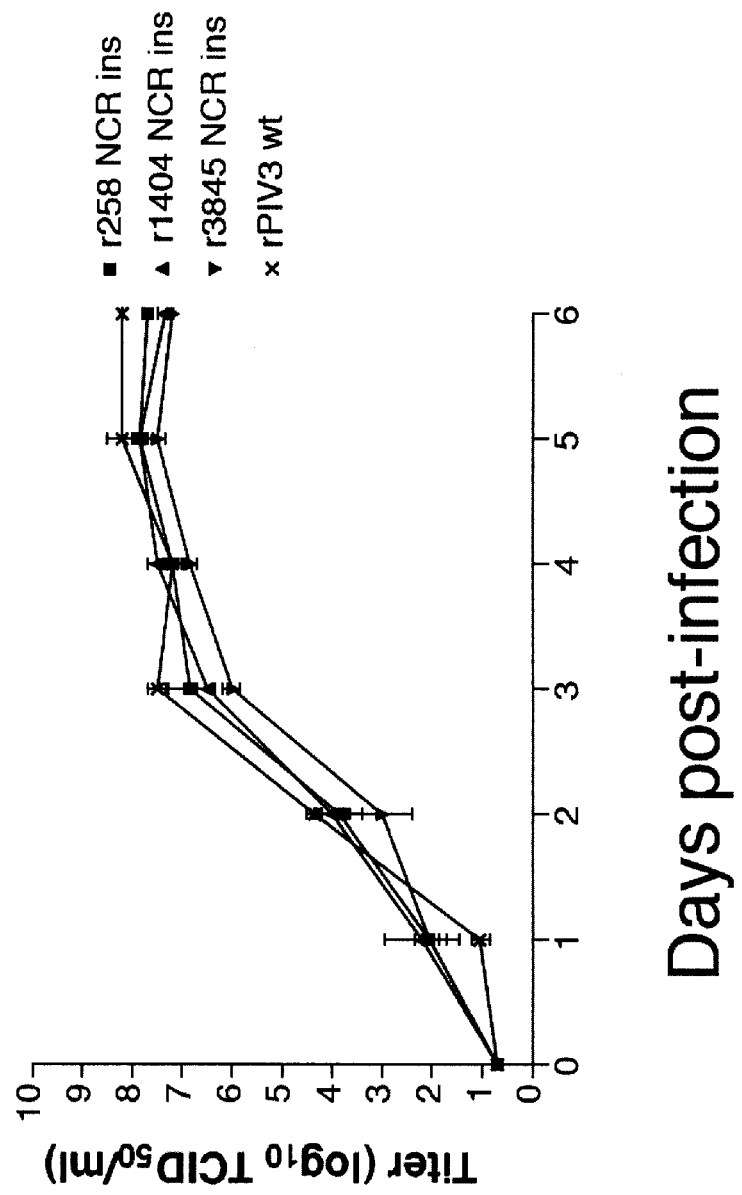

Replication of rHPIV3 Viruses Containing GU or NCR Inserts in Animals and in Tissue Culture Multi-Step Growth Curves The growth properties of the rPIV3 GU and NCR insertion mutants were compared to rPIV3 wt and rcp45$_L$ in vitro. As shown in FIG. 9, the rate of replication and the peak virus titer of each of the rPIV3s containing either the GU or NCR insertions was indistinguishable from that of rPIV3 wt indicating that insertion of sequences of at least 3918 nts in length does not affect virus replication in vitro.

Replication in Hamsters of rPIVs Containing GU Insertions

Hamsters were inoculated intranasally with $10^{6.0}$ TCID$_{50}$ rPIV3 wt, rcp45$_L$ or with one of the indicated mutant rPIV3s bearing GU insertions (Table 10). Lungs and nasal turbinates were harvested on day four after infection and the level of replication of each virus was determined. Insertion of GUs ranging in size from 168 nt up to 1908 nt did not significantly reduce viral replication in the respiratory tract of hamsters. However, insertion of a 3918 nt gene unit between the HN and L ORF of wild type PIV3 resulted in a 5 and 25-fold reduction in viral replication in the nasal turbinates and lungs, respectively. This indicates that gene unit insertions of this size are attenuating for a wild type virus whereas shorter sizes, e.g., below approximately 2000 nt, have little effect on replication of wild type virus in the respiratory tract of hamsters. Thus, GU length can be altered to determine a desired level of attenuation in PIV vaccine viruses.

TABLE 10

Replication of rPIV3 GU insertion mutants in the respiratory tract of hamsters

| Virus[a] | Mean virus titer ($\log_{10}$ TCID$_{50}$/g ± S.E.[b]) in: | |
|---|---|---|
| | Nasal Turbinates | Lungs |
| rPIV3 wt | 5.9 ± 0.2 | 6.0 ± 0.2 |
| r168 nt GU ins | 5.9 ± 0.1 | 6.4 ± 0.1 |
| r678 nt GU ins | 6.1 ± 0.1 | 6.2 ± 0.1 |
| r996 nt GU ins | 5.5 ± 0.2 | 5.4 ± 0.2 |
| r1428 nt GU ins | 5.9 ± 0.1 | 5.3 ± 0.6 |
| r1908 nt GU ins | 5.6 ± 0.1 | 5.7 ± 0.2 |
| r3918 nt GU ins | 5.2 ± 0.2 | 4.6 ± 0.3 |
| rcp45$_L$ | 3.1 ± 0.0 | 1.7 ± 0.2 |
| r1908 nt GU ins/cp45$_L$ | 1.8 ± 0.2 | 1.5 ± 0 |

[a]Hamsters, in groups of eight, were administered $10^{6.0}$ TCID$_{50}$ of virus intranasally in a 0.1 ml inoculum. Lungs and nasal turbinates were harvested four days later and virus titer was determined at 32° C.
[b]S.E.: Standard error.

As described above, the insertion of the HA gene of measles virus into the rJS wildtype and the attenuated cp45L virus further attenuated each virus for hamsters. Since the HA gene of measles virus is 1936 nt in length, we examined the effect of a similar size gene insertion (1908 nt) on replication of rcp45L. The 1908 gene insertion differs from the measles virus HA gene insertion in that it cannot synthesize a large polypeptide. When the 1908 nt GU insertion was combined with the cp45 L polymerase amino acid substitutions (r1908 nt GU ins/cp45$_L$ in Table 10), attenuation was augmented approximately 20-fold in the upper respiratory tract. Considered together, these findings indicate that GU insertions of approximately 3918 nts in length can attenuate a wild type PIV3 virus for hamsters and that GU insertions of about half this size can further attenuate an attenuated PIV3 vaccine candidate. Thus, GU insertions can have dual roles in the design of recombinant vaccines. The first role is to encode a protective antigen of a pathogen, and the second role is to confer an attenuation phenotype.

Replication in Hamsters of rPIVs Containing HN Gene 3'-NCR Insertions.

Hamsters were inoculated intranasally with rPIV3 control viruses or viruses bearing insertion mutations extending the length of the HN gene 3'-NCR (Table 11). Lungs and nasal turbinates were harvested four days after inoculation and the level of viral replication in each tissue was determined as described above. HN gene NCR insertions ranging in size from 258 nt up to 1404 nt did not significantly reduce viral replication in the respiratory tract of hamsters (Table 3). However, an insertion of 3126 nt effected a 16-fold reduction in viral titer in the upper and lower respiratory tracts of infected hamsters, and a 3894 nt HN gene NCR insertion resulted in a 12-fold reduction of viral replication in the upper and lower respiratory tracts, suggesting that increasing the genome length also confers an attenuating effect on viral replication.

Evaluation of the Level of Temperature Sensitivity of GU and NCR Insertions

The efficiency of plaquing (EOP) at permissive and non-permissive temperatures of rPIVs was determined on LLC-MK2 monolayers as described above (Table 12). At 32° C., viruses bearing GU insertions ranging in size from 168 nt up to 3918 nt and NCR insertions ranging in size from 258 nt up to 3894 nt had a plaque morphology that was similar to that of rPIV3 wt. However, at 39° C. and at higher temperatures all of the viruses bearing insertion mutations had a small plaque phenotype (Table 12). The GU insertions ranging in size from 996 nt up to 3918 nt yielded viruses that were not ts at 40° C. However, viruses bearing HN gene NCR insertions of 1404 nts or greater yielded viruses that were slightly ts at 40° C. with a gradient of temperature sensitivity proportional to the size of the insertion. Addition of the 1908 nt GU insertion to the cp45$_L$ backbone yielded a virus that was almost 100-fold more ts at 38° C. compared to rcp45$_L$, demonstrating that the ts phenotype specified by the 1908 nt GU insertion and by the L gene ts mutations is additive.

TABLE 11

Replication of rPIV3 NCR insertion mutants in the respiratory tract of hamsters

| Virus[a] | Mean virus titer ($\log_{10}$ TCID$_{50}$/g ± S.E.[b]) in: | |
|---|---|---|
| | Nasal Turbinates | Lungs |
| rPIV3 wt | 6.2 ± 0.1 | 6.4 ± 0.1 |
| r258 nt NCR ins | 5.9 ± 0.1 | 6.5 ± 0.1 |
| r972 nt NCR ins | 5.9 ± 0.1 | 6.6 ± 0.1 |
| r1404 nt NCR ins | 5.9 ± 0.2 | 6.6 ± 0.1 |
| r3126 nt NCR ins | 5.0 ± 0.1 | 5.2 ± 0.1 |
| r3894 nt NCR ins | 5.1 ± 0.1 | 5.3 ± 0.1 |
| rcp45$_L$ | 3.4 ± 0.1 | 1.9 ± 0.2 |

[a]Hamsters, in groups of eight, were administered $10^{6.0}$ TCID$_{50}$ of virus intranasally in a 0.1 ml inoculum. Lungs and nasal turbinates were harvested four days later and virus titer was determined at 32° C.
[b]S.E.: Standard error.

TABLE 12

Efficiency of plaque formation of rPIV3 GU and NCR insertion mutants at permissive and non-permissive temperatures

| Virus | Virus titer at indicated temperature ($\log_{10}$PFU/ml | | | | |
|---|---|---|---|---|---|
| | 32° C. | 37° C. | 38° C. | 39° C. | 40° C. |
| rPIV3 wt | 7.8 | ND | ND | 7.4 | 7.5 |
| r168 nt GU ins | 7.8 | ND | ND | 7.5[a] | 6.7[a] |
| r678 nt GU ins | 7.9 | ND | ND | 7.3[a] | 7.0[a] |
| r996 nt GU ins | 7.7 | ND | ND | 7.0[a] | 6.3[a] |
| r1428 nt GU ins | 7.8 | ND | ND | 7.4[a] | 6.4[a] |
| r1908 nt GU ins | 7.6 | ND | ND | 6.5[a] | 6.0[a] |
| r3918 nt GU ins | 6.3 | ND | ND | 5.7[a] | 5.0[a] |
| r258 nt NCR ins | 8.1 | ND | ND | 7.4[a] | 7.5[a] |
| r972 nt NCR ins | 8.2 | ND | ND | 7.8[a] | 7.8[a] |
| r1404 nt NCR ins | 6.7 | ND | ND | 5.2[a] | ≤3.7 |
| r3126 nt NCR ins | 7.4 | ND | ND | 6.4[a] | 4.5[a] |
| r3894 nt NCR ins | 7.4 | ND | ND | 5.3[a] | 5.0[a] |
| rcp45$_L$ | 7.8 | 7.3 | 6.0 | ≤0.7 | ND |
| r1908 nt GU ins/cp45$_L$ | 6.7 | 5.0[a] | 3.0[a] | <0.7 | ND |
| rcp45 | 8.1 | 6.7 | 5.7[a] | 2.0[a] | ND |

[a]Plaques were enumerated by immunoperoxidase staining after incubation for 6 days at the indicated temperature. Values which are underlined and in bold type represent the lowest restrictive temperature at which there was at least a 100-fold reduction of plaquing efficiency compared to the titer at 32° C., which is defined as the shut-off temperature of plaque formation.

Since the r3918 nt GU insertion mutant as well as the r3126 nt and r3894 nt NCR insertion mutants replicated efficiently in vitro but were restricted in replication in the respiratory tract of hamsters, these recombinants exhibit a novel, host-range attenuation phenotype.

Briefly summarizing the foregoing description and Examples, recombinant chimeric PIVs bearing heterologous viral genes or genome segments have been constructed in accordance with the description herein using a cDNA-based virus recovery system. Recombinant viruses made from cDNA replicate independently and can be propagated in the same manner as if they were biologically-derived viruses. In preferred embodiments, recombinant chimeric human PIV (HPIV) vaccine candidates bear one or more major antigenic determinant(s) of a HPIV, preferably in a background that is attenuated by one or more nucleotide modifications. Preferably, chimeric PIVs of the invention also express one or more protective antigens of another pathogen, for example a microbial pathogen. In these cases, the HPIV acts as an attenuated virus vector and is used with the dual purpose of inducing a protective immune response against one or more HPIVs as well as against the pathogen(s) from which the foreign protective antigen(s) was/were derived. As mentioned above, the major protective antigens of PIVs are their HN and F glycoproteins. The major protective antigens of other enveloped viruses, for example viruses that infect the respiratory tract of humans, that can be expressed by the HPIV vector from one or more extra transcriptional units, also referred to as gene units, are their attachment proteins, e.g., the G protein of RSV, the HA protein of measles virus, the HN protein of mumps virus, or their fusion (F) proteins, e.g., the F protein of RSV, measles virus or mumps virus. It is also be possible to express the protective antigens of non-enveloped viruses such as the LI protein of human papillomaviruses which could form virus-like particles in the infected hosts (Roden et al., *J. Virol.* 70:5875–83, 1996). In accordance with these teachings, a large array of protective antigens and their constituent antigenic determinants from diverse pathogens can be integrated within chimeric PIV of the invention to generate novel, effective immune responses.

At any given time in a vaccination schedule, it is possible to co-administer several PIV vector-based vaccine viruses that each expresses a different protective antigen from one or more additional gene units. In this way, it is possible to develop a multivalent vaccine against many human pathogens.

The present invention overcomes the difficulties inherent in prior approaches to vector based vaccine development and provides unique opportunities for immunization of infants during the first year of life against a variety of human pathogens. Previous studies in developing live-attenuated PIV vaccines indicate that, unexpectedly, rPIVs and their attenuated and chimeric derivatives have properties which make them uniquely suited among the nonsegmented negative strand RNA viruses as vectors to express foreign proteins as vaccines against a variety of human pathogens. The skilled artisan would not have predicted that the human PIVs, which tend to grow substantially less well than the model nonsegmented negative strand viruses and which typically have been underrepresented with regard to molecular studies, would prove to have characteristics which are highly favorable as vectors. It is also surprising that the intranasal route of administration of these vaccines has proven a very efficient means to stimulate a robust local and systemic immune response against both the vector and the expressed heterologous antigen. Furthermore, this route provides additional advantages for immunization against heterologous pathogens which infect the respiratory tract or elsewhere. These properties of PIV vectors are described herein above using examples of rPIV3 vectors which bear (i) a major neutralization antigen of measles virus expressed as a separate gene in wild type and attenuated backgrounds or (ii) major neutralization antigens of hPIV1 in place of the PIV3 neutralization antigens which express in addition a major neutralization antigen of hPIV2. These rPIV vectors were constructed using wild type and attenuated backgrounds. In addition, the description herein demonstrates the ability to readily modify the level of attenuation of the PIV vector backbone. According to one of these methods, varying the length of genome inserts in a chimeric PIV of the invention allows for adjustment of the attenuation phenotype, which is only apparent in wild type derivatives using very long inserts.

The present invention provides six major advantages over previous attempts to immunize the young infant against measles virus or other microbial pathogens. First, the PIV recombinant vector into which the protective antigen or antigens of measles virus or of other microbial pathogens is inserted is an attenuated rPIV bearing one or more attenuating genetic elements that are known to attenuate virus for the respiratory tract of the very young human infant (Karron et al., *Pediatr. Infect. Dis. J.* 15:650–654, 1996; Karron et al., *J. Infect. Dis.* 171:1107–1114, 1995a; Karron et al., *J. Infect. Dis.* 172:1445–1450, 1995b). This extensive history of prior clinical evaluation and practice greatly facilitates evaluation of derivatives of these recombinants bearing foreign protective antigens in the very young human infant.

The second advantage is that the rPIV backbone carrying the HA or other protective antigen of another human pathogen will induce a dual protective immune response against (1) the PIV, for which there is a compelling independent need for a vaccine as indicated above, and (2) the measles virus or other microbial pathogen whose protective antigen is expressed by the vector. This contrasts with the VSV-measles virus HA recombinant described above which will induce immunity to only one human pathogen, i.e., the measles virus, and in which the immune response to the vector itself is at best irrelevant or is potentially disadvantageous. The coding sequences of the foreign genes inserted into various members of the Mononegavirales Order of viruses have remained intact in the genomes of the most of the recombinant viruses following multiple cycles of replication in tissue culture cells, indicating that members of this group of viruses are excellent candidates for use as vectors (Bukreyev et al., *J. Virol.* 70:6634–41, 1996; Schnell et al., *Proc. Natl. Acad. Sci. USA* 93:11359–65, 1996a; Singh et al., *J. Gen. Virol.* 80:101–6; Yu et al., *Genes Cells* 2:457–66, 1997).

Another advantage provided by the invention is that use of a human pathogen backbone, for which there is a need for a vaccine, will favor the introduction of such a live attenuated virus vector into an already crowded early childhood immunization schedule. In addition, immunization via the mucosal surface of the respiratory tract offers various advantages. A live attenuated PIV3 was shown to replicate in the respiratory tract of rhesus monkeys and to induce a protective immune response against itself in the presence of high quantities of maternally-acquired PIV3 antibodies. The ability of two candidate PIV3 vaccines to infect and to replicate efficiently in the upper respiratory tract of the very young human infant who possess maternally-acquired antibodies has also been demonstrated (Karron et al., *Pediatr. Infect. Dis. J.* 15:650–654, 1996; Karron et al., *J. Infect. Dis.*

171:1107–1114, 1995a; Karron et al., *J. Infect. Dis.* 172: 1445–1450, 1995b). This is in contrast to the currently licensed measles virus vaccine which is poorly infectious when administered to the upper respiratory tract of humans and which is highly sensitive to neutralization when administered parenterally to young children (Black et al., *New Ens. J. Med.* 263:165–169, 1960; Kok et al., *Trans. R. Soc. Trop. Med. Hyg.* 77:171–6, 1983; Simasathien et al., *Vaccine* 15:329–34, 1997). The replication of the HPIV vector in the respiratory tract will stimulate the production of both mucosal IgA and systemic immunity to the HPIV vector and to the expressed foreign antigen. Upon subsequent natural exposure to wild type virus, e.g., measles virus, the existence of vaccine-induced local and systemic immunity should serve to restrict its replication at both its portal of entry, i.e., the respiratory tract, as well as at systemic sites of replication.

Yet another advantage of the invention is that chimeric HPIVs bearing heterologous sequences replicate efficiently in vitro demonstrating the feasibility for large scale production of vaccine. This is in contrast to the replication of some single-stranded, negative-sense RNA viruses which can be inhibited in vitro by the insertion of a foreign gene (Bukreyev et al., *J. Virol.* 70:6634–41, 1996). Also, the presence of three antigenic serotypes of HPIV, each of which causes significant disease in humans and hence can serve simultaneously as vector and vaccine, presents a unique opportunity to sequentially immunize the infant with antigenically distinct variants of HPIV each bearing the same foreign protein. In this manner the sequential immunization will permit the development of a primary immune response to the foreign protein which can be boosted during subsequent infections with the antigenically distinct HPIV also bearing the same or a different foreign protein or proteins, i.e., the protective antigen of measles virus or of another microbial pathogen. It is also likely that readministration of homologous HPIV vectors will also boost the response to both HPIV and the foreign antigen since the ability to cause multiple reinfections in humans is an unusual but characteristic attribute of the HPIVs (Collins et al., In "Fields Virology" (B. N. Fields, D. M. Knipe, P. M. Howley, R. M. Chanock, J. L. Melnick, T. P. Monath, B. Roizman, and S. E. Straus, Eds.), Vol. 1, pp. 1205–1243. Lippincott-Raven Publishers, Philadelphia, 1996).

Yet another advantage is that the introduction of a gene unit into a PIV vector has several unexpected, but highly desirable effects, for the production of attenuated viruses. First, the insertion of gene units expressing the HA of measles virus or the HN of PIV2 each specify a host range phenotype on the PIV vector that has not been previously recognized, i.e., the resulting PIV vector replicates efficiently in vitro but is restricted in replication in vivo in both the upper and lower respiratory tracts. These findings identify the insertion of a gene unit expressing a viral protective antigen as an attenuating factor for the PIV vector, a desirable property in live attenuated virus vaccines of the invention.

Although the foregoing invention has been described in detail by way of example for purposes of clarity of understanding, it will be apparent to the artisan that certain changes and modifications may be practice within the scope of the appended claims which are presented by way of illustration not limitation. In this context, various publications and other references have been cited within the foregoing disclosure for economy of description. Each of these references are incorporated herein by reference in its entirety for all purposes.

What is claimed is:

1. An infectious chimeric parainfluenza virus (PIV) comprising a major nucleocapsid (N) protein, a nucleocapsid phosphoprotein (P), a large polymerase protein (L), and a partial or complete human parainfluenza virus 3 (HPIV3) background genome or antigenome combined with one or more heterologous gene(s) or genome segment(s) encoding a complete open reading frame or one or more antigenic determinant(s) selected from the group consisting of:

an HN glycoprotein of HPIV 1,
an HN glycoprotein of HPIV2,
an F glycoprotein of HPIV1 and
an F glycoprotein of HPIV2, said heterologous gene(s) or gene segment(s) being operably linked to regulatory sequences operable in said HPIV3 genome or antigenome, to form a chimeric parainfluenza virus (PIV) genome or antigenome;

said partial or complete PIV background genome or antigenome comprising a polynucleotide encoding a wild-type L protein of the background PIV;

said infectious chimeric PIV being attenuated for replication at least 10-fold in the respiratory tract of a primate host infected with said chimeric PIV.

2. An infectious chimeric parainfluenza virus (PIV) comprising a major nucleocapsid (N) protein, a nucleocapsid phosphoprotein (P), a large polymerase protein (L), and a partial or complete human parainfluenza virus 3(HPIV3) background genome or antigenome combined with one or more heterologous gene(s) or genome segment(s) encoding a complete open reading frame or one or more antigenic determinant(s) of HN and/or F glycoproteins of HPIV1 and/or HPIV2, said heterologous gene(s) or gene segment(s) being operably linked to regulatory sequences operable in said HPIV3 genome or antigenome, to form a chimeric PIV genome or antigenome;

said heterologous gene(s) or genome segment(s) being inserted into the HPIV3 background genome at one or more site(s) selected from the group consisting of a site between the P and M open reading frames, a site between the N and P open reading frames, a site between the HN and L open reading frames.

3. The infectious chimeric PIV of claim 2, in which the heterologous gene(s) or genome segment is inserted between the HN and L open reading frames.

4. An infectious parainfluenza virus parainfluenza virus (PIV) comprising a major nucleocapsid (N) protein, a nucleocapsid phosphoprotein (P), a large polymerase protein (L), and a partial or complete human parainfluenza virus (HPIV) background genome or antigenome combined with one or more heterologous gene(s) or genome segment(s), said heterologous gene(s) or genome segment(s) being inserted at one or more site(s) selected from the group consisting of a site between the P and M open reading frames, a site between the N and P open reading frames, a site between the HN and L open reading frames, which is attenuated in vivo at least 10-fold compared to replication of the corresponding wild-type PIV.

5. The infectious PIV of claim 4, in which the heterologous gene(s) or genome segment(s) are inserted at a site between the HN and L open reading frames.

6. The infectious PIV of claim 4, in which the heterologous gene(s) or genome segment(s) comprise a gene start sequence and a gene end sequence of the background HPIV virus genome or antigenome.

7. The infectious PIV of claim 4, in which the heterologous gene(s) or genome segment(s) are inserted into the non-coding region of the HN gene of the background HPIV genome or antigenome.

8. The infectious PIV of claim 4, in which the heterologous gene(s) or genome segment(s) is a polynucleotide that does not encode a protein.

9. The infectious PIV of claim 4, in which the heterologous gene(s) or genome segment(s) have a length of at least 996 nucleotides.

10. The infectious PIV of claim 8, in which the polynucleotide has a length of at least 996 nucleotides.

11. The infectious PIV of claim 10, in which the polynucleotide comprises a gene start sequence and a gene end sequence of the background HPIV virus genome or antigenome.

12. The infectious PIV of claim 10, in which the polynucleotide sequence is inserted into a 3' untranslated region of a PIV gene.

13. The infectious PIV of claim 4, in which the heterologous gene(s) or genome segment(s) have a length of at least 3000 nucleotides.

14. The infectious PIV of claim 4, in which the heterologous gene(s) or genome segment(s) are obtained from the measles HA gene.

15. An infectious chimeric parainfluenza virus (PIV) comprising a major nucleocapsid (N) protein, a nucleocapsid phosphoprotein (P), a large polymerase protein (L), and a partial or complete human parainfluenza virus 3 (HPIV3) background genome or antigenome combined with one or more heterologous gene(s) or genome segment(s) encoding a complete open reading frame or one or more antigenic determinant(s) of HN and/or F glycoproteins of HPIV 1 and/or HPIV2, said heterologous gene(s) or gene segment(s) being operably linked to regulatory sequences operable in said HPIV3 genome or antigenome, to form a chimeric PIV genome or antigenome;

said partial or complete HPIV3 background genome or antigenome including a mutation encoding a substitution of amino acid 456 of the L protein by another amino acid.

16. An immunogenic composition comprising an immunologically effective amount of the infectious chimeric PIV of any one of claims 1–15 and a physiologically acceptable carrier.

17. An isolated polynucleotide encoding a partial or complete human parainfluenza virus 3 (HPIV3) background genome or antigenome combined with one or more heterologous gene(s) or genome segment(s) encoding a complete open reading frame or one or more antigenic determinant(s) selected from the group consisting of:
an HN glycoprotein of HPIV 1,
an HN glycoprotein of HPIV2,
an F glycoprotein of HPIV1 and
an F glycoprotein of HPIV2,
said heterologous gene(s) or gene segment(s) being operably linked to regulatory sequences operable in said HPIV3 genome or antigenome, to form a chimeric parainfluenza virus (PIV) genome or antigenome;
said partial or complete PIV background genome or antigenome comprising a polynucleotide encoding a wild-type L protein of the background PIV.

18. An isolated polynucleotide comprising a polynucleotide sequence encoding a partial or complete human parainfluenza virus 3(HPIV3) background genome or antigenome combined with one or more heterologous gene(s) or genome segment(s) encoding a complete open reading frame or one or more antigenic determinant(s) of HN and/or F glycoproteins of HPIV1 and/or HPIV2, said heterologous gene(s) or gene segment(s) being operably linked to regulatory sequences operable in said HPIV3 genome or antigenome, to form a chimeric PIV genome or antigenome;
said heterologous gene(s) or genome segment(s) being inserted into the HPIV3 background genome at one or more site(s) selected from the group consisting of a site between the P and M open reading frames, a site between the N and P open reading frames, a site between the HN and L open reading frames.

19. The isolated polynucleotide of claim 18, in which the heterologous gene(s) or genome segment is inserted between the HN and L open reading frames.

20. An isolated polynucleotide comprising a polynucleotide sequence encoding a partial or complete human parainfluenza virus (HPIV) background genome or antigenome combined with one or more heterologous gene(s) or genome segment(s), said heterologous gene(s) or genome segment(s) being inserted at one or more site(s) selected from the group consisting of a site between the P and M open reading frames, a site between the N and P open reading frames, a site between the HN and L open reading frames.

21. The isolated polynucleotide of claim 20, in which the heterologous gene(s) or genome segment(s) are inserted at a site between the HN and L open reading frames.

22. The isolated polynucleotide of claim 20, in which the heterologous gene(s) or genome segment(s) comprise a gene start sequence and a gene end sequence of the background HPIV virus genome or antigenome.

23. The isolated polynucleotide of claim 20, in which the heterologous gene(s) or genome segment(s) are inserted into the non-coding region of the HN gene of the background HPIV genome or antigenome.

24. The isolated polynucleotide of claim 20, in which the heterologous gene(s) or genome segment(s) is a polynucleotide that does not encode a protein.

25. The isolated polynucleotide of claim 20, in which the heterologous gene(s) or genome segment(s) have a length of at least 996 nucleotides.

26. The isolated polynucleotide of claim 24, in which the polynucleotide has a length of at least 996 nucleotides.

27. The isolated polynucleotide of claim 26, in which the polynucleotide comprises a gene start sequence and a gene end sequence of the background HPIV virus genome or antigenome.

28. The isolated polynucleotide of claim 26, in which the polynucleotide sequence is inserted into a 3' untranslated region of a PIV gene.

29. The isolated polynucleotide of claim 20, in which the heterologous gene(s) or genome segment(s) have a length of at least 3000 nucleotides.

30. The isolated polynucleotide of claim 20, in which the heterologous gene(s) or genome segment(s) are obtained from the measles HA gene.

31. An isolated polynucleotide comprising a polynucleotide sequence encoding a partial or complete human parainfluenza virus 3 (HPIV3) background genome or antigenome combined with one or more heterologous gene(s) or genome segment(s) encoding a complete open reading frame or one or more antigenic determinant(s) of HN and/or F glycoproteins of HPIV 1 and/or HPIV2, said heterologous gene(s) or gene segment(s) being operably linked to regulatory sequences operable in said HPIV3 genome or antigenome, to form a chimeric PIV genome or antigenome;
said partial or complete HPIV3 background genome or antigenome including a mutation encoding a substitution of amino acid 456 of the L protein by another amino acid.

32. An expression vector comprising in operable linkage:
i) a promoter operable in a mammalian cell or in vitro;
ii) the polynucleotide of any one of claims 17–31; and
iii) a transcription terminator sequence operable in a mammalian cell or in vitro.

33. A method for making an infectious PIV from one or more isolated polynucleotides comprising:
expressing in a cell or cell-free lysate an expression vector comprising the isolated polynucleotide of any one of claims 17, 18, 20 AND 31, and N, P and L proteins of a PIV;
wherein one or more of said N, P and L proteins of a PIV can be encoded by the isolated polynucleotide or by one or more separate expression vectors.

* * * * *